United States Patent
Takaishi et al.

(10) Patent No.: US 12,097,189 B1
(45) Date of Patent: *Sep. 24, 2024

(54) PHARMACEUTICAL COMPOSITION FOR MODIFIED RELEASE

(71) Applicant: ASTELLAS PHARMA INC., Tokyo (JP)

(72) Inventors: Yuuki Takaishi, Tokyo (JP); Soichiro Nakamura, Tokyo (JP); Yutaka Takahashi, Tokyo (JP); Takashi Nishizato, Tokyo (JP); Daisuke Murayama, Tokyo (JP); Emiko Murayama, Tokyo (JP); Kazuhiro Sako, Tokyo (JP)

(73) Assignee: ASTELLAS PHARMA INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/613,281

(22) Filed: Mar. 22, 2024

Related U.S. Application Data

(63) Continuation of application No. 18/437,323, filed on Feb. 9, 2024.

(51) Int. Cl.
| | | |
|---|---|---|
| *A61K 31/426* | (2006.01) | |
| *A61K 9/00* | (2006.01) | |
| *A61K 9/16* | (2006.01) | |
| *A61K 9/20* | (2006.01) | |
| *A61K 9/28* | (2006.01) | |
| *A61K 47/36* | (2006.01) | |

(52) U.S. Cl.
CPC .......... *A61K 31/426* (2013.01); *A61K 9/0004* (2013.01); *A61K 9/1652* (2013.01); *A61K 9/2031* (2013.01); *A61K 9/205* (2013.01); *A61K 9/2054* (2013.01); *A61K 9/2072* (2013.01); *A61K 9/2086* (2013.01); *A61K 9/2846* (2013.01); *A61K 9/2866* (2013.01); *A61K 47/36* (2013.01)

(58) Field of Classification Search
None
See application file for complete search history.

(56) References Cited

U.S. PATENT DOCUMENTS

| | | |
|---|---|---|
| 4,929,629 A | 5/1990 | Jeffery |
| 5,234,691 A | 8/1993 | Uemura et al. |

(Continued)

FOREIGN PATENT DOCUMENTS

| | | |
|---|---|---|
| AU | 199889288 B2 | 5/1999 |
| BR | PI 0316080 A | 9/2005 |

(Continued)

OTHER PUBLICATIONS

Notice of Opposition to a European Patent, Patent No. EP2554168 to Astellas Pharma Inc., Opponent STADA Arzneimittel AG, Dated Oct. 24, 2018.

(Continued)

*Primary Examiner* — Isis A Ghali
(74) *Attorney, Agent, or Firm* — Venable LLP

(57) ABSTRACT

A pharmaceutical composition for modified release comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a maximum blood drug concentration (Cmax) when administered in fasted state is 400 ng/ml or less, is disclosed.

30 Claims, 7 Drawing Sheets

(56) References Cited

U.S. PATENT DOCUMENTS

| | | |
|---|---|---|
| 5,382,601 A | 1/1995 | Nuernberg et al. |
| 5,393,779 A | 2/1995 | Holloway et al. |
| 5,681,582 A | 10/1997 | Gills et al. |
| 6,204,285 B1 | 3/2001 | Fabiano et al. |
| 6,251,925 B1 | 6/2001 | Donaldson et al. |
| 6,346,532 B1 | 2/2002 | Maruyama et al. |
| 6,355,805 B1 | 3/2002 | Choi et al. |
| 6,368,628 B1 | 4/2002 | Seth |
| 6,419,954 B1 | 7/2002 | Chu et al. |
| 6,436,441 B1 | 8/2002 | Sako et al. |
| 6,451,814 B1 | 9/2002 | Ashwell et al. |
| 6,488,963 B1 | 12/2002 | McGinity et al. |
| 6,562,375 B1 | 5/2003 | Sako et al. |
| 6,566,377 B2 | 5/2003 | Day et al. |
| 6,699,503 B1 | 3/2004 | Sako et al. |
| 6,805,881 B1 | 10/2004 | Kanikanti et al. |
| 7,108,865 B2 | 9/2006 | Curatolo et al. |
| 7,342,117 B2 | 3/2008 | Kawazoe et al. |
| 7,442,387 B2 | 10/2008 | Sako et al. |
| 7,982,049 B2 | 7/2011 | Kawazoe et al. |
| 8,835,474 B2 | 9/2014 | Takasu et al. |
| 8,877,214 B2 | 11/2014 | Takaishi et al. |
| 10,842,780 B2 | 11/2020 | Takaishi et al. |
| 11,707,451 B2 | 7/2023 | Takaishi et al. |
| 2001/0006982 A1 | 7/2001 | Cruz et al. |
| 2003/0072802 A1 | 4/2003 | Cutler et al. |
| 2003/0147950 A1 | 8/2003 | Platteeuw et al. |
| 2003/0198619 A1 | 10/2003 | Dong et al. |
| 2003/0203024 A1 | 10/2003 | Sako et al. |
| 2003/0212063 A1 | 11/2003 | Lafontaine et al. |
| 2003/0215508 A1 | 11/2003 | Davis et al. |
| 2004/0033263 A1 | 2/2004 | Seroff et al. |
| 2004/0087658 A1 | 5/2004 | Moebius |
| 2004/0198822 A1 | 10/2004 | Fraser et al. |
| 2004/0213845 A1 | 10/2004 | Sugihara et al. |
| 2005/0042289 A1 | 2/2005 | Chu et al. |
| 2005/0100602 A1 | 5/2005 | Sako et al. |
| 2005/0100603 A1 | 5/2005 | Sako et al. |
| 2005/0106247 A1 | 5/2005 | Venkatesh et al. |
| 2005/0154041 A1 | 7/2005 | Michel et al. |
| 2005/0191351 A1 | 9/2005 | Kidane et al. |
| 2005/0261328 A1 | 11/2005 | Wienrich et al. |
| 2005/0287185 A1 | 12/2005 | Wong et al. |
| 2006/0051416 A1 | 3/2006 | Rastogi et al. |
| 2006/0099257 A1 | 5/2006 | Langridge et al. |
| 2006/0115540 A1 | 6/2006 | Takasu et al. |
| 2007/0026065 A1 | 2/2007 | Benke et al. |
| 2007/0078181 A1 | 4/2007 | Michel |
| 2008/0275076 A1 | 11/2008 | Holm et al. |
| 2009/0011018 A1 | 1/2009 | Kondo et al. |
| 2009/0093529 A1 | 4/2009 | Takasu et al. |
| 2010/0144807 A1 | 6/2010 | Takaishi et al. |
| 2021/0085654 A1 | 3/2021 | Takaishi et al. |

FOREIGN PATENT DOCUMENTS

| | | |
|---|---|---|
| BR | 0213570-1 B1 | 2/2018 |
| CA | 2263659 A1 | 2/1998 |
| CA | 2315235 A1 | 6/1999 |
| CA | 2328348 A1 | 10/1999 |
| CA | 2336853 A1 | 1/2000 |
| CA | 2387705 A1 | 2/2001 |
| CA | 2507266 A1 | 6/2004 |
| CA | 2144077 C | 5/2005 |
| CA | 2490299 C | 8/2008 |
| CA | 2305802 C | 11/2008 |
| CA | 2387705 C | 6/2009 |
| CN | 1091004 A | 8/1994 |
| CN | 1711085 A | 12/2005 |
| EP | 0 661 045 A1 | 7/1995 |
| EP | 0 679 400 B1 | 8/1999 |
| EP | 0 958 835 A1 | 11/1999 |
| EP | 1 028 111 A1 | 8/2000 |
| EP | 1205190 A1 | 5/2002 |
| EP | 1440969 A1 | 7/2004 |
| EP | 1559427 A1 | 8/2005 |
| EP | 1 753 395 A2 | 2/2007 |
| EP | 1 813 274 A1 | 8/2007 |
| EP | 1974725 A1 | 10/2008 |
| EP | 2 119 442 A1 | 11/2009 |
| EP | 2345410 A1 | 7/2011 |
| EP | 2 554 168 A1 | 2/2013 |
| EP | 2554168 B1 | 1/2018 |
| GB | 2356197 A | 5/2001 |
| JP | 40-2053 S | 2/1965 |
| JP | 3140465 B2 | 3/2001 |
| JP | 2001-114736 A | 4/2001 |
| JP | 2005-162736 A | 6/2005 |
| JP | 2005-162737 A | 6/2005 |
| JP | 2005-519884 A | 7/2005 |
| JP | 3815496 B2 | 8/2006 |
| JP | 2008-532953 A | 8/2008 |
| JP | 5625855 B2 | 11/2014 |
| JP | 5849946 B2 | 2/2016 |
| KR | 10-0355130 B | 1/2003 |
| KR | 2005-0072809 A | 7/2010 |
| KR | 2005-0107298 A | 9/2011 |
| TW | 200400057 A | 1/2004 |
| TW | 200509991 A | 3/2005 |
| WO | 94/06414 A1 | 3/1994 |
| WO | 97/18814 A1 | 5/1997 |
| WO | 99/47125 A1 | 9/1999 |
| WO | 2000/016747 A1 | 3/2000 |
| WO | 02/00622 A2 | 1/2002 |
| WO | 02/48134 A2 | 6/2002 |
| WO | 03/039531 A1 | 5/2003 |
| WO | 03/053401 A2 | 7/2003 |
| WO | 2004/041276 A2 | 5/2004 |
| WO | 2004/093843 A1 | 11/2004 |
| WO | 2005/020993 A1 | 3/2005 |
| WO | 2008/084698 A1 | 7/2008 |
| WO | 2009/019599 A2 | 2/2009 |
| WO | 2009/052353 A2 | 4/2009 |
| WO | 2010/038690 A1 | 4/2010 |
| ZA | 2005/03510 B | 12/2006 |

OTHER PUBLICATIONS

Notice of Opposition to a European Patent, Patent No. EP2554168 to Astellas Pharma Inc., Opponent Alfred E. Tiefenbacher (GmbH & Co. KG), Dated Oct. 30, 2018.

Yoshinobu Yamazaki et al., "Species Differences in the Distribution of β3-Adrenoceptor Subtypes in Bladder Smooth Muscle," 124 Brit. J. Pharmacol. 593-599 (1998).

Observations in Response to Oppositions to European Patent No. 2 554 168 B1 (Mar. 25, 2019).

Office Action, May 13, 2013, U.S. Appl. No. 13/073,677.

Office Action, Oct. 18, 2012, U.S. Appl. No. 13/073,721.

Office Action, Sep. 17, 2012, U.S. Appl. No. 13/073,677.

Osamu Yamaguchi, "β3-Adrenoceptors in Human Detrusor Muscle", 59 (Suppl. 5A) Urology 25-29 (2002).

Paul Abrams et al., "The Standardisation of Terminology in Lower Urinary Tract Function: Report from the Standardisation Sub-Committee of the International Continence Society," 21 Neurourol. Urodyn. 167-178 (2002).

Penelope A. Longhurst et al., "Pharmacological techniques for the in vitro study of the urinary bladder," 45 J. Pharmacol. Tox. Met. 91-108 (2001).

Peter G. Welling, "Effects of Food on Drug Absorption," 16 Annu. Rev. Nutr. 383-415 (1996).

Philip L. Gould, "Salt Selection for Basic Drugs," 33(1-3) Int. J. Pharm. 201-217 (1986).

Philippines Patent Application No. 1/2011/500628, Examination Report, Jul. 18, 2013, 2 pages.

PH Patent Application No. Jan. 2011/500628, Second Examination Report (Office Action), May 26, 2014, 2 pages.

Preliminary Office Action in Brazilian Application No. PI0919466-5 (Sep. 2, 2019).

Prescribing Information of Myrbetriq, Aug. 2016.

(56) References Cited

OTHER PUBLICATIONS

Rajendra K. Khankari et al., "Pharmaceutical Hydrates," 248 Thermochimica Acta 61-79 (1995).
Reexamination Notice, Jan. 30, 2015, Chinese Patent Application No. 200980138691.9, 14 pages.
Response to Communication Pursuant to Art. 94(3) EPC and Third Party Observations in European Application No. 09817723.1 (May 20, 2019).
Response to Communication Pursuant to Art. 94(3) EPC and Third Party Observations in European Application No. 09817723.1 (Aug. 28, 2018).
Response to Communication Pursuant to Art. 94(3) EPC and Third Party Observations in European Application No. 11762748.9 (Aug. 2, 2017).
Response to Communication Pursuant to Art. 94(3) EPC in European Application No. 09817723.1 (Mar. 13, 2020).
Response to Communication Pursuant to Art. 94(3) EPC in European Application No. 09817723.1 (May 13, 2020).
Response to Communication Pursuant to Rules 70(2) and 70a(2) EPC in European Application No. 09817723.1 (May 18, 2015).
Response to Communication Pursuant to Rules 70(2) and 70a(2) EPC in European Application No. 11762748.9 (Nov. 9, 2015).
Response to Submissions of Opponents in Oppositions to European Patent No. 2 554 168 B1 (Oct. 18, 2019).
Response to Summons in Oppositions to European Patent No. 2 554 168 B1 (Oct. 10, 2019).
Richard J. Bastin et al., "Salt Selection and Optimisation Procedures for Pharmaceutical New Chemical Entities," 4(5) Org. Process Res. Dev. 427-435 (2000).
Russia Patent Application No. 2011117274/15, Office Action, Mar. 6, 2013, 6 pages.
Sathish Ummadi et al., "Overview on Controlled Release Dosage Form," 3(4) Int. J. Pharma Sci. 258-269 (2013).
Shin-Etsu Chemical Co., LTD, "Low-substituted hydroxypropyl cellulose NF, L-HPC" http://www.elementoorgankia.ru/files/lhpc.pdf, Cellulose & Pharmaceutical Department, 23 pages, accessed on Jun. 30, 2014.
Siepmann et al., Polymer Blends for Controlled Release Coatings, Journal of Controlled Release, 2008, pp. 1-15, vol. 125, Elsevier B.V.
Skelly et al, In Vitro and In Vivo Testing and Correlation for Oral Controlled/Modified Release Dosage Forms. Report of the 2nd Workshop Held Dec. 1988, Washington, DC, USA, Journal of Controlled Release, 1990, pp. 95-106, vol. 14, Elsevier Science Publishers B.V., Amsterdam, The Netherlands.
State Intellectual Property Office of the People's Republic of China: Chinese Patent Application No. 20150642287.2; Notification of the Second Office Action; issued Jul. 25, 2018.
State Intellectual Property Office of the People's Republic of China: First Office Action; CN Patent Application No. 20150642287.2; Nov. 3, 2017.
Stephen Byrn et al., "Pharmaceutical Solids: A Strategic Approach of Regulatory Considerations," 12(7) Pharm. Res. 945-954 (1995).
Stephen R. Byrn, Solid-State Chemistry of Drugs, pp. 6-11 (1982).
Submission by Hexal AG in re Opposition to European Patent No. 2 554 168 (Oct. 10, 2019).
Submission by Lederer & Keller Patentanwälte Partnerschaft mbB in re Opposition to European Patent No. 2 554 168 (Oct. 10, 2019).
Submission by STADA Arzneimittel AG in re Opposition to European Patent No. 2 554 168 (Oct. 10, 2019).
Summons to Attend Oral Proceedings in re Opposition to European Patent No. 2 554 168 B1 (Jul. 17, 2019).
Takao Fujimura et al., "Expression and Possible Functional Role of the β3-Adrenoceptor in Human and Rat Detrusor Muscle," 161 J. Urol. 680-685 (1999).
Takasu, T., et al., Effect of R-2-(2-aminothiazol-4-yl)-4'-{2-[(2-hydroxy-2-phenylethyl)amino]ethyl} acetanilide (YM178), a novel selective beta3-adrenoceptor agonist, on bladder function, J Pharmacol Exp Ther., May 2007, pp. 321-322, vol. 642-7, Epub 2007. (abstract only).

Technical Examination Report in Brazilian Application No. BR122019026041-9 (Jul. 10, 2020).
Technical Examination Report in Brazilian Application No. PI0919466-5 (Jul. 10, 2020).
The European Agency for the Evaluation of Medicinal Products, Note for Guidance on Modified Release Oral and Transdermal Dosage Forms: Section II (Pharmacokinetics and Clinical Evaluation), Jul. 1999, 12 pages, London.
The U Co., LTD: Petitioner's Brief; Korean Case No. 2017 Dang 569 Patent Invalidation Action re KR 10-1524164; Apr. 14, 2017.
US Non-final Office Action, U.S. Appl. No. 13/073,721, filed Jul. 30, 2014, 24 pages.
Wen et al., Oral Controlled Release Formulation Design and Drug Delivery, Theory to Practice, 2010, Pages preface and 1-9, John Wiley & Sons, Inc.
Written Demand for Trial for Invalidation of Japanese Patent No. 5849946 (Apr. 2020).
Invalidation Action Request in Taiwanese Patent No. I478712 (Nov. 2021).
Notice of Opposition to European Patent No. 2 345 410 by Dr. Jan Bulle (Sep. 2021).
Notice of Opposition to European Patent No. 2 345 410 by Hamm&Wittkopp Patentanwälte PartmbB (Sep. 2021).
Notice of Opposition to European Patent No. 2 345 410 by Sanovel Ilaç Sanayi Ve Ticaret Anonim Sirketi (Sep. 2021).
Notice of Opposition to European Patent No. 2 345 410 by Teva Pharmaceutical Industries Ltd. (Sep. 2021).
Notice of Opposition to European Patent No. 2 345 410 by Brand Murray Fuller LLP (Sep. 2021).
Medical Review(s): Clinical Review of Mirabegron, pp. 1-8, 12, 34 (Jun. 2012).
Online Extract from Therapeutic Advances in Urology with Abstract of Karl-Erik Andersson, "Prospective Pharmacologic Therapies for the Overactive Bladder," 1(2) Therapeutic Advances in Urology 71-83 (May 2009).
Online Extract from Current Opinion in Urology with Abstract for Karl-Erik Andersson et al., "Pharmacological Treatment of Overactive Bladder: Report from the International Consultation on Incontinence," 19(4) Current Opinion in Urology 380-394 (Jul. 2009).
Ann T. Hanna-Mitchell et al., "New Insights into the Pharmacology of the Bladder," 18(4) Curr. Opin. Urol. 347-352 (Jul. 2008).
Abstract 674 for C.R. Chapple et al., "Clinical Proof of Concept Study (BLOSSOM) Shows Novel B3 Adrenoceptor Agonist YM178 is Effective and Well Tolerated in the Treatment of Symptoms of Overactive Bladder," 7(3) Eur. Urol. Suppl. 239 (2008).
ClinicalTrials.gov Archive, History of Changes for Study: NCT00989104, Study to Test the Efficacy and Safety of the Beta-3 Agonist YM178 in Subjects With Symptoms of Overactive Bladder (SCORPIO), Study Record Version Jun. 2, 2008.
ClinicalTrials.gov Archive, History of Changes for Study: NCT00989104, Study to Test the Efficacy and Safety of the Beta-3 Agonist YM178 in Subjects With Symptoms of Overactive Bladder (SCORPIO), Study Record Version Apr. 16, 2009.
ClinicalTrials.gov Archive, History of Changes for Study: NCT00662909, Study to Test the Efficacy and Safety of the Beta-3 Agonist YM178 in Subjects With Symptoms of Overactive Bladder (ARIES), Study Record Version Apr. 17, 2008.
ClinicalTrials.gov Archive, History of Changes for Study: NCT00662909, Study to Test the Efficacy and Safety of the Beta-3 Agonist YM178 in Subjects With Symptoms of Overactive Bladder (ARIES), Study Record Version May 20, 2009.
ClinicalTrials.gov Archive, History of Changes for Study: NCT00965926, A Study to Investigate the Food Effect on the Pharmacokinetics of YM178 in Healthy, Non-elderly Volunteers, Study Record Version Sep. 8, 2009.
ClinicalTrials.gov Archive, History of Changes for Study: NCT00939757, Study of the Effect of Food on the Pharmacokinetics of Mirabegron, Study Record Version Aug. 3, 2009.
ClinicalTrials.gov Archive, History of Changes for Study: NCT00940121, Pharmacokinetics of Oral Mirabegron With Different Release Rates Versus Intravenous (IV) Mirabegron, Study Record Version Aug. 3, 2009.

(56) References Cited

OTHER PUBLICATIONS

Toshiyuki Takasu et al., "Effect of (R)-2-(2-Aminothiazol-4-yl)-4'-{2-[(2-hydroxy-2-phenylethyl)amino]ethyl} Acetanilide (YM178), a Novel Selective β3-Adrenoceptor Agonist, on Bladder Function," 321(2) JPET 642-647 (2007).
International Nonproprietary Names for Pharmaceutical Substances (INN), Recommended INN: List 60, Prepublication Copy, pp. 1-30 (ND).
K.-E. Andersson et al., "Bladder Pharmacology and Treatment of Lower Urinary Tract Symptoms: Recent Advances," 1 (2) UroToday International Journal, 15 pages (Aug. 2008).
Overview of Drug Development, Novartis, pp. 1-17 (2008).
Leon Lachman et al. (eds.), "The Theory and Practice of Industrial Pharmacy," 3rd Ed., Ch. 14: Nicholas G. Lordi, "Sustained Release Dosage Forms," pp. 430-456 (1986).
Michael E. Aulton (ed.), "Pharmaceutics: The Science of Dosage Form Design," 2nd Ed., pp. 294-302 (2002).
Kurt H. Bauer et al., "Pharmazeutische Technologie", 4th Ed., pp. 424-425 (1993).
Atul Tiwari et al., "Current and Emerging Investigational Medical Therapies for the Treatment of Overactive Bladder," 15(9) Expert Opin. Investig. Druqs 1017-1037 (2006).
Yamanouchi Press Release, Pharmaceutical Online (May 1999).
Yamanouchi Press Release, Outsourcing-pharma.com of Sep. 2004 (Last Updated Jul. 2008).
Yamanouchi Press Release, Outsourcing-pharma.com May 2004 (Last Updated Jul. 2008).
Declaration of Yuuki Takaishi in U.S. Appl. No. 13/073,677 (Dated Feb. 2013).
Raymond C. Rowe et al. (eds.), "The Handbook of Pharmaceutical Excipients," 6th Ed., pp. 317-322, 424-428 (2009).
Ramandeep Basra et al., "A Review of Solifenacin in the Treatment of Urinary Incontinence," 4(1) Ther. Clin. Risk Manag. 117-128 (2008).
Claim Form and Particular of Claim (Claim No. HP-2021000014) (Apr. 2021).
Astellas' Annual Report, pp. 1-78 (2008).
ClinicalTrials.gov, Study: NCT01604928, Study to Test the Efficacy and Safety of YM178 in Subjects With Symptoms of Overactive Bladder (Blossom), Feb. 16, 2017.
ClinicalTrials.gov Study: NCT00337090, A Study of YM178 in Patients With Symptomatic Overactive Bladder (DRAGON), Jul. 2, 2013.
ClinicalTrials.gov, Study: NCT00410514, A Study of Mirabegron (YM178) in Men With Lower Urinary Tract Symptoms (LUTS) and Bladder Outlet Obstruction (BOO), Apr. 4, 2014.
ClinicalTrials.gov, Study: NCT00527033, A Study of YM178 in Patients With Symptomatic Overactive Bladder, Study Feb. 16, 2017.
Consolidated List of Cited Documents in Opposition to European Patent No. 2 345 410 (Oct. 2021).
Answering Affidavit of Michael Du Plooy in Invalidation Proceeding of South African Patent No. 2011/02406 (Aug. 2023) (with Annexes).
Confirmatory Affidavit of Izaan Van Der Merwe in Invalidation Proceeding of South African Patent No. 2011/02406 (Aug. 2023) (with Annexes).
Supporting Affidavit of Roderick Bryan Walker in Invalidation Proceeding of South African Patent No. 2011/02406 (Aug. 2023) (with Annexes).
Submission by Hamm&Wittkopp Patentanwälte PartmbB in Opposition to European Patent No. 2 345 410 (Aug. 2023).
W.A. Ritschel et al. (eds), "Die Tablette—Handbuch der Entwicklung, Herstellung und Qualitätssicherung," 2nd ed, pp. 42-44 (2002).
ClinicalTrials.gov Study: NCT00337090, A Study of YM178 in Patients With Symptomatic Overactive Bladder (DRAGON), Submitted Jul. 1, 2013.
Memorandum and Order in *Astellas Pharma Inc.* v. *Sandoz Inc., et al.*; 1:20CV1589; Case 1:21-cv-00664-JFB-CJB (Jun. 2023).
Submission by Sandoz AG in Opposition to European Patent No. 2 345 410 (Jul. 2023).
H.S. Malhotra et al., "Barnidipine," 61(7) Drugs 989-996 (2001).
J. de Leon et al., "Haloperidol Half-Life After Chronic Dosing," 24 J. Clin. Psychopharmacol. 656-660 (Dec. 2004).
Valium (diazepam) FDA Label, 2008.
Submission by Teva Pharmaceutical Industries Ltd. in Opposition to European Patent No. 2 345 410 (Aug. 2023).
Clinical Study Protocol for ISN/Protocol No. 178-CL-008, 12 pages (ND).
Protocol for Phase 1 Study of YM178—ISN/Protocol No. 178-CL-041, 7 pages (ND).
Clinical Study Protocol for ISN/Protocol No. 178-CL-044 (DRAGON), 17 pages (ND).
Protocol for Phase II Study of YM178—ISN/Protocol No. 178-CL-045, 17 pages (ND).
Protocol for Phase 3 Study of YM178—ISN/Protocol No. 178-CL-046 (SCORPIO), 16 pages (ND).
Clinical Study Report, North American Phase 3 Pivotal Study (ARIES)—ISN/Protocol No. 178-CL-047, 35 pages (ND).
Informed Consent for ISN/Protocol No. 178-CL-049 (Taurus), 16 pages (ND).
Protocol for Phase 2 Study of YM178—ISN/Protocol No. 178-CL-060, IND 69,416, 27 pages (ND).
Protocol for Phase III Study of YM178 (Mirabegron)—ISN/Protocol No. 178-CL-074 (Capricorn), 35 pages (ND).
Protocol for Phase 1 Study of YM178—ISN/Protocol No. 178-CL-076, 16 pages (ND).
Protocol for Pharmacokinetic Study of YM178—ISN/Protocol No. 178-CL-078, 11 pages (ND).
Clinical Study Agreement with Principal Investigator for ISN/Protocol Nos. 178-CL-047 and 178-CL-049, 5 pages (ND).
First Expert Report of Prof. Kevin Shakesheff (with CV) in *Astellas Pharma Inc.* v. *Teva Pharmaceutical Industries Ltd. et al.*, Claim No. HP-2021-000014 (May 2022).
Second Expert Report of Prof. Kevin Shakesheff in *Astellas Pharma Inc.* v. *Teva Pharmaceutical Industries Ltd. et al.*, Claim No. HP-2021-000014 (Jul. 2022).
Expert Declaration of Prof. Kevin Shakesheff in Opposition to European Patent No. 2 345 410 (Aug. 2023).
Declaration of Fabien Roy in Opposition to European Patent No. 2 345 410 (Aug. 2023).
Consent Form for ISN/Protocol No. 178-CL-044 (DRAGON), 22 pages (ND).
"What is Pharmaceutical Deformulation?" PLS Analytical Webpage, 3 pages (2023).
K. Sudharsan Reddy et al., "Miscibility Studies of Hydroxypropyl Cellulose/Poly(Ethylene Glycol) in Dilute Solutions and Solid State," 2012 Int. J. Carbohydr. Chem. 1-9, Article JD 906389 (Sep. 2012).
Wolfgang Radke et al., "Tips & Tricks: Trouble Analyzing PEGs?" 18(4) col. 18-21 (Apr. 2022).
Yanxiang Li et al., "Synthesis and Phase Transition of Cellulose-Graft-Poly(Ethylene Glycol) Copolymers," 110(3) J. Appl. Polym. Sci. 1797-1803 (Nov. 2008).
Ines Baer et al., "NIR Analysis of Cellulose and Lactose—Application to Ecstasy Tablet Analysis," 167(2-3) Forensic Sci. Int. 234-241 (Jul. 2006).
R.S. Lanigan et al., "Final Report on the Safety Assessment of BHT," 21(Suppl. 2) Int. J. Toxicol. 19-94 (2002).
JP XV—Dissolution Test/Reagents, Test Solutions/General Tests, pp. 116, 194, 239 (ND).
Approved Judgment in *Astellas Pharma Inc.* v. *Teva Pharmaceutical Industries Ltd et al.*, Case No. HP-2021-000014 (Oct. 2023).
Communication Pursuant to Article 94(3) EPC in European Application No. 20 212 426.9 (Nov. 2023).
Written Refutation in the Trial for Invalidation of Japanese Patent No. 5849946 (Oct. 2020).
Takaya Nagisa, "Interaction Between Drugs and Foods (2), Interaction Between Drugs and Diets," 89(2) Clinical Nutrition 203-209 (Aug. 1996) (Exhibit A11).
Masahiro Wada, "Impact of Diet in Absorption of Drug," 14(11) Dispensing and Information 63-67 (Oct. 2008) (Exhibit A12).

(56) References Cited

OTHER PUBLICATIONS

Igata Kotsuji, "Interaction Between Drugs and Foods (1), What is Drug Interaction?" 89(1) Clinical Nutrition 73-79 (Jul. 1996) (Exhibit A13).
Clinical Pharmacokinetics Tests of Drug Products, PMSB Notification No. 796, pp. 1-14 (Jun. 2001) (Exhibit A14).
Oral Hearing Brief in the Trial for Invalidation of Japanese Patent No. 5849946 (Jan. 2021).
Hiromu Kondo et al., "Product Development With the use of Oral Drug Controlled Release Technology and Current Trend," 31-3 Drug Delivery System 210-218 (2016) (Exhibit A15).
Pharmaceutical Interview Form of Betanis Tablets, pp. 3-4 (Dec. 2019) (Exhibit A16).
Notification of Reexamination of Chinese Application No. 201510642287.2 (Feb. 2021).
Yaodong Yan, "Sustained-Release and Modified-Release Formulations," Chapter 1, p. 1 (May 2006).
Changjiang Wang et al. (eds.), "Diabetes," 1st ed., pp. 4-6 (Feb. 1998).
Shubao Liu (ed), "Pharmaceutics of Pharmaceutical Senior Professional Educational Series of Textbooks," p. 505 (Aug. 2004).
Jennifer B. Dressman et al. (eds), "Oral Drug Absorption: Prediction and Assessment," 2nd ed., pp. 100-107 ("Food Effect on Drug Absorption and Dosage Form Performance") (2001).
Decision of Reexamination No. 110276, pp. 1-10 (2016).
Hidetoshi Shimizu et al., "The Influence of Food on the Bioavailability of Slow-Release Metoprolol Tartrate 120 mg Tablet in Healthy Volunteers and Serum Protein Binding of Metoprolol," 6(4) Drug News, pp. 561, 574-578 (1991).
Masako Suzuki et al., "Bioequivalence Study of Mesalazine Tablets 250mg 'AKP'," 59(4) Medicine and Pharmacy 583-592 (Apr. 2008).
Wenquan Liang (ed.), "Biopharmaceutics and Pharmacokinetics," 2nd ed., Section III: Pharmacokinetics of Sustained-Release and Controlled-Release Preparations, p. 53 (Jan. 2004).
Report on the Filing or Determination of an Action Regarding a Patent or Trademark re U.S. Pat. No. 10,842,780: *Astellas Pharma Inc.* v. *Aurobindo Pharma Ltd.* (Case 1:21-cv-00425-JFB; filed Mar. 2021).
Extended European Search Report in European Application No. 20212426.9 (May 2021).
Archana Desai et al. (eds.), "Gibaldi's Drug Delivery Systems in Pharmaceutical Care," Chapters 2-3, pp. 11-42 (2007).
Technical Examination Report in Brazilian Application No. BR122020021232-2 (Apr. 2021).
Third Party Observations by Althaia S.A. Indústria Farmacêutica in Brazilian Application No. BR122020021232-2 (submitted Feb. 2021).
Trial Decision in the Trial for Invalidation of Japanese Patent No. 5849946 (Apr. 2021).
Report on the Filing or Determination of an Action Regarding a Patent or Trademark re U.S. Pat. No. 10,842,780: *Astellas Pharma Inc.* v. *Sandoz Inc.* (Case 1:21-cv-00664-JFB; filed May 2021).
Letter from Teva Pharmaceutical Industries Ltd. in Opposition to European Patent No. 2 345 410 (Sep. 2022).
Brahma N. Singh, "Effects of Food on Clinical Pharmacokinetics" 37(3) Clin. Pharmacokinet. 213-255 (Sep. 1999).
Shah et al., "Effects of Food on the Single-Dose Pharmacokinetics/ Pharmacodynamics of Tizanidine Capsules and Tablets in Healthy Volunteers," 28(9) Clin. Ther. 1308-1317 (Sep. 2006).
Expert Report of Dr. Graham E. Blakey from *Astellas Pharma Inc.* v. *Teva Pharmaceutical Industries Limited et al.*, Claim No. HP-2021-000014, UK High Court (dated Jun. 2022).
Robert J. Wills et al., "Multiple-Dose Pharmacokinetics of Diazepam Following Once-Daily Administration of a Controlled-Release Capsule," 5(4) Therapeutic Drug Monitoring 423-426 (Dec. 1983).
Expert Report of Professor Duncan Craig from *Astellas Pharma Inc.* v. *Teva Pharmaceutical Industries Limited et al.*, Claim No. HP-2021-000014, UK High Court (dated Jun. 2022).

D. Wagner et al. "Intestinal Drug Efflux: Formulation and Food Effects," 50 Adv. Drug Delivery Rev. S13-S31 (2001).
Archive of http://www.imagesrising.com/J'.Qt/ocas.shtml (Aug. 2008).
Guidance for Bioequivalence Studies of Generic Products, National Institute of Health Sciences, Japan, pp. 1-26 (Dec. 2006).
Harry Van Wezel et al., "Pharmacologic Therapy of Ischemic Heart Disease," in "Vascular Anesthesia," Joel A. Kaplan (ed.), pp. 155-186 (1991).
EudraCT Summary and Index for Study 2005-002256-17, "A Randomized, Double-Blind, Parallel Group, Placebo and Active Controlled, Multi-Center Dose Ranging Study with the Beta-3 Agonist YM178 in Patients with Symptomatic Overactive Bladder (DRAGON)," from European Trials Register at www.clinicaltrialsregister.eu (available on Mar. 2011).
Study Details for Study NCT00662909, "A Study to Assess Efficacy and Safety of the Beta-3 Agonist Mirabegron (YM178) in Patients with Symptoms of Overactive Bladder (ARIES)," from www.ClinicalTrials.gov (Dec. 2017).
Study Details for Study NCT00688688, "Study to Test the Long Term Safety and Efficacy of the Beta-3 Agonist Mirabegron (YM178) in Patients With Symptoms of Overactive Bladder (TAURUS)," from www.ClinicalTrials.gov (Dec. 2017).
Michael E. Aulton, ed., Pharmaceutics: The Science of Dosage Form Design, 1st ed., pp. 1-13 (1988).
Dow METHOCEL Brochure (Jul. 2000).
Raymond C. Rowe et al. eds, Handbook of Pharmaceutical Excipients, 4th ed., pp. 89-92, 97-100, 158-160, 200-202, 247-249, 283-286, 289-293, 297-300, 323-332, 371-377, 381-382, 447-450, 454-461, 474-483, 508-513, 556-559, 596-599, 622-625, 644-645, 694-697 (2003).
Prescribing Information for ENABLEX® (2004).
A. Sandberg et al., "Design of a New Multiple-Unit Controlled-Release Formulation of Metoprolol—Metoprolol CR," 33 Eur. J. Clinical Pharmacology S3-S7 (1988).
Paul Abrams et al., "Overactive Bladder Significantly Affects Quality of Life," 6 Am. J. of Managed Care S580-S590 (Jul. 2000).
Ramandeep K. Basra et al., "A Review of Adherence to Drug Therapy in Patients with Overactive Bladder," 102 BJU Int. 774-779 (2008).
Stephen M. Berge et al., "Pharmaceutical Salts," 66(1) J. Pharm. Scis 1-19 (1977).
Christopher R. Chapple et al., The Effects of Antimuscarinic Treatments in Overactive Bladder: An Update of Systematic Review and Meta-Analysis, 54 Eur. Urology 543-562 (2008).
Christopher R. Chapple et al., "Clinical Proof of Concept Study (Blossom) Shows Novel β3 Adrenoceptor Agonist YM178 is Effective in the Treatment of Symptoms of Overactive Bladder," 7 Eur. Urol. Suppl. 239 (2008).
S.S. Davis et al., Transit of Pharmaceutical Dosage Forms Through the Small Intestine, 27 Gut 886-892 (1986).
Formulating Sustained Release Pharmaceutical Products with METHOCEL, Dow Chemical Brochure, pp. 1-18 (1982).
Formulating for Controlled Release with METHOCEL Cellulose Ethers, Dow Chemical Brochure, pp. 1-32 (1987).
Jennifer B. Dressman et al. eds., Oral Absorption Prediction and Assessment, Ch. 1 pp. 1-9; and Ch. 11, pp. 183-195 (2000).
FIP Guidelines for Dissolution Testing of Solid Oral Products, Joint Report of the Section of Official laboratories and Medicines Control Services and the Section of Industrial Pharmacists of the F.I.P., pp. 1-12 (download on May 2, 2022:https://www.fip.org/file/1557).
Tondalaya Gamble et al., "Patient Perspective in the Management of Overactive Bladder, Focus on Transdermal Oxybutynin," 2 Patient Preference & Adherence 349-356 (2008).
Chantal Gauthier et al., "Interspecies Differences in the Cardiac Negative Inotropic Effects of B3-Adrenoceptor Agonists," 290 J. Pharmacol. Exp. Ther. 687-693 (1999).
Hashim Hashim et al., "Treatment Options for the Overactive Bladder Syndrome," 2 Therapy 921-936 (2005).
J.E. Hogan, "Hydroxypropylmethylcellulose Sustained Release Technology," 15(6-7) Drug Dev. Ind. Pharm. 975-999 (1989).

(56) References Cited

OTHER PUBLICATIONS

Shun-Ji Jin et al., "Paroxetine Hydrochloride Controlled Release POLYOX® Matrix Tablets: Screening of Formulation Variables using Plackett-Burman Screening Design," 31 Arch. Pharm. Res. 399-405 (2008).
Clarissa Kripke, "Anticholinergic Drugs for Overactive Bladder," 73 Am. Fam. Physician 66 (2006).
William Kuteesa et al., "Anticholinergic Drugs for Overactive Bladder," 29(1) Austl. Prescriber 22-24 (Feb. 2006).
Sum Lam et al., "Pharmacologic Management of Overactive Bladder," 2 Clinical Interventions in Aging 337-345 (2007).
Rong-Kun Chang et al., "Sustained Drug Release from Tablets and Particles Through Coating," in Herbert A. Lieberman et al. eds., Pharmaceutical Dosage Forms: Tablets, vol. 3, 2nd ed., pp. 199-302 (1990).
E. Ochoa Machiste et al., "Effect of UV Light Exposure on Hydrophilic Polymers Used as Drug Release Modulators in Solid Dosage Forms," 15 J. Drug Del. Sci. Tech., 151-157 (2005).
L. Maggi et al., "High Molecular Weight Polyethylene Oxides (PEOs) as an Alternative to HPMC in Controlled Release Dosage Forms," 195 Int. J. Pharm. 229-238 (2000).
L. Maggi et al., "Photostability of Extended-Release Matrix Formulations," 55 Eur. J. Pharm. Biopharm. 99-105 (2003).
Kathryn Phelps, "Long-Acting Overactive Bladder Drugs Have Less Risk," Consumer Reports, Pink Sheet, pp. 1-4 (Sep. 2006) (https://pink.pharmaintelligence.informa.com/PS047576/Long-Acting-Overactive-Bladder-Drugs-Have-Less-Risk--Consumer-Reports).
Kazuhiro Sako et al., "Influence of Water Soluble Fillers in Hydroxypropylmethylcellulose Matrices on In Vitro and In Vivo Drug Release," 81 J. Controlled Release 165-172 (2002).
Massaki Sawa et al., "Recent Developments in the Design of Orally Bioavailable B3-Adrenergic Receptor Agonists," 13 Curr. Med. Chem. 25-37 (2006).
David R. Staskin, "Overactive Bladder in the Elderly," 22 Drugs & Aging 1013- 1028 (2005).
Avinash G. Thrombe, "Assessment of the Feasibility of Oral Controlled Release in an Exploratory Development Setting," 10(17) Drug Discovery Today 1159-1166 (2005).
M. Victoria Velasco et al., "Influence of Drug:Hydroxypropylmethylcellulose Ratio, Drug and Polymer Particle Size and Compression Force on the Release of Diclofenac Sodium from HPMC Tablets," 57 J. Controlled Release 75-85 (1999).
Barry D. Weiss, "Selecting Medications for the Treatment of Urinary Incontinence," 71(2) Am. Fam. Physician 315-322 (Jan. 2005).
Prescribing Information for Detrol™ (Mar. 1998).
Prescribing Information for Detrol® LA (Dec. 2000).
UK Patient Information Leaflet for Propiverine Hydrochloride 15 mg Coated Tablets (May 2008).
Detrunorm XL 30 mg Modified Release Capsules, UK Public Assessment Report, pp. 1-24 (Apr. 2006).
Prescribing Information for Ditropan® (Apr. 2003).
Prescribing Information for Ditropan® XL (Dec. 1998).
Prescribing Information for Oxytrol™ (Feb. 2003).
Prescribing Information for Sanctura® (Jul. 2006).
NDA 22-103 Approval Letter for Sanctura XR™ (Aug. 2007).
Prescribing Information for Sanctura XR™ (Aug. 2007).
Prescribing Information for VESIcare® (May 2007).
Study Details for Study NCT00427596, "A Two-Part Study to Evaluate the Safety, Tolerability and Pharmacokinetics of Four MR Formulations and Food Effect of GW427353 (Solabegron) in Healthy Adult Subjects," from Clinical Trials.gov (Oct. 2008).
Alexandra Hicks et al., "GW427353 (Solabegron), a Novel, Selective β3-Adrenergic Receptor Agonist, Evokes Bladder Relaxation and Increases Micturition Reflex Threshold in the Dog," 323(1) J. Pharmacol. Exp. Ther. 202-209 (2007).
Y. Igawa et al., "Possible β3-Adrenoceptor-Mediated Relaxation of the Human Detrusor", 164 Acta Physiol Scand 117-118 (1998).
Chapple, C.R., "The Oral Controlled Absorption System (OCAS): The Evolution of Tamsulosin for the Treatment of Lower Urinary Tract Symptoms Suggestive of Benign Prostatic Hyperplasia (LUTS/BPH)", European Urology Supplements, 4 (2005), 20-22.
Technical Examination Report in Brazilian Application No. PI0919466-5 (Nov. 24, 2020).
Third Party Observations by Sandoz do Brasil Industria Farmaceutica Ltda in Brazilian Application No. PI0919466-5 (submitted Oct. 26, 2020).
Third Party Observations by Value Pharma Investimentos E Participações S.A. in Brazilian Application No. PI 0919466-5 (submitted Nov. 11, 2020).
Decision of Reexamination of Chinese Application No. 201510642287.2 (Aug. 2021).
Report on the Filing or Determination of an Action Regarding a Patent or Trademark re U.S. Pat. No. 10,842,780: *Astellas Pharma Inc.* v. *Apotex Inc. et al.* (C.A. No. 1:21-cv-01141-UNA; filed Aug. 2021).
Report on the Filing or Determination of an Action Regarding a Patent or Trademark re U.S. Pat. Nos. 7,342,117; 7,982,049; 8,835,474; 10,842,780; and RE44,872: *Astellas Pharma Inc.* v. *Alkem Laboratories Ltd.* (C.A. No. 1:21-cv-00992-UNA; filed Jul. 2021).
Administrative Nullity Request by Sandoz AG in Brazilian Patent No. PI 0919466-5 (Dec. 2021).
Administrative Nullity Request by Apsen Farmacêutica S/A in Brazilian Patent No. PI 0919466-5 (Dec. 2021).
Gordon L. Amidon et al., "A Theoretical Basis for a Biopharmaceutic Drug Classification: The Correlation of in Vitro Drug Product Dissolution and in Vivo Bioavailability", 12 Pharm. Res. 413-420 (1995).
Statement of Claim in Application by Unipharm Ltd. for Revocation of Israel Patent No. 212033 (Feb. 2022).
Expert Opinion of Gershon Golomb in Application by Unipharm Ltd. for Revocation of Israel Patent No. 212033 (Feb. 2022).
Kazuhiro Sako et al., "Relationship Between Gelation Rate of Controlled-Release Acetaminophen Tablets Containing Polyethylene Oxide and Colonic Drug Release in Dogs," 13(4) Pharm. Res. 594-598 (1996).
JUSTIA: Tablet Composition with a Prolonged Release of Tamsulosin, pp. 1-18 (May 2007).
Emilio Sacco et al., "Mirabegron: a review of recent data and its prospects in the management of overactive bladder," 4(6) Therap. Adv. Urol. 315-324 (2012).
Decision in European Application No. 04 013 654.1 (Jul. 2011).
Hiroyuki Kojima et al., Extended Release of a Large Amount of Highly Water-Soluble Diltiazem Hydrochloride by Utilizing Counter Polymer in Polyethylene Oxides (PEO)/Polyethylene Glycol (PEG) Matrix Tablets, 70 Eur. J. Pharm. Biopharm. 556-562 (Jun. 2008).
Joseph A. Fix et al., "Controlled-Release Oral Delivery Systems, in Controlled Drug Delivery," 752 ACS Symposium Series, Chapter 2, 14-24 (2000).
Directive 2001/20/EC of the European Parliament and of the Council, pp. L 121/34-L 121/44 (2001).
European Medicines Agency (EMA): Annual Report 2011, pp. 13-14 (2012).
Opinion in *Bayer Schering Pharma AG et al.* v. *Barr Laboratories*, Case 2:05-cv-02308-PGS-ES, pp. 1-96 (2008).
Clinical Trial Agreement: Clinical Trial 178-CL-046, pp. 1, 3-5, 7, 8 (dated 2008).
European Medicines Agency (EMA) Guideline for Good Clinical Practice: ICH Topic E 6 (R1), pp. 1-48 (2002).
Directive 2001/83/EC of the European Parliament and of the Council, pp. 1, 11-15 (2001).
Jennifer Lee et al., "Effects of Food Intake on the Pharmacokinetic Properties of Mirabegron Oral Controlled-Absorption System: A Single-Dose, Randomized, Crossover Study in Healthy Adults," 35(3) Clinical Therapeutics 333-341 (2013).
David Fleisher et al., "Drug Absorption with Food", Ch. 7 in "Handbook of Drug-Nutrient Interactions," Boullata, J.I. et al. (eds), pp. 129-154 (2004).
Clinical Pharmacology and Biopharmaceutic Review(s) of Application No. 202611 Orig1 s000, pp. 1-13 (2012).
Kimberley A. Lentz, "Current Methods for Predicting Human Food Effect," 10(2) The AAPS Journal 282-288 (2008).

(56) References Cited

OTHER PUBLICATIONS

Submission by Hamm&Wittkopp Patentanwälte PartmbB in Opposition to European Patent No. 2 345 410 (May 2022).
Submission by Sandoz AG in Opposition to European Patent No. 2 345 410 (Jun. 2022).
Mark A. Jordi et al., "Gel Permeation Chromatography," Chromatography Techniques, pp. 36-38 (Mar./Apr. 2008).
Comment on Post-Grant Amendments in Taiwanese Patent No. 1478712 (Jul. 2022).
Opposition to Motion for Amendment of Israeli Patent No. 212033 with Expert Opinion of Gershon Golomb (Jun. 2022).
Technical Examination Report in Brazilian Patent No. PI 0919466-5 (Oct. 2022).
Technical Examination Report in Brazilian Patent No. PI 0919466-5 (Nov. 2022).
Application for Revocation in South African Patent No. 2011/02406 (Jan. 2023).
Non-Final Office Action in U.S. Appl. No. 17/114,890 (Jan. 2023).
Summons to Attend Oral Proceedings in European Patent No. 2 345 410 (Sep. 2022).
Takaishi et al., U.S. Appl. No. 18/437,323, filed Feb. 9, 2024.
Takaishi et al., U.S. Appl. No. 18/613,270, filed Mar. 22, 2024.
European Patent Office; Official Communication pursuant to Article 94(3) EPC in European Application No. 09817723.1 dated Dec. 20, 2018.
European Patent Office; Official Communication pursuant to Rule 114(2) EPC in European Application No. 09817723.1 dated Jan. 10, 2019.
Extended Search Report, Oct. 30, 2014, EP application No. 09 81 7723, 5 pages.
Final Office Action dated Jan. 23, 2019 in U.S. Appl. No. 14/584,933.
Final Office Action, May 17, 2013, U.S. Appl. No. 13/073,721.
Final Office Action, Nov. 21., 2013, U.S. Appl. No. 13/073,677.
Ghali, Isis, A D, Examiner at the U.S. Patent and Trademark Office; Final Office Action in U.S. Appl. No. 14/584,933 dated Jul. 18, 2017.
Guidance for Industry: Food-Effect Bioavailability and Fed Bioequivalence Studies, pp. 1-9, 2 (Dec. 2002).
Guideline for Industry: Guideline for Submitting Supporting Documentation for the Manufacture of and Controls for Drug Products, Center for Drugs and Biologics, Food and Drug Administration, pp. 1-17 (Feb. 1987).
Guidelines for the Design and Evaluation of Oral Prolonged Release Dosage Forms, Pharmaceutical Affairs Council, Ministry of Health and Welfare, Japan, (1), No. 5, pp. 1-4 (Mar. 1988).
Gupta et al., Recent Trends in Oral Drug Delivery: A Review, Recent Patents on Drug Delivery & Formulation, 2009, pp. 162-173, vol. 3, Bentham Science Publishers Ltd.
Harry G. Brittain, "Methods for the Characterization of Polymorphs and Solvates," Ch. 6 in Polymorphism in Pharmaceutical Solids, pp. 227-278 (1999).
Hercules Incorporated, "Klucel Hydroxypropylcellulose, Physical and Chemical Properties," Aqualon Division, http://www.brenntagspecialties.comien/downloads/productimulti_market_principals/aqualon/klucel_hpc_booklet.pdf, 2001, 26 pages.
Hiroo Takeda et al., "Role of the β3-Adrenoceptor in Urine Storage in the Rat: Comparison between the Selective β 3-Adrenoceptor Agonist, CL316,243, and Various Smooth Muscle Relaxants," 293 J. Pharmacol. Exp. Ther. 939-945 (2000).
Hiroyasu Ogata, "1. Pharmacokinetics: Absorption," 30 (3) Jpn. J. Clin. Pharmacol. Ther. 617, 619 (May 1999).
Hoffmann Eitle, Letter to European Patent Office responding to Official Action dated Feb. 14, 2017 in European Patent Application No. 11 762 758.9, dated Aug. 2, 2017, 5 pages.
"Hydrates," in Encyclopedia of Pharmaceutical Technology, vol. 7, p. 393 (1993).
Idada Sadao et al. (eds.), "Comprehensive Techniques for Development System of New Formulations, Volume for Bases and Additive," pp. 424-429 (Jul. 1985).

Indonesian Patent Application No. W00201101572, First Office Action mailed Aug. 1, 2018, 4 pages.
Intellectual Property Office of the Philippines; Subsequent Substantive Examination Report; PH Application No. 1/2011/500628; 3 pages; Jan. 11, 2016.
International Search Report of Application No. PCT/JP2009/066742 dated Nov. 10, 2009.
European Patent Office; Third Party Observation—Communication Pursuant to Rule 114(2)EPC; Application No. 09817723.1-1114; dated May 8, 2018.
"Yamanouchi Shaklee Pharma Licenses OCAS Drug Delivery Technology from Yamanouchi Pharmaceutical Co., Ltd.," Pharmaceutical Online, pp. 1-2 (May 1999).
Ishikawa et al., "Preparation of rapidly disintegrating tablet using new types of microcrystalline cellulose (PH-M series) and low-substituted-hydroxypropylcellulose or spherical sugar granules by direct compression method," Chem. Pharm. Bull. 49(2) 134-139, 2001.
Israeli Patent Application No. 212033, First Substantive Examination Report, 4 pages.
Janice J. MacKichan et al., "Pharmacokinetic Considerations for Drug Delivery," Ch. 2 in Gibaldi's Drug Delivery Systems in Pharmaceutical Use, pp. 11-22 (2007).
Japanese Patent Application No. 2010-531838, first Office Action, Oct. 12, 2010, 8 pages.
Japanese Patent Application No. 2010-531838, first Office Action, Dec. 28, 2010, 4 pages.
Jens T. Carstensen, "Preformulation," Ch. 7 in Modern Pharmaceutics 213-237 (1996).
John Haleblian et al., "Pharmaceutical Applications of Polymorphism," 58(8) J. Pharm. Sci 911-929 (Aug. 1969).
K.-E. Andersson, "Overactive Bladder—Pharmacological Aspects," 210 Scand. J. Urol. Nephrol. Suppl. 72-81 (2002).
Kazuhiro Sako, "Formulations and Particle Design: Design of Novel Oral Controlled-Release System (OCAS) for Continuous Drug Absorption," 14(6) Pharm Tech Japan 85-98 (Jun. 1998).
Korean Patent Application No. 10-2011-7009897, Notice of Preliminary Rejection, Mar. 20, 2014, 10 pages.
Korean Patent Application No. 10-2011-7009897, Notice of Final Rejection, Nov. 17, 2014, 6 pages.
Lachman et al., Sustained Release Dosage Forms, The Theory and Practice of Industrial Pharmacy, 3rd Edition, Chapter 14, Aug. 10, 2011, pp. 430-456.
Marilyn N. Martinez et al., "A Mechanistic Approach to Understanding the Factors Affecting Drug Absorption: A Review of Fundamentals," 42 J. Clin. Pharmacol. 620-643 (2002).
Mauger et al., Intrinsic Dissolution Performance Testing of the USP Dissolution Apparatus 2 (Rotating Paddle) Using Modified Salicylic Acid Calibrator Tablets: Proof of Principle, Dissolution Techniques, Aug. 2003, pp. 6-15.
Mexican Institute of Industrial Property; Communication of results of the examination on the merits; PCT Patent Application No. MX/a/2011/003445; Mar. 22, 2017.
Mexican Institute of Intellectual Property; First Office Action from Examiner; MX Application No. MX/a/2011/003445; 7 pages; Mar. 1, 2016.
Michel et al., The Pharmacokinetc Profile of Tamsulosin Oral Controlled Absorption System (OCAS®), 2005, European Urology Supplements, vol. 4, pp. 15-24.
Mino R. Caira, "Crystalline Polymorphism of Organic Compounds," in Topics in Current Chemistry, vol. 198, pp. 163-208 (1999).
Mitsuru Hashida (ed.), "Design and Evaluation of Formulations for Oral Administration," pp. 33, 35, 293-294 (Feb. 1995).
MX Application No. MX/a/2011/003445, Second Office Action dated Sep. 2, 2016, 2 pgs. (English Translation 3 pages).
Nobuyuki Tanaka et al., "β3-Adrenoceptor Agonists for the Treatment of Frequent Urination and Urinary Incontinence: 2-[4-(2-{[(1S,2R)-2-Hydroxy-2-(4-hydroxyphenyl)-1-methylethyl]amino}ethyl)phenoxy]-2-methylpropionic Acid," 9 Bioorgan. Med. Chem. 3265-3271 (2001).
Nobuyuki Tanaka et al., "Discovery of Novel N-Phenylglycine Derivatives as Potent and Selective β3-Adrenoceptor Agonists for

(56) References Cited

OTHER PUBLICATIONS the Treatment of Frequent Urination and Urinary Incontinence," 44 J. Med. Chem. 1436-1445 (Apr. 2001).
Non-Final Office Action in U.S. Appl. No. 14/584,933; dated Jan. 19, 2018.
Non-Final Office Action in U.S. Appl. No. 14/584,933 (Jun. 10, 2020).
Non-Final Office Action in U.S. Appl. No. 14/584,933 dated Nov. 17, 2016, 17 pgs.
Notice of Opposition to a European Patent, Patent No. EP2554168 to Astellas Pharma Inc., Opponent Lederer & Keller Patentanwalte Partnerschaft mbB, Dated Oct. 24, 2018.
Notice of Opposition to a European Patent, Patent No. EP2554168 to Astellas Pharma Inc., Opponent Hexal AG, Dated Oct. 24, 2018.
Notice of Opposition to European Patent No. 2 345 410 by Sandoz AG (Sep. 2021).
English Language Translation of European Application No. 09 817 723.1 (Sep. 2009).
English Language Translation of U.S. Appl. No. 61/101,338 (Sep. 2008).
EU Clinical Trials Register Entry for Study 2005-002256-17 (Retrieved Jun. 2021).
Summary of Results for Laypersons for Study 2005-002256-17 (Feb. 2019).
Synopsis for Study 2005-002256-17 (Apr. 2010).
FDA Clinical Pharmacology and Biopharmaceutics Review for Mirabegron (Mar. 2012).
EU Clinical Trials Register Entry for Study 2007-001451-19 (Retrieved Sep. 2021).
Synopsis for Study 2007-001451-19 (Apr. 2010).
EU Clinical Trials Register Entry for Study 2007-001452-39 (Retrieved Sep. 2021).
Synopsis for Study 2007-001452-39 (Dec. 2010).
Synopsis for Study with Sponsor Code 178-CL-047 (Apr. 2010).
EU Clinical Trials Register Entry for Study 2008-007087-42 (Retrieved Sep. 2021).
Synopsis for Study 2008-007087-42 (Feb. 2011).
Response to Communication Pursuant to Rules 70(2) and 70a(2) EPC in European Application No. 09 817 723.1 (May 2015).
Prescribing Information for MYRBETRIQ™ (mirabegron) (Jun. 2012).
Report on the Deliberation Results for Betanis® Tablets (May-Jun. 2011).
Japanese Prescribing Information for Betanis® Tablets (Jul. 2019).
Judith E. Thompson et al. (eds.), A Practical Guide to Contemporary Pharmacy Practice, 3rd ed., pp. 216-223 (2009).
ClinicalTrials.gov: History of Changes for Study: NCT00940121, Pharmacokinetics of Oral Mirabegron With Different Release Rates Versus Intravenous (IV) Mirabegron, U.S. National Library of Medicine (Retrieved Jul. 2021).
Karl-Erik Andersson, LUTS Treatment: Future Treatment Options, 26 Neurourol. Urodyn. 934-947 (2007).
Deborah J. Lightner et al., Diagnosis and Treatment of Overactive Bladder (Non-Neurogenic) in Adults: AUA/SUFU Guideline Amendment 2019, 202 J. Urol. 558-563 (2019).
Prescribing Information for Toviaz™ (Apr. 2008).
Leon Shargel et al. (eds.), "Applied Biopharmaceutics & Pharmacokinetics," 5th ed., pp. 1-19, 161-217, 453-499, 515-552 (2005).
Prescribing Information for Amrix® (Apr. 2019).
Guidance for Industry: M9 Biopharmaceutics Classification System-Based Biowaivers, pp. 1-16 (May 2021).
L. Kalantzi, et al., "Biowaiver Monographs for Immediate Release Solid Oral Dosage Forms: Acetaminophen (paracetamol)," 95(1) J. Pharm. Sci. 4-14 (2006).
USP Monographs: Loratadine Chewable Tablets (Feb. 2024).
USP Monographs: Loratadine Tablets (Feb. 2024).
USP Monographs: Loratadine Orally Disintegrating Tablets (Feb. 2024).
Robert E. Notari, Biopharmaceutics and Clinical Pharmacokinetics, 4 ed., Ch. 5, pp. 130-170 (1987).
Prescribing Information for Zmax® (Nov. 2021).
Anthony R. DiSantro, "Bioavailability and Bioequivalence Testing," in Remington: Practice of the Science and Pharmacy, 19th ed., Ch. 35, pp. 605-612 (1995).
Edward M. Rudnic et al., "Oral Solid Dosage Form," in Remington: The Science and Practice of Pharmacy, 21st ed., Ch. 45, pp. 889-928 (2005).
Stuart C. Porter, "Coating of Pharmaceutical Dosage Form," in Remington: The Science and Practice of Pharmacy, 21st ed., Ch. 46, pp. 929-938 (2005).
Guidance for Industry: Immediate Release Solid Oral Dosage Forms, pp. 1-26, A-1 (Nov. 1995).
Guidance for Industry: SUPAC-MR: Modified Release Solid Oral Dosage Forms, pp. 1-36, A-1-A6; B1-B6 (Sep. 1997).
Prescribing Information for Namenda XR® (Nov. 2019).
Prescribing Information for Zanaflex Capsules™ (tizanidine hydrochloride) and Zanaflex® Tablets (tizanidine hydrochloride) (Jul. 2006).
Medscape: Tamsulosin (Rx) Pharmacology Extract (ND).
Joseph P. O'Shea et al., "Food for Thought: Formulating Away the Food Effect—a PEARRL Review," 71 J. Pharm. Pharmaco. 510-535 (2019).
Gunilla Englund et al., "Regional Levels of Drug Transporters Along the Human Intestinal Tract: Co-Expression of ABC and SLC Transporters and Comparison with Caco-2 Cells," 29 Eur. J. Pharm. Sci. 269-277 (May 2006).
Response to Communication Pursuant to Article 94(3) EPC in European Application No. 09 817 723.1 (Mar. 2020).
Hassan Y. Aboul-Enein et al., "Tamsulosin Dissolution from Pharmaceutical Dosage Forms Using an Automated HPLC System," 26(7) J. Liquid Chromatogr. & Related Technol. 1109-1116 (2003).
Xiong Zhang et al., "Development of a Tamsulosin Hydrochloride Controlled-Release Capsule Consisting of Two Different Coated Pellets," 35 Drug Dev. Ind. Pharm. 26-33 (2009).
Emilio Sacco et al., "Mirabegron, a Novel, Non-Antimuscarinic Drug for the Overactive Bladder: An Up-To-Dated Review," 2(4) World J. Obstet. Gynecol. 65-73 (Nov. 2013).
Decision Rejecting the Opposition of European Patent No. 2 345 410, with Minutes of the Oral Proceedings (Mar. 2024).
Cherng-Ju Kim, "Drug Release from Compressed Hydrophilic POLYOX-WSR Tablets," 84(3) J. Pharm. Sci. 303-306 (Mar. 1995).
Martin C. Michel et al., "Comparison of Vascular α1-Adrenoceptor Antagonism of Tamsulosin in Oral Controlled Absorption System (OCAS) and Modified Release (MR) Formulations," 4 Eur. Urol. Supp. 45-52 (2005).
Petition re OCAS Trademark Registration (dated Aug. 2006).
OCAS Trademark Registration (Apr. 2008).
Kazuhiro Sako et al., "Influence of Physical Factors in Gastrointestinal Tract on Acetaminophen Release from Controlled-Release Tablets in Fasted Dogs," 137 Int. J. Pharm. 225-232 (1996).
H.N.E. Stevens et al., "Behaviour and Transit of Tamuslosin Oral Controlled Absorption System in the Gastrointestinal Tract," 22(12) Current Med. Res. Op. 2323-2328 (2006).
Prescribing Information for Flomax® (tamsulosin hydrochloride) Capsules, 0.4 mg (2006).
S. Kiortsis et al., "Drug Release from Tableted Wet Granulations Comprising Cellulosic (HPMC or HPC) and Hydrophobic Component," 59 Eur. J. Pharm. Biopharm. 73-83 (2005).
Gurvinder Singh Rekhi et al., "Identification of Critical Formulation and Processing Variables for Metoprolol Tartrate Extended-Release (ER) Matrix Tablets," 59 J. Controlled Release 327-342 (1999).
K.V. Ranga Rao et al., "Influence of Molecular Size and Water Solubility of the Solute on its Release from Swelling and Erosion Controlled Polymeric Matrices," 12 J. Controlled Release 133-141 (1990).
C. Chapple, et al., "Dose-Ranging Study of Once-Daily Mirabegron (YM178), A Novel Selective β3-Adrenoceptor Agonist, in Patients with Overactive Bladder (OAB)," 9(2) Eur. Urol. Suppl. 249 (2010).
ClinicalTrials.gov, History of Changes for Study: NCT00688688, "Study to Test the Long Term Safety and Efficacy of the Beta-3 Agonist Mirabegron (YM178) in Patients With Symptoms of Overactive Bladder (TAURUS)," U.S. National Library of Medicine (Nov. 2017).

(56) References Cited

OTHER PUBLICATIONS

E.M. van Gelderen, et al., "An Exploratory Comparison of the Single Dose Pharmacokinetcs of the β3-Adrenoceptor Agonist Mirabegron in Healthy CYP2D6 Poor and Extensive Metabolizers," 85 Clin. Pharm. & Therapeutics S88 (Feb. 2009).
Technical Data: Polyox Water-Soluble Resins, Dow Chemical Brochure (2004).
Prescribing Information for Paxil® (Jun. 2007).
Prescribing Information for Paxil CR® (Jun. 2007).
Haesun Park et al., "Physico-Chemical Properties of Water-Insoluble Polymers Important to Mucin/Epithelial Adhesion," 2 J. Controlled Release 47-57 (1985).
Lubrizol Technical Data Sheet: Molecular Weight of Carbopol® and Pemulen® Polymers (2007).
Lubrizol Pharmaceutical Bulletin: Thickening Properties (2008).
Sarfaraz K. Niazi ed., Handbook of Pharmaceutical Manufacturing Formulations Compressed Solid Formulations, vol. 1, pp. 3-296 (2004).
Sarfaraz K. Niazi ed., Handbook of Pharmaceutical Manufacturing Formulations Compressed Solid Formulations, vol. 2, pp. 3-203 (2004).
Jian-Hwa Guo, "Carbopol® Polymers for Pharmaceutical Drug Delivery Applications," 3(6) Drug Delivery Technol. 32-36 (2003).
Thomas Carl Ward, "Molecular Weight and Molecular Weight Distributions in Synthetic Polymers," 58 J. Chem. Educ. 867-879 (1981).
JordiLabs, LLC: Molecular Weight, pp. 1-6 (2021) (https://jordilabs.com/wpcontent/uploads/2017/02/White-Paper-Mw-Averages-Explanation.pdf).
Divya Tewari et al., "Impact of Molecular Weight and Molecular Weight Distribution of Hypromellose in Reducing Drug Release Variability from Erosion Dependent Matrix Systems," Ashland Pharm. Tech. Rep. 1-4 (2010).
Gurjit S. Bajwa et al., "Microstructural Imaging of Early Gel Layer Formation in HPMC Matrices," 95(10) J. Pharm. Scis. 2145-2157 (Oct. 2006).
Richard A. Gemeinhart et al., Effect of Compression on Fast Swelling of Poly(acrylamide-co-acrylic acid) Superporous Hydrogels, 55 J. Biomed. Mater. Res. 54-62 (2001).
Nikolaus A. Peppas ed., Hydrogels in Medicine and Pharmacy, vol. II, pp. 1-171 (1987).
Annick Ludwig, "The Use of Mucoadhesive Polymers in Ocular Drug Delivery," 57 Adv. Drug Delivery Rev. 1595-1639 (2005).
Byeongmoon Jeong et al., "Thermosensitive sol-gel Reversible Hydrogels," 54 Adv. Drug Delivery Rev. 37-51 (2002).
Takashi Miyata et al., "Biomolecule-Sensitive Hydrogels," 54 Adv. Drug Delivery Rev. 79-98 (2002).
Allan S. Hoffman, "Hydrogels for Biomedical Applications," 54 Adv. Drug Delivery Rev. 3-12 (2002).
H. Omidian et al., Swelling Agents and Devices in oral Drug Delivery, 18(2) J. Drug Del. Sci. Tech. 83-93 (2008).
Thomas Dürig et al., "Mechanistic Evaluation of Binary Effects of Magnesium Stearate and Talc as Dissolution Retardants at 85% Drug Loading in an Experimental Extended-Release Formulation," 86(10) J. Pharm. Sci. 1092-1098 (1997).
James L. Ford et al., "Importance of Drug Type, Tablet Shape and Added Diluents on Drug Release Kinetics from Hydroxypropylmethylcellulose Matrix Tablets," 40 Int. J. Pharm. 223-234 (1987).
Nelly Fransén et al., "Physiochemical Interactions Between Drugs and Superdisintegrants," 60 J. Pharm. Pharmacol. 1583-1589 (2008).
Yuuki Kasashima et al., "Oral Sustained Release of a Hydrophilic Drug Using the Lauryl Sulfate Salt/Complex," 64(9) Chem. Pharm. Bull. 1304-1309 (2016).
Lubrizol Carbopol Technical Report: Carbopol® Polymers Overview, pp. 1-41 (2008).
Steven H. Neau et al., "Fabrication and Characterization of Extruded and Spheronized Beads Containing Carbopol® 974P, NF Resin," 131 Int. J. Pharm. 47-55 (1996).

Robert O. Williams III et al., "Investigation of Excipient Type and Level on Drug Release from Controlled Release Tablets Containing HPMC," 7(2) Pharm. Dev. & Tech. 181-193 (2002).
Leon Lachman et al. eds., The Theory and Practice of Industrial Pharmacy, pp. 221-222 (1986).
Sung-Hyun Park et al., "Preparation of an Extended-Release Matrix Tablet Using Chitosan/Carbopol Interpolymer Complex," 347 Int. J. Pharm. 39-44 (2008).
Friedlieb Pfannkuch et al., "Biological Effects of the Drug Salt Form," in Handbook of Pharmaceutical Salts: Properties, Selection, and Use (P. Heinrich Stahl et al. eds.), pp. 117-134 (2002).
Abu T. M. Serajuddin et al., "Salt-Selection Strategies," in Handbook of Pharmaceutical Salts: Properties, Selection, and Use (P. Heinrich Stahl et al. eds.), pp. 135-160 (2002).
Michael J. Bowker, "A Procedure for Salt Selection and Optimization," in Handbook of Pharmaceutical Salts: Properties, Selection, and Use (P. Heinrich Stahl et al. eds.), pp. 161-189 (2002).
Camille G. Wermuth et al., Selected Procedures for the Preparation of Pharmaceutically Acceptable Salts, in Handbook of Pharmaceutical Salts: Properties, Selection, and Use (P. Heinrich Stahl et al. eds.), pp. 249-263 (2002).
Abu T.M. Serajuddin, "Salt Formation to Improve Drug Solubility," 59 Adv. Drug Delivery Rev. 603-616 (2007).
P. Heinrich Stahl, Appendix, in Handbook of Pharmaceutical Salts: Properties, Selection, and Use (P. Heinrich Stahl et al. eds.), pp. 329-350 (2008).
M. T. Rosenberg et al., "A Practical Guide to the Evaluation and Treatment of Male Lower Urinary Tract Symptoms in the Primary Care Setting," 61(9) Int'l. J. Clinical Prac. 1535-1546 (Sep. 2007).
Karl-Erik Andersson et al., "Pharmacologic Management of Lower Urinary Tract Storage and Emptying Failure," in Campbell-Walsh Urology (Alan J. Wein et al. (eds.)), pp. 1836-1874e.23 (2016).
"<711> Dissolution" in USP30-NF25, vol. 1; The United States Pharmacopeial Convention: Rockville, pp. 277-284 (May 2007).
A. Dokoumetzidis et al., "IVIVC of Controlled Release Formulations: Physiological—Dynamical Reasons for Their Failure," 129 J. Control. Release 76 (2008).
Amendment submitted on May 30, 2012 by Applicant in U.S. Appl. No. 12/568,313.
Amendment submitted on Aug. 26, 2013 by Applicant in U.S. Appl. No. 12/568,313.
Anderson, Karl-Erik, Prospective Pharmacologic Therapies for the Overactive Bladder, Therapeutic Advances in Urology, 2009, 1(2) 71-83.
Andersson et al., Pharmacological Treatment of Overactive Bladder: Report from the International Consultation on Incontinence, Current Opinion in Urology, 2009. pp. 380-394, vol. 19, Wolfers Klower Health.
Anlage A with Translation of the evidence during Opposition proceeding from opponent Notice of Opposition from STADA Arzneimittel AG dated Oct. 24, 2018 (89 pages) See #33 below.
Artur Burger, "The Relevance of Polymorphism," in Topics in Pharmaceutical Sciences 1983, pp. 347-358 (1983).
Australian Patent Application No. 2009300752, Examination Report, Dec. 14, 2012, 11 pages.
Benner et al., "Patent-reported reasons for discontinuing overactive bladder medication"; Journal Complication; 2009, BJU International; 105; 1276-1282.
Betmiga Tablets—Annex I, Summary of Product Characteristics: Dec. 2012.
Bikiaris et al., New Aspects in Sustained Drug Release Formulations, Recent Patents on Drug Delivery & Formulation, 2007, pp. 201-213, vol. 1, No. 3, Bentham Science Publishers Ltd., Greece.
Bruno C. Hancock et al., "Characteristics and Significance of the Amorphous State in Pharmaceutical Systems," 86(1) J. Pharm. Sci. 1-12 (Jan. 1997).
Canadian Patent Application No. 2,740,342, Office Action, Jun. 3, 2013, 3 pages.
Canadian Patent Application No. 2,740,342, Second Office Action, Feb. 14, 2014, 2 pages.
Center for Drug Development Assistance, National Institute of Food and Drug Saftey Evaluation 11-1470550-000003-08, Dec. 2009, 121 pages and 5 pages English Translation, Korea.

(56) References Cited

OTHER PUBLICATIONS

Center for Drug Evaluation and Research, Application No. 202611orig1s000, Clinical Pharmacology and Biopharmaceutics Review(s)—Mirabegron, 218 pages (Mar. 2012).
Chapple, Christopher R., The Development of the Oral Controlled Absorption System (OCAS®): A New Improved Formulation of Tamsulosin, European Urology Supplements, 2005, pp. 1-4, vol. D4, Elsevier B.V., UK.
Chapple et al., "Add-on" Tolterodine Extended Release Improves Overactive Bladder Symptoms in Men Receiving Alpha-Blocker Therapy, Eur Urol Suppl 2008; 7(3): 239, Abstract 674.
Chinese Patent Application No. 200980138691.9, Decision on Rejection, Feb. 14, 2014, 5 pages.
Chinese Patent Application No. 200980138691.9, first Office Action, Jun. 18, 2013, 14 pages.
Christer Tannergren et al., "Toward an Increased Understanding of the Barriers to Colonic Drug Absorption in Humans: Implications for Early Controlled Release Candidate Assessment," 6(1) Mol. Pharmaceutics 60-73 (Feb. 2009).
ClinicalTrials.gov, History of Changes for Study: NCT00662909, Study to Test the Efficacy and Safety of the beta-3 Agonist YM178 in Patients with Symptoms of Overactive Bladder, U.S. National Library of Medicine, Nov. 2017, 8 pages.
ClinicalTrials.gov, Pharmacokinetics of Oral Mirabegron with Different Release Rates Verses Intravenous (IV) Mirabegron, U.S. National Library of Medicine, Jul. 2013, 6 pages.
clinicaltrials.gov, History of Changes for Study: NCT00912964, A Study. to Test the Efficacy and Safety of the Beta-3 Agonist YM178 in Subjects with Symptoms of Overactive Bladder, U.S. National Library of Medicine, Nov. 2017, 8 pages.
clinicaltrials.gov, History of Changes for Study: NCT00689104, Study to Test the Efficacy and Safety of the Beta-3 Agonist YM178 in Subjects with Symptoms of Overactive Bladder, U.S. National Library of Medicine, Nov. 2017, 8 pages.
clinicaltrials.gov, History of Changes for Study: NCT00940121, Pharmacokinetics of Oral Mirabegron With Different Release Rates Versus Intravenous (IV) Mirabegron, U.S. National Library of Medicine, Jul. 2013, 8 pages.
clinicaltrials.gov, History of Changes for Study: NCT00965926, A Study to Investigate the Food Effect on the Pharmacokinetics of YM178 in Healthy, Non-elderly Volunteers, U.S. National Library of Medicine, Jul. 2013, 6 pages.
clinicaltrials.gov, History of Changes for Study: NCT00939757, Study of the Effect of Food on the Pharmacokinetics of Mirabegron, U.S. National Library of Medicine, Jul. 2013, 6 pages.
"Colonic Drug Absorption and Metabolism," Bieck ed., pp. 21-22 (1993).
Communication pursuant to Article 94(3) EPC in European Application No. 09817723.1 (Sep. 2019).
Communication Pursuant to Art. 94(3) EPC in European Application No. 09817723.1 (Apr. 2020).
Controller of Patents, Indian Patent Office; Examination Report; May 29, 2017; Application No. 2738/CHENP/2011.
D'Souza et al., "Persistence, Adherence, and Switch Rates Among Extended-Release and Immediate-Release Over Active Bladder Medications in a Regional Managed Care Plan," 14(3) JMCP 291-301 (Apr. 2008).
Daewoong Pharmaceutical Co., LTD.; Petitioner's Brief: 2017 Dang 473 Patent Invalidation Action, Feb. 21, 2017.
Daniel S. Elliott et al., "Medical Management of Overactive Bladder," 76(4) Mayo Clin Proc. 353-355 (Apr. 2001).
David Fleisher et al., "Drug, Meal and Formulation Interactions Influencing Drug Absorption After Oral Administration," 36(3) Clin. Pharmacokinet. 233-254 (Mar. 1999).
David P. Benziger et al., "Differential Effects of Food on the Bioavailability of Controlled-Release Oxycodone Tablets and Immediate-Release Oxycodone Solution," 85(4) J. Pharm. Sci. 407-410 (1996).
Decision in Oppositions and Oral Proceeding Minutes in European Patent No. 2 554 168 B1 (Mar. 2, 2020).
Decision of Rejection in Chinese Application No. 201510642287.2 (Nov. 2019).
Decision of the Rejection, Jul. 3, 2015, CN Patent Application No. 200980138691.9, 43 pages.
Dharmesh H. Doshi, "Oral Delivery Systems," Ch. 3 in Gibaldi's Drug Delivery Systems in Pharmaceutical Use, pp. 23-41 (2007).
Donna J. Sellers et al., "Potential therapeutic targets for treatment of overactive bladder," 19 World J. Ural. 307-311 (2001).
Dressman, et al., Oral Drug Absorption Prediction and Assessment, Drugs and the Pharmaceutical Sciences, 2000, Pages Preface, 183-228, Marcel Dekker, Inc., New York, USA.
Drug Data Report, 21(7), p. 619.
European Medicines Agency—Assessment Report; Oct. 2012.
European Patent Office; Communication Pursuant to Article 94(3) EPC dated Feb. 14, 2017 in Application No. 11 762 748.9.
European Patent Office; Communication Pursuant to Article 114(2) EPC dated Feb. 2, 2017 in Application 11762748.9.
European Patent Office; First Official Communication pursuant to Article 94(3) EPC; Application No. 09817723.1-1114; dated Apr. 30, 2018.

PHARMACEUTICAL COMPOSITION FOR MODIFIED RELEASE

CROSS-REFERENCE TO RELATED APPLICATIONS

The present application is a continuation of U.S. application Ser. No. 18/437,323, filed Feb. 9, 2024, which is a continuation of U.S. application Ser. No. 18/339,513, filed Jun. 22, 2023, now abandoned, which is a continuation of U.S. application Ser. No. 17/114,890, filed Dec. 8, 2020, now U.S. Pat. No. 11,707,451, which is a continuation of U.S. application Ser. No. 14/584,933, filed Dec. 29, 2014, now abandoned, which is a divisional of U.S. application Ser. No. 13/073,721, filed Mar. 28, 2011, now abandoned, which application claims the benefit of U.S. Provisional Application No. 61/318,569, filed Mar. 29, 2010, and the disclosure of each such application is hereby incorporated by reference in its entirety for all purposes.

TECHNICAL FIELD

The present invention relates to a pharmaceutical composition for modified release capable of reducing food effects observed in conventional tablets, by combining an active ingredient with one or more excipients and controlling a releasing rate of the active ingredient.

More particularly, the present invention relates to a pharmaceutical composition for modified release comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, in which a maximum blood drug concentration (Cmax) in a fasted state is controlled to be a specific value or less by controlling a releasing rate of the active ingredient.

BACKGROUND ART (R)-2-(2-aminothiazol-4-yl)-4'-[2-[(2-hydroxy-2-phenylethyl)amino]ethyl]acetic acid anilide has been created by Astellas Pharma Inc., and it has been reported that this compound has not only both an activity of promoting insulin secretion and an activity of enhancing insulin sensitivity, but also an antiobestic activity and an antihyperlipemic activity based on an activity of selectively stimulating a β3 receptor, and is useful in treating diabetes (see, for example, patent literature 1).

Further, it has been reported that the compound can be used as a therapeutic agent for overactive bladder, such as overactive bladder accompanied by prostatic hyperplasia, or overactive bladder accompanied by urinary urgency, urinary incontinence, and urinary frequency (see, for example, patent literature 2).

A clinical trial of (R)-2-(2-aminothiazol-4-yl)-4'-[2-[(2-hydroxy-2-phenylethyl)amino]ethyl]acetic acid anilide in the form of conventional formulations revealed that pharmacokinetic data unexpectedly varied according to the presence or absence of the intake of food. For example, the rate of decrease of Cmax in a fed state was 67%, and the rate of decrease of AUC in the fed state was 47%, in comparison with those in a fasted state. In this case, Cmax in the fasted state was three times higher than that in the fed state. These problems are considered to be raised by, for example, the changes in pharmacokinetics caused by food, and therefore, the development of a formulation capable of avoiding the effects by food intake is desired.

As a technique of preparing a formulation for modified release, a hydrogel sustained release tablet containing an additive which ensures penetration of water into the tablet, and a hydrogel-forming polymer is disclosed (see, for example, patent literature 3).

However, patent literature 3 does not refer to (R)-2-(2-aminothiazol-4-yl)-4'-[2-[(2-hydroxy-2-phenylethyl)amino]ethyl]acetic acid anilide, and further improvements are needed to produce a pharmaceutical composition.

CITATION LIST

Patent Literature

[patent literature 1] International Publication No. WO 99/20607 (Example 41)
[patent literature 2] International Publication No. WO 2004/041276
[patent literature 3] International Publication No. WO 94/06414

SUMMARY OF INVENTION

Technical Problem

An object of the present invention is to provide a pharmaceutical composition for modified release comprising (R)-2-(2-aminothiazol-4-yl)-4'-[2-[(2-hydroxy-2-phenylethyl)amino]ethyl]acetic acid anilide or a pharmaceutically acceptable salt thereof, in which the pharmaceutical composition has efficacy the same as or higher than those of conventional formulations and has no limitations on food intake.

Solution to Problem

The elimination half-life ($T_{1/2}$) of (R)-2-(2-aminothiazol-4-yl)-4'-[2-[(2-hydroxy-2-phenylethyl)amino]ethyl]acetic acid anilide is long (approximately 18 to 24 hours), and thus, a formulation thereof for modified release is not necessarily needed to maintain its blood level. Taking into consideration the results of the clinical trial described above, the present inventors conducted intensive studies to design the formulation by paying attention to the control of a release rate of the drug from a formulation to the extent that the release is not affected by food intake or the like, rather than the addition of release control.

On the basis of blood concentration profiles (in a fasted state/after the intake of food) after administration of a conventional formulation (immediate release formulation), the absorption rate of the drug in a fed state was calculated by a deconvolution method to predict continuous absorption for about 4 hours. The present inventors considered from this result that a formulation capable of continuous drug release for 4 hours or more would be able to reduce the effects by food, because the drug release from the formulation would become the rate-limiting step for absorption.

The present inventors carried out a clinical trial in human using three types of formulations in which the release rate of the drug was controlled, and found that all formulations could reduce the effects by food, to complete the present invention.

It is generally known that the retention time in the stomach and the release rate of formulations for modified release vary according to the presence or absence of food intake, and as a result, there is a possibility that blood concentration profiles is changed. However, surprisingly, when using this formulation, the change of the blood concentration profiles was small in the presence or absence of food intake.

The present invention is characterized by providing a pharmaceutical composition for modified release capable of reducing the effects by food, which was observed in formulations (conventional tablets) in which the releasing rate of the active ingredient was not controlled, by controlling the pharmacokinetics profile of the active ingredient. Furthermore, the present invention provides a pharmaceutical composition for modified release capable of preventing the occurrence of adverse effects that it can be used to anticipate, such as an increase in heart rate by controlling $C_{max}$ in a fasted state to a specific value or less.

The present invention provides:

[1] a pharmaceutical composition for modified release comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a maximum blood drug concentration (Cmax) when administered in a fasted state is 400 ng/ml or less,

[2] the pharmaceutical composition for modified release of [1], wherein the maximum blood drug concentration (Cmax) when administered in a fasted state is 300 ng/ml or less,

[3] a pharmaceutical composition for modified release, comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of a maximum blood drug concentration (Cmax) thereof in comparison with a Cmax of a conventional formulation is 10% or more,

[4] a pharmaceutical composition for modified release, comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of a maximum blood drug concentration (Cmax) when administered after eating a meal, in comparison with a Cmax when administered in a fasted state, is 10% or more,

[5] a pharmaceutical composition for modified release, comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of an area under a blood drug concentration versus time curve (AUC) when administered after eating a meal, in comparison with an AUC when administered in a fasted state, is 10% or more,

[6] a pharmaceutical composition for modified release comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a dissolution rate of the drug from the composition is less than 85% after 30 minutes from the beginning of a dissolution test,

[7] the pharmaceutical composition for modified release of [6], wherein a dissolution rate is 75% or less after 1.5 hours from the beginning of the dissolution test,

[8] the pharmaceutical composition for modified release of [6], wherein the dissolution rate is 75% or less after 1.5 hours from the beginning the dissolution test, and a dissolution rate is 75% to 100% after 7 hours from the beginning of the dissolution test,

[9] the pharmaceutical composition for modified release of any one of [1] to [8], which is selected from the group consisting of a sustained release hydrogel-forming formulation, a multi-layered formulation consisting of a drug core and a release-controlling layer which are geometrically arranged, a gel formulation in which a plurality of gums is combined, an osmotic pump type formulation, a formulation utilizing a swelling polymer, a matrix formulation utilizing a water-soluble polymer, a modified release formulation with a coating membrane, and a matrix formulation utilizing an insoluble polymer,

[10] a method of reducing an effect of food intake, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a maximum blood drug concentration (Cmax) when administered in a fasted state is 400 ng/mL or less,

[11] the method of reducing an effect of food intake of [10], wherein the maximum blood drug concentration (Cmax) when administered in a fasted state is 300 ng/mL or less,

[12] a method of reducing an effect of food intake, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of a maximum blood drug concentration (Cmax) thereof in comparison with a Cmax of a conventional formulation is 10% or more,

[13] a method of reducing an effect of food intake, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of a maximum blood drug concentration (Cmax) when administered after eating a meal, in comparison with a Cmax when administered in a fasted state, is 10% or more,

[14] a method of reducing an effect of food intake, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of an area under a blood drug concentration versus time curve (AUC) when administered after eating a meal, in comparison with an AUC when administered in a fasted state, is 10% or more,

[15] a method of reducing an effect of food intake, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a dissolution rate of the drug from the composition is less than 85% after 30 minutes from the beginning of a dissolution test,

[16] the method of reducing an effect of food intake of [15], wherein a dissolution rate is 75% or less after 1.5 hours from the beginning of the dissolution test,

[17] the method of reducing an effect of food intake of [15], wherein the dissolution rate is 75% or less after 1.5 hours from the beginning the dissolution test, and a dissolution rate is 75% to 100% after 7 hours from the beginning of the dissolution test,

[18] the method of reducing an effect of food intake of any one of [10] to [17], wherein the pharmaceutical composition is selected from the group consisting of a sustained release hydrogel-forming formulation, a multi-layered formulation consisting of a drug core and a release-controlling layer which are geometrically arranged, a gel formulation in which a plurality of gums is combined, an osmotic pump type formulation, a formulation utilizing a swelling polymer, a matrix formulation utilizing a water-soluble polymer, a modified release formulation with a coating membrane, and a matrix formulation utilizing an insoluble polymer,

[19] a method of inhibiting an increase in heart rate, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a maximum blood drug concentration (Cmax) when administered in a fasted state is 400 ng/ml or less,

[20] the method of inhibiting an increase in heart rate of [19], wherein the maximum blood drug concentration (Cmax) when administered in a fasted state is 300 ng/mL or less, a method of inhibiting an increase in heart rate,

[21] comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of a maximum blood drug concentration (Cmax) thereof in comparison with a Cmax of a conventional formulation is 10% or more,

[22] a method of inhibiting an increase in heart rate, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of a maximum blood drug concentration (Cmax) when administered after eating a meal, in comparison with a Cmax when administered in a fasted state, is 10% or more,

[23] a method of inhibiting an increase in heart rate, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a rate of decrease of an area under a blood drug concentration versus time curve (AUC) when administered after eating a meal, in comparison with an AUC when administered in a fasted state, is 10% or more,

[24] a method of inhibiting an increase in heart rate, comprising the step of administering a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, and a carrier for a sustained release pharmaceutical composition, wherein a dissolution rate of the drug from the composition is less than 85% after 30 minutes from the beginning of a dissolution test,

[25] the method of inhibiting an increase in heart rate of [24], a dissolution rate is 75% or less after 1.5 hours from the beginning of the dissolution test,

[26] the method of inhibiting an increase in heart rate of [24], wherein the dissolution rate is 75% or less after 1.5 hours from the beginning the dissolution test, and a dissolution rate is 75% to 100% after 7 hours from the beginning of the dissolution test, and

[27] the method of inhibiting an increase in heart rate of any one of [19] to [26], wherein the pharmaceutical composition is selected from the group consisting of a sustained release hydrogel-forming formulation, a multi-layered formulation consisting of a drug core and a release-controlling layer which are geometrically arranged, a gel formulation in which a plurality of gums is combined, an osmotic pump type formulation, a formulation utilizing a swelling polymer, a matrix formulation utilizing a water-soluble polymer, a modified release formulation with a coating membrane, and a matrix formulation utilizing an insoluble polymer.

As formulation techniques for reducing or avoiding the changes in pharmacokinetics such as AUC or Cmax accompanied by food intake, a formulation technique concerning a sustained-release pharmaceutical composition containing tamsulosin hydrochloride is disclosed (see Japanese Unexamined Patent Publication (Kokai) No. 2005-162736 and Japanese Unexamined Patent Publication (Kokai) No. 2005-162737). This formulation technique is limited to tamsulosin, and applied to a formulation containing the drug at a low dose (0.4 mg per unit formulation). This formulation enables to control the release of tamsulosin therefrom by being mainly composed of a sustained-release base. By contrast, the pharmaceutical composition contains the drug at a high dose (i.e., high content per unit formulation), and it is considered difficult to control the release rate of the drug from a formulation containing the sustained-release base at a low content, and therefore, the present invention is technically quite different from the formulation disclosed in these references.

Advantageous Effects of Invention

According to the present invention, a pharmaceutical composition for modified release capable of reducing the food effects can be provided. Further, because the pharmaceutical composition for modified release of the present invention can control $C_{max}$ in a fasted state to a specific value or less, $C_{max}$ can be reduced to the specific value or less even at a single dose per day, and adverse effects, such as an increase in heart rate, can be anticipated and prevented in advance.

DESCRIPTION OF EMBODIMENTS

Figure 1:
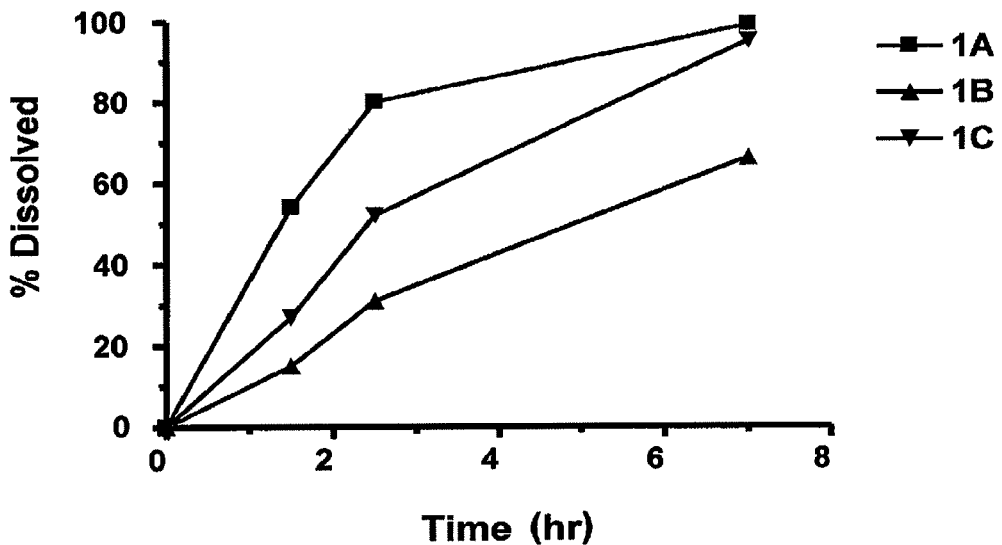
FIG. 1 is a graph showing the drug release property from each of the formulations prepared in Examples 1A to 1C in Experimental Example 1.

The pharmaceutical composition for modified release of the present invention will be explained hereinafter.

The term "immediate release formulation (conventional formulation)" as used herein means a formulation in which the dissolution rate of the drug from the formulation is 85% or more after 30 minutes from the beginning a dissolution test, which is carried out in accordance with a dissolution test (paddle method) described in the United States Pharmacopoeia under the conditions that 900 mL of an appropriate test fluid (such as a USP buffer, pH 6.8) is used and the paddle rotation speed is 100 rpm. Alternatively, the term means a formulation in which the dissolution rate of the drug from the formulation is 85% or more after 30 minutes from the beginning a dissolution test, which is carried out in accordance with a dissolution test, method 2 described in the Japanese Pharmacopoeia under the conditions that 900 mL of an appropriate test fluid (such as a Mc. Ilvain buffer, pH 6.8) is used and the paddle rotation speed is 50 rpm. Alternatively, the term means a formulation in which the dissolution rate of the drug from the formulation is 85% or more after 30 minutes from the beginning a dissolution test, which is carried out in accordance with a dissolution test, method 2 (paddle method) described in the Japanese Pharmacopoeia under the conditions that 900 mL of a USP phosphate buffer (pH 6.8) is used as a test fluid and the paddle rotation speed is 200 rpm.

The term "pharmaceutical composition for modified release" as used herein means a formulation in which the Cmax when administered in a fasted state is 400 ng/ml or less, and the drug release is controlled to the extent that the effects by food are reduced and/or to the extent that the Cmax can be controlled to the specific value or less even at a single dose per day.

The wording "the effects by food are reduced" as used herein means, for example, a reduction by 10% or more, a reduction by 20% or more in another embodiment, and a reduction by 30% or more in still another embodiment, in comparison with Cmax of a conventional formulation. Alternatively, the term means, for example, a reduction by 10% or more with respect to the rates of decrease of Cmax and AUC in administration after food intake, in comparison with Cmax and AUC in administration in the fasted state, a reduction by 20% or more in another embodiment, and a reduction by 30% or more in still another embodiment.

The rates of decrease of Cmax and AUC are calculated by the following equations:

$$Rd(Cmax) = [Cmax(FS) - Cmax(FI)] \times 100 / Cmax(FS)$$

$$Rd(AUC) = [AUC(FS) - AUC(FI)] \times 100 / AUC(FS)$$

Rd (Cmax): Rate of decrease of Cmax (%)
Cmax (FS): Cmax in administration in the fasted state
Cmax (FI): Cmax in administration after food intake
Rd (AUC): Rate of decrease of AUC (%)
AUC (FS): AUC in administration in the fasted state
AUC (FI): AUC in administration after food intake The term "formulation in which the effects by food are reduced" as used herein means a formulation in which the dissolution rate of the drug from the formulation is less than 85% after 30 minutes from the beginning a dissolution test, which is carried out under the above conditions. In another embodiment, it means a formulation in which the dissolution rate of the drug from the formulation is 75% or less after 1.5 hours from the beginning a dissolution test. In still another embodiment, it means a formulation in which the dissolution rate of the drug from the formulation is 75% or less after 1.5 hours and 75% to 100% after 7 hours from the beginning a dissolution test.

The term "formulation in which the effects by food are reduced" as used herein means a formulation in which the Cmax when administered in a fasted state is 400 ng/ml or less (corresponding to an increase in heart rate of 16 bpm or less). In another embodiment, it means a formulation in which the Cmax when administered in a fasted state is 300 ng/mL or less (corresponding to an increase in heart rate of 13 bpm or less). In still another embodiment, it means a formulation in which the Cmax when administered in a fasted state is 200 ng/mL or less (corresponding to an increase in heart rate of 11 bpm or less). In still another embodiment, it means a formulation in which the Cmax when administered in a fasted state is 150 ng/mL or less (corresponding to an increase in heart rate of 9 bpm or less).

(R)-2-(2-aminothiazol-4-yl)-4'-[2-[(2-hydroxy-2-phenylethyl)amino]ethyl]acetic acid anilide (hereinafter sometimes referred to as compound A) is represented by the following structural formula.

[Chem. 1]

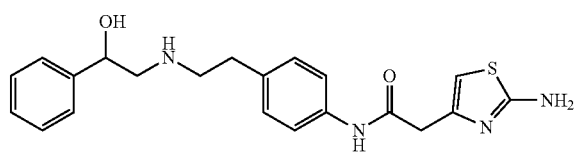

Compound A may be used in a free form which is not a salt, and may form a salt with an acid in other embodiments. Examples of such a salt include an acid addition salt with a mineral acid such as hydrochloric acid, hydrobromic acid, hydroiodic acid, sulfuric acid, nitric acid, phosphoric acid, or the like; and an acid addition salt with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid, or the like.

The dose of compound A may be appropriately selected in accordance with symptom, age, sex, and the like of the patient to be treated. The daily dose of compound A for oral administration to an adult is generally 0.01 to 100 mg/kg, which is administered once or divided into two to four doses per day.

The content of compound A per formulation is, for example, 1% by weight to 70% by weight, 5% by weight to 70% by weight in another embodiment, and 5% by weight to 50% by weight in still another embodiment. The content of compound A per formulation is 1 mg to 500 mg, and 10 mg to 200 mg in another embodiment.

A carrier for a sustained release pharmaceutical composition, which is contained in the pharmaceutical composition for modified release of the present invention together with compound A or a pharmaceutically acceptable salt thereof, is not particularly limited, so long as it is a carrier, a pharmaceutical formulation, or a technique for manufacturing pharmaceutical preparations capable of controlling the Cmax when administered in a fasted state to a specific vale or less.

Examples of such a carrier (or a pharmaceutical formulation, or a technique for manufacturing pharmaceutical preparations) which forms the composition or components in the present invention include, for example, (1) a sustained release hydrogel-forming formulation in which the formulation is almost completely gelled during the retention in the stomach and the small intestine of the upper digestive tract and the drug can be released in the colon of the lower digestive tract,
(2) a multi-layered formulation consisting of a drug core and a release-controlling layer which are geometrically arranged,
(3) a gel formulation in which a plurality of gums is combined,
(4) an osmotic pump type formulation,
(5) a formulation utilizing a swelling polymer,
(6) a matrix formulation utilizing a water-soluble polymer,
(7) a modified release formulation with a coating membrane,
(8) a matrix formation utilizing an insoluble polymer, and the like, as described in detail below. The compositions relating to these techniques for manufacturing pharmaceutical preparations, and the techniques per se are incorporated herein by reference.

Hereinafter, each embodiment of the pharmaceutical composition for modified release of the present invention will be explained in detail. Each embodiment described below is mainly explained with reference to cases using compound A as the active ingredient, but instead of compound A, a pharmaceutically acceptable salt thereof may be used.

(1) Sustained Release Hydrogel-Forming Formulation

The sustained release hydrogel-forming formulation contains, as the carrier for a sustained release pharmaceutical composition, an additive that allows water to penetrate into the formulation (designated as a gelling agent, a promoting agent for gelling, and a hydrophilic base, but hereinafter referred to as hydrophilic base), and a polymer which forms a hydrogel (hereinafter referred to as hydrogel-forming polymer).

It is necessary that the hydrogel-forming polymer used in the present invention can control the release rate of the drug, to the extent that the blood concentration profile of the drug is not affected by the presence or absence of food intake.

The molecular weight of the hydrogel-forming polymer is, for example, 100,000 or more, 100,000 to 8,000,000 in another embodiment, 100,000 to 5,000,000 in still another embodiment, and 100,000 to 2,000,000 in still another embodiment. The viscosity of the hydrogel-forming polymer is, for example, 12 mPa·s or more in a 5% aqueous solution at 25° C.; 12 mPa·s or more in a 5% aqueous solution at 25° C., and 40,000 mPa·s or less in a 1% aqueous solution at 25° C. in another embodiment; 400 mPa·s or more in a 2% aqueous solution at 25° C., and 7,500 mPa·s or less in a 1% aqueous solution at 25° C. in still another embodiment; and 400 mPa·s or more in a 2% aqueous solution at 25° C., and 5,500 mPa·s or less in a 1% aqueous solution at 25° C. in still another embodiment.

In the pharmaceutical composition for modified release of the present invention, the release period of time of the drug from the formulation can be arbitrarily controlled by adjusting the viscosity of the polymer which is used as the hydrogel-forming polymer.

The hydrogel-forming polymer used in the present invention is not particularly limited, so long as the release of the drug can be controlled to the extend that the effects of food on compound A may be reduced. Examples of the hydrogel-forming polymer include polyethylene oxide, hypromellose, hydroxypropyl cellulose, carboxymethyl cellulose sodium, hydroxyethyl cellulose, and carboxyvinyl polymers. Examples of the hydrogel-forming polymer in another embodiment include polyethylene oxide, hypromellose, and hydroxypropyl cellulose.

Examples of polyethylene oxide (hereinafter sometimes referred to as PEO) include product names, Polyox WSR-308 [average molecular weight: 8,000,000, viscosity: 10,000-15,000 mPa·s (1% aqueous solution at 25° C.)], Polyox WSR-303 [average molecular weight: 7,000,000, viscosity: 7,500-10,000 mPa·s (1% aqueous solution at 25° C.)], Polyox WSR Coagulant [average molecular weight: 5,000,000, viscosity: 5,500-7,500 mPa·s (1% aqueous solution at 25° C.)], Polyox WSR-301 [average molecular weight: 4,000,000, viscosity: 1,650-5,500 mPa·s (1% aqueous solution at 25° C.)], Polyox WSR-N-60K [average molecular weight: 2,000,000, viscosity: 2,000-4,000 mPa·s (2% aqueous solution at 25° C.)], Polyox WSR-N-12K [average molecular weight: 1,000,000, viscosity: 400-800 mPa·s (2% aqueous solution at 25° C.)], Polyox WSR-1105 [average molecular weight: 900,000, viscosity: 8,800-17,600 mPa·s (5% aqueous solution at 25° C.)], Polyox WSR-205 [average molecular weight: 600,000, viscosity: 4,500-

8,800 mPa·s (5% aqueous solution at 25° C.)], Polyox WSR-N-750 [average molecular weight: 300,000, viscosity: 600-1200 mPa·s (5% aqueous solution at 25° C.)], Polyox WSR-N-80 [average molecular weight: 200,000, viscosity: 55-90 mPa·s (5% aqueous solution at 25° C.)], and Polyox WSR-N-10 [average molecular weight: 100,000, viscosity: 12-50 mPa·s (5% aqueous solution at 25° C.)] (DOW).

Examples of hypromellose (hereinafter sometimes referred to as HPMC) include product name Metolose 90SH50000 [viscosity in a 2% aqueous solution at 20° C.: 2,900-3,900 mPa·s], Metolose SB-4 (product name, Shin-Etsu Chemical Co., Ltd.) (viscosity in a 2% aqueous solution at 20° C.: approximately 4 mPa·S), TC-5RW (product name, Shin-Etsu Chemical Co., Ltd.) (viscosity in a 2% aqueous solution at 20° C.: approximately 6 mPa·S), TC-5S (product name, Shin-Etsu Chemical Co., Ltd.) (viscosity in a 2% aqueous solution at 20° C.: approximately 15 mPa·S), TC-5R (product name, Shin-Etsu Chemical Co., Ltd.) (viscosity in a 2% aqueous solution at 20° C.: approximately 6 mPa·S), TC-5M (product name, Shin-Etsu Chemical Co., Ltd.) (viscosity in a 2% aqueous solution at 20° C.: approximately 4.5 mPa·S), TC-5E (product name, Shin-Etsu Chemical Co., Ltd.) (viscosity in a 2% aqueous solution at 20° C.: approximately 3 mPa·S), Metolose 60SH-50 (product name, Shin-Etsu Chemical Co., Ltd.) (viscosity in a 2% aqueous solution at 20° C.: approximately 50 mPa·s), Metolose 65SH-50 (product name, Shin-Etsu Chemical Co., Ltd.) (viscosity in a 2% aqueous solution at 20° C.: approximately 50 mPa·s), Metolose 90SH-100 (product name, Shin-Etsu Chemical Co., Ltd.) (viscosity in a 2% aqueous solution at 20° C.: approximately 100 mPa·s), Metolose 90SH-100SR (product name, Shin-Etsu Chemical Co., Ltd.) (viscosity in a 2% aqueous solution at 20° C.: approximately 100 mPa·s), Metolose 65SH-400 (product name, Shin-Etsu Chemical Co., Ltd.) (viscosity in a 2% aqueous solution at 20° C.: approximately 400 mPa·s), Metolose 90SH-400 (product name, Shin-Etsu Chemical Co., Ltd.) (viscosity in a 2% aqueous solution at 20° C.: approximately 400 mPa·s), Metolose 65SH-1500 (product name, Shin-Etsu Chemical Co., Ltd.) (viscosity in a 2% aqueous solution at 20° C.: approximately 1,500 mPa·s), Metolose 60SH-4000 (product name, Shin-Etsu Chemical Co., Ltd.) (viscosity in a 2% aqueous solution at 20° C.: approximately 4,000 mPa·s), Metolose 65SH-4000 (product name, Shin-Etsu Chemical Co., Ltd.) (viscosity in a 2% aqueous solution at 20° C.: approximately 4,000 mPa·s), Metolose 90SH-4000 (product name, Shin-Etsu Chemical Co., Ltd.) (viscosity in a 2% aqueous solution at 20° C.: approximately 4,000 mPa·s), Metolose 90SH-4000SR (product name, Shin-Etsu Chemical Co., Ltd.) (viscosity in a 2% aqueous solution at 20° C.: approximately 4,000 mPa·s), Metolose 90SH-15000 (product name, Shin-Etsu Chemical Co., Ltd.) (viscosity in a 2% aqueous solution at 20° C.: approximately 15,000 mPa·s), Metolose 90SH-15000SR (product name, Shin-Etsu Chemical Co., Ltd.) (viscosity in a 2% aqueous solution at 20° C.: approximately 15,000 mPa·s), and Metolose 90SH-30000 (product name, Shin-Etsu Chemical Co., Ltd.) (viscosity in a 2% aqueous solution at 20° C.: approximately 30,000 mPa·s).

Examples of hydroxypropyl cellulose (hereinafter sometimes referred to as HPC) include HPC-SSL (product name, Nippon Soda Co., Ltd.) (viscosity in a 2% aqueous solution at 20° C.: 2.0-2.9 mPa·S), HPC-SL (product name, Nippon Soda Co., Ltd.) (viscosity in a 2% aqueous solution at 20° C.: 3.0-5.9 mPa· S), HPC-L (product name, Nippon Soda Co., Ltd.) (viscosity in a 2% aqueous solution at 20° C.: 6.0-10.0 mPa· S), HPC-M (product name, Nippon Soda Co., Ltd.) (viscosity in a 2% aqueous solution at 20° C.: 150-400 mPa·S), and HPC-H (product name, Nippon Soda Co., Ltd.) (viscosity in a 2% aqueous solution at 20° C.: 1,000-4,000 mPa·S).

Examples of methylcellulose (hereinafter sometimes referred to as MC) include Metolose SM15 (product name, Shin-Etsu Chemical Co., Ltd.) (viscosity in a 2% aqueous solution at 20° C.: approximately 15 mPa·S), Metolose SM25 (product name, Shin-Etsu Chemical Co., Ltd.) (viscosity in a 2% aqueous solution at 20° C.: approximately 25 mPa·S), Metolose SM100 (product name, Shin-Etsu Chemical Co., Ltd.) (viscosity in a 2% aqueous solution at 20° C.: approximately 100 mPa·S), Metolose SM400 (product name, Shin-Etsu Chemical Co., Ltd.) (viscosity in a 2% aqueous solution at 20° C.: approximately 400 mPa·S), Metolose SM1500 (product name, Shin-Etsu Chemical Co., Ltd.) (viscosity in a 2% aqueous solution at 20° C.: approximately 1,500 mPa·S), and Metolose SM4000 (product name, Shin-Etsu Chemical Co., Ltd.) (viscosity in a 2% aqueous solution at 20° C.: approximately 4,000 mPa·S).

Examples of carboxymethyl cellulose sodium (hereinafter sometimes referred to as CMCNa) include product names, Sunrose F-30MC [viscosity: 250-350 mPa·s (1% aqueous solution at 25° C.)], Sunrose F-150MC [average molecular weight: 200,000, viscosity: 1, 200-1, 800 mPa·s (1% aqueous solution at 25° C.)], Sunrose F-600MC [viscosity: 6,000-8,000 mPa·s (1% aqueous solution at 25° C.)], Sunrose F-1000MC [average molecular weight: 420,000, viscosity: 8,000-12,000 mPa·s (the same)], Sunrose F-1400MC [viscosity: 12,000-15,000 mPa·s (1% aqueous solution at 25° C.)], and Sunrose F-300MC [average molecular weight: 300,000, viscosity: 2,500-3,000 mPa·s (the same)] (Nippon Paper Chemicals Co., Ltd.).

Examples of hydroxyethyl cellulose (hereinafter sometimes referred to as HEC) include product names, HEC DAICEL SE850 [average molecular weight: 1,480,000, viscosity: 2,400-3,000 mPa·s (1% aqueous solution at 25° C.)], and HEC DAICEL SE900 [average molecular weight: 1,560,000, viscosity: 4,000-5,000 mPa·s (1% aqueous solution at 25° C.)] (Daicel chemical Industries, Ltd.).

Examples of carboxyvinyl polymers include Carbopol 71G (viscosity: 4,000-11,000 mPa·s), Carbopol 971P (viscosity: 4,000-11,000 mPa·s), Carbopol 981 (viscosity: 4,000-10,000 mPa·s), Carbopol 941 (viscosity: 4,000-10, 000 mPa·s), Carbopol 934 (viscosity: 30,500-39,400 mPa·s), and Carbopol 934P (viscosity: 29,400-39,400 mPa·s) (B.F. Goodrich Chemical).

These hydrogel-forming polymers may be used alone, or as an appropriate combination of two or more thereof. A combination of different lots may be used.

The content of the hydrogel-forming polymer is not particularly limited, so long as it is an amount to the extent that the blood concentration profile of the drug is not affected by the presence or absence of food intake. The content of the hydrogel-forming polymer is, for example, 1% by weight to 70% by weight with respect to the total weight of the formulation, and 3% by weight to 70% by weight in another embodiment. The content of the hydrogel-forming polymer is 5% by weight to 70% by weight with respect to the total weight of the formulation, 10% by weight to 60% by weight in another embodiment, and 10% by weight to 40% by weight in still another embodiment. The content of the hydrogel-forming polymer is 0.1% by weight to 1,000% by weight with respect to the weight of the drug, 1% by weight to 500% by weight in another embodiment, and 5% by weight to 300% by weight in still another embodiment.

A polymer of which the viscosity (before mixing) is beyond the specific range can be used as an appropriate combination with one or more other polymers, in case that the mixture obtained by mixing these plural polymers has a viscosity (as measured before the use) within the specific range.

In the additive which ensures penetration of water into the pharmaceutical composition of the present invention (hydrophilic base), the amount of water necessary to dissolve 1 g of the hydrophilic base at 20±5° C. is 10 mL or less, 6 mL or less in another embodiment, 5 mL or less in still another embodiment, and 4 mL or less in still another embodiment. When the hydrophilic base has a high solubility to water, the effect that allows water to penetrate into the formulation is high.

Examples of the hydrophilic base include water-soluble polymers, such as polyethylene glycol [PEG: for example, product names PEG 400, PEG 1500, PEG 4000, PEG 6000, and PEG 20000 (NOF Corporation)], polyvinyl pyrrolidone (PVP: for example, product name PVP K30 (BASF), and the like; sugar alcohols, such as D-mannitol, D-sorbitol, xylitol, and the like; saccharides, such as lactose, sucrose, anhydrous maltose, D-fructose, dextran (for example, Dextran 40), glucose, and the like; surfactants, such as polyoxyethylene hydrogenated castor oil [HCO: for example, Cremophor RH40 (BASF), HCO-40, HCO-60 (Nikko Chemicals)], polyoxyethylene polyoxypropylene glycol [for example, Pluronic F68 (ADEKA Corporation and the like)], polyoxyethylene sorbitan higher fatty acid esters [Tween: for example, Tween 80 (Kanto Chemical)], and the like; salts, such as sodium chloride, magnesium chloride, and the like; organic acids, such as citric acid, tartaric acid, and the like; amino acids, such as glycine, β-alanine, lysine hydrochloride, and the like; and aminosaccharides, such as meglumine and the like.

As another embodiment, PEG, PVP, D-mannitol, D-sorbitol, xylitol, lactose, sucrose, anhydrous maltose, D-fructose, dextran, glucose, polyoxyethylene polyoxypropylene glycol, sodium chloride, magnesium chloride, citric acid, tartaric acid, glycine, β-alanine, lysine hydrochloride, or meglumine may be used. As still another embodiment, PEG, PVP, D-mannitol, lactose, sucrose, sodium chloride, polyoxyethylene polyoxypropylene glycol, or the like may be used.

These hydrophilic bases may be used alone, or as an appropriate combination of two or more thereof.

The content of the hydrophilic base is not particularly limited, so long as it is an amount capable of controlling the release of the drug to the extent that the release of the drug is not affected by food. The content of the hydrophilic base is, for example, 5% by weight to 75% by weight, 5% by weight to 70% by weight in another embodiment, and 20% by weight to 60% by weight in still another embodiment.

The sustained release hydrogel-forming formulation, as an embodiment of the pharmaceutical composition for modified release of the present invention, may be prepared as various dosage forms, which include, for example, formulations for oral administration such as tablets, capsules (including microcapsules), granules, and powder, and formulations for parenteral administration such as suppositories (for example, rectal suppositories or vaginal suppositories). These formulations may be safely administered orally or parenterally. Formulations for oral administration such as tablets, capsules, and granules may be selected in another embodiment.

Hereinafter, various pharmaceutical additives which may be used in the sustained release hydrogel-forming formulation, as an embodiment of the pharmaceutical composition for modified release of the present invention, and various methods for preparing the sustained release hydrogel-forming formulation will be explained, but these explanations are not particularly limited to the sustained release hydrogel-forming formulation, and can be applied to formulations other than the sustained release hydrogel-forming formulation.

The pharmaceutical composition for modified release of the present invention may be prepared by mixing the drug, the hydrogel-forming polymers, and the hydrophilic base, and forming the mixture into a predetermined shape. The mixing and forming may be carried out in accordance with conventional methods widely used in the technical field for formulation. A pharmaceutically acceptable carrier may be used in the mixing and/or forming, if desired.

In the preparation of the pharmaceutical composition for modified release of the present invention, further various pharmaceutical additives may be used, if desired. Such pharmaceutical additives are not particularly limited, so long as they are pharmaceutically acceptable. Examples of the pharmaceutical additives include various organic or inorganic carrier substances which are widely used as formulation materials, such as fillers, lubricants, binders, and disintegrating agents. Other formulation additives such as preservatives, antioxidants, stabilizers, film coating agents, coloring agents, and sweeteners may be used, if desired.

Examples of the fillers include lactose, sucrose, D-mannitol, D-sorbitol, starch, gelatinized starch, dextrin, crystalline cellulose, low substituted hydroxypropyl cellulose, carboxymethyl cellulose sodium, gum arabic, dextrin, pullulan, light anhydrous silicic acid, synthetic aluminum silicate, magnesium aluminate metasilicate, and the like.

Examples of the lubricants include magnesium stearate, calcium stearate, talc, colloidal silica, and the like.

Examples of the binders include gelatinized starch, sucrose, gelatin, gum arabic, methylcellulose, carboxymethyl cellulose, carboxymethyl cellulose sodium, crystalline cellulose, sucrose, D-mannitol, trehalose, dextrin, pullulan, hydroxypropyl cellulose, hypromellose, polyvinylpyrrolidone, and the like.

Examples of the disintegrating agents include lactose, sucrose, starch, carboxymethyl cellulose, carboxymethyl cellulose calcium, croscarmellose sodium, carboxymethyl starch sodium, light anhydrous silicic acid, low substituted hydroxypropylcellulose, and the like.

Examples of the preservatives include p-hydroxybenzoate esters, chlorobutanol, benzyl alcohol, phenethyl alcohol, dehydroacetic acid, sorbic acid, and the like.

Examples of the antioxidants include butylated hydroxytoluene (BHT), propyl gallate (PG), butylhydroxyanisol (BHA), ascorbic acid, sodium ascorbate, erythorbic acid, sodium nitrite, sodium bisulfite, sodium pyrosulfite, citric acid, and edetate sodium; BHT, PG, and sodium ascorbate in another embodiment; and BHT in still another embodiment.

Examples of the stabilizers include yellow ferric oxide, red ferric oxide, black iron oxide, and the like.

Examples of the film coating agents include pharmaceutically commonly-used bases, such as water-soluble polymers, plasticizers, and inorganic substances, or a combination thereof.

Examples of the coloring agents include water-soluble edible tar pigments (examples: edible pigments such as food red No. 2, food red No. 3, food yellow No. 4, food yellow No. 5, food blue No. 1, and food blue No. 2), water-insoluble lake pigments (examples: aluminum salts of the above water-soluble edible tar pigments), natural pigments (examples: β-carotene, chlorophyll, and colcothar), and the like.

Examples of the sweeteners include saccharin sodium, dipotassium glycyrrhizinate, aspartame, *stevia*, and the like.

These carriers or formulation additives may be used alone, or as an appropriate combination of two or more thereof. With respect to the contents thereof, they may be used in appropriate amounts.

Hereinafter, the process of manufacturing the pharmaceutical composition for modified release of the present invention will be explained, the present invention is not limited to the following particular embodiments.

The pharmaceutical composition for modified release of the present invention may be prepared by known methods per se, such as dry granulation, wet granulation, fluidized bed granulation, intermittent granulation, agitation granulation, or the like.

As a method of de-lumping or pulverizing the drug, conventional crushing or pulverizing methods may be applied, for example, using an impact mill (Hosokawa Micron Corporation; Fine Impact Mill), a dry & wet mill (Powrex Corporation: Comil), or a cutting mill granulator (Dalton Corporation; Power Mill).

As a method of pulverizing the hydrophilic base, the hydrogel-forming polymer, or the formulation additives, conventional pulverizing methods may be applied, for example, using an impact mill (Hosokawa Micron Corporation; Fine Impact Mill or Sample Mill) or a jet mill (Horkos Corp; Jet Mill).

As a method of granulating the drug, conventional granulation methods may be used. Examples of such methods include a fluidized bed granulation method, an intermittent granulation method, an agitation granulation method, a high-speed agitation granulation method, a tumbling fluidized bed granulation method, an extrusion granulation method, a pulverization granulation method, a dry granulation method, and the like. In another embodiment, examples thereof include a fluidized bed granulation method, an intermittent granulation method, an agitation granulation method, a high-speed agitation granulation method, a tumbling fluidized bed granulation method, and a dry granulation method, and any method capable of granulating the drug may be used. Examples of a granulator include a fluidized bed granulator (for example, Flow Coater; Freund Corporation, or GPCG; Glatt GmbH), a granulation and coating apparatus equipped with a horizontal rotating disc having a flat powder contact portion [for example, a centrifugal fluidizing granulator (for example, CF granulator; Freund Corporation)], a granulation and coating apparatus having a rotating disk with a flat surface placed at the bottom of a fluidized bed and having an aeration portion (for example, Spiralflow, or Flowcoater with a rotor container; Freund Corporation), and a dry granulator in which material powder is directly compressed, molded, crushed, and sieved (for example, Roller Compactor; Freund Corporation).

In the dry granulation, for example, the drug, the hydrogel-forming polymer, the hydrophilic base, and additives such as a filler may be compression-molded using a dry granulator, and then, may be crushed and sieved to obtain granulated products having a desired size.

In the wet granulation, for example, while the drug, the hydrogel-forming polymer, the hydrophilic base, and additives such as a filler is fluidized, an appropriate amount of water or a liquid containing the hydrophilic base and the binder may be sprayed. The liquid containing the hydrophilic base may be prepared by dissolving or dispersing the essential component in a solvent such as water, ethanol, methanol, or the like. These solvents may be used as an appropriate mixture thereof.

The amount of water used in the granulation is not particularly limited, so long as the binder or formulation additives may be uniformly dissolved and/or suspended (dispersed) in the water. When the hydrophilic base is used in the solid form, the amount of water is not particularly limited, so long as the hydrogel-forming polymer can be granulated.

When the hydrophilic base is used in the liquid form, the amount of water to the hydrogel-forming polymer is generally 10% by weight or less, 8% by weight or less in another embodiment, and 5% by weight or less in still another embodiment. A method of adding water in the granulation is not particularly limited, so long as a nonuniform mixture consisting of untreated powder and aggregates, which are generally powdery, is not generated. Examples thereof include a continuous spray method in which water is continuously added, an intermittent spray method in which a dry step (and a shaking step, if desired) is carried out during the granulation step, and the like.

The addition rate of water in the granulation is not particularly limited, so long as a nonuniform mixture consisting of untreated powder and aggregates, which are generally powdery, is not generated. In the fluidized bed granulation, the addition rate of water to the hydrogel-forming polymer is generally 0.1% by weight/min. to 1% by weight/min., 0.2% by weight/min. to 0.8% by weight/min. in another embodiment, and 0.4% by weight/min. to 0.6% by weight/min. in still another embodiment.

The temperature of the powder in the granulation is not particularly limited, so long as it does not induce thermal denaturation of the hydrogel-forming polymer. The temperature is, for example, 20° C. to the melting point (62° C. to 67° C.) of the hydrogel-forming polymer, 20° C. to 50° C. in another embodiment, 20° C. to 35° C. in still another embodiment, and 25° C. to 30° C. in still another embodiment.

The concentration of the binder liquid as a solid content which may be used in the granulation is, for example, 1% to 20% as a formulation amount. The binder is not particularly limited, so long as it is pharmaceutically acceptable.

The binder may be added in the solid form to a granulator, and then, water may be sprayed as the binder liquid. Alternatively, the binder may be dissolved in water, and then, the resulting binder liquid may be sprayed.

An appropriate spray rate of the binder liquid varies according to a production method to be applied or its production scale. In a 1-kg scale production by the fluidized bed granulation, the spray rate is 2 g/min. to 20 g/min., and 5 g/min. to 15 g/min. in another embodiment.

An appropriate temperature of the product in the granulation is 15° C. to 50° C., and 15° C. to 40° C. in another embodiment.

The resulting granulated products may be, for example, dried or heated.

In the drying step, an apparatus and a method are not particularly limited, so long as the granulated products can be dried. Examples of an apparatus for drying include a fluidized bed granulator (for example, Flow Coater; Freund Corporation, or GPCG; Glatt GmbH), a granulation and coating apparatus equipped with a horizontal rotating disc having a flat powder contact portion [for example, a centrifugal fluidizing granulator (for example, CF granulator; Freund Corporation)], a granulation and coating apparatus having a rotating disk with a flat surface placed at the bottom of a fluidized bed and having an aeration portion (for example, Spiralflow, or Flowcoater with a rotor container; Freund Corporation), and the like. The conditions for drying are not particularly limited, so long as the granulated products may be generally dried in the fluidized bed. The drying of the granulated products will be almost completed, for example, under the conditions in which the dry inlet air temperature is 50° C. and the drying is carried out until the temperature of the granulated products becomes 40° C. and, in another embodiment, under the conditions in which the dry inlet air temperature is 40° C. and the drying is carried out until the temperature of the granulated products becomes 30° C. As the drying method, forced-air drying or drying under reduced pressure may be used.

The granulated products may be sieved.

In the sieving step, an apparatus and a method are not particularly limited, so long as the granulated products can be sieved. Examples of an apparatus for sieving include a screen, a dry & wet mill (Powrex Corporation: Comil), a cutting mill granulator (Dalton Corporation; Power Mill), and the like. The conditions for sieving are not particularly limited, so long as the granulated products may be generally sieved to obtain particles having a desired size.

Examples of tabletting include a direct tabletting method in which the drug, the hydrophilic base, and the hydrogel-forming polymer are mixed with an appropriate additive(s), and the mixture is compression-molded to obtain tablets; a method in which a composition obtained by a wet granulation (the granulation is carried out by spraying a mixture of the drug, the hydrophilic base, the hydrogel-forming polymer, and additives with a binder liquid) or a melting granulation (the granulation is carried out by heating a mixture of the drug, the hydrophilic base, the hydrogel-forming polymer, and an appropriate low-melting substance) is formed into tablets; and the like.

A rotary tabletting machine, a single punch tabletting machine, and the like may be used as a tabletting machine. A method as well as an apparatus is not particularly limited, so long as a compression-molded product (preferably tablets) can be pharmaceutically produced.

After the tabletting, the obtained tablets may be dried. The initial water content of the tablet is, for example, 2% by weight/tablet or less, 1.5% by weight/tablet or less in another embodiment, and 0.9% by weight/tablet or less in still another embodiment.

After the tabletting, the obtained tablets may be film coated using a pan coating machine at an amount of 1% by weight to 5% by weight per tablet.

(2) Multi-Layered Formulation Consisting of Drug Core and Release-Controlling Layer which are Geometrically Arranged A multilayered formulation, an embodiment of the pharmaceutical composition for modified release according to the present invention, may be a two-layered or three-layered formulation for modified release, characterized by consisting of a drug-containing layer and a release-controlling layer, and consisting of:

a) the first layer (layer 1) which is prepared by compressing a mixture or granules containing 5 to 90 W/W % (preferably 10 to 85 W/W %) of a water-soluble polymer in this layer, and has a property of being swollen by contact with environmental fluids, b) the second layer (layer 2) comprising compound A, a water-soluble polymer, and other filler(s), which is adjacent to the first layer, has a property suitable to compression-molding, and is designed to release the physiologically active substance within a predetermined period of time, and c) the third layer (layer 3) (which may be optionally adjacent to the layer 2) which contains a water-soluble polymer capable of being generally gelled and/or swollen followed by optionally being disintegrated, and has a property of controlling the release of compound A from the layer 2. The "environmental fluids" include, for example, an aqueous solution as used in a dissolution test, as well as body fluids such as blood or gastrointestinal fluids.

Techniques for such a multilayered formulation which may be used in the pharmaceutical composition for modified release according to the present invention are disclosed in, for example, U.S. Pat. Nos. 4,839,177, 5,422,123, 5,780, 057, 6,149,940, Japanese Patent Publication (Kokai) No. 2005-162736, and Japanese Patent Publication (Kokai) No. 2005-162737, the contents of which are incorporated herein by reference. As disclosed in U.S. Pat. Nos. 4,839,177 and 5,422,123, the multilayered formulation is characterized in that a release rate of the drug from the pharmaceutical formulation is controlled by sandwiching the layer 2 containing the drug between the layer 1 and the layer 3 in which the drug is not contained or is optionally contained. Further, as disclosed in U.S. Pat. Nos. 5,780,057 and 6,149,940, it is known that when the multilayered formulation is brought into contact with body fluids, at least one of the layer 1 and the layer 3 are rapidly swollen followed by the layer 2 is swollen, that is, the volume of the formulation is significantly increased, and as a result, the formulation remains in the stomach for a longer period of time, and almost all of the active substance contained therein is released and absorbed at the upper gastrointestinal tract in a controlled manner.

The layer 1 and the layer 3 may have the same composition and the same functional properties, or may have different compositions and different functional properties. When the layer 1 and the layer 3 have the same composition and functional properties, the amounts and thicknesses of the layers 1 and 3 which sandwich the layer 2 may be changed. At least one of the layers 1 and 3 acts as a barrier for the release of the active substance, that is, it is impermeable enough for compound A contained in the layer 2 not to be released or diffused therefrom. Further, at least one of the layers 1 and 3 can be rapidly swollen, that is, the volume thereof is rapidly increased. The layer 3 may optionally contain the drug so that a drug release which is different from that released from the layer 2 can be supplementally added to the pharmaceutical formulation.

The water-soluble polymers used in the layer 1, the layer 3, and the layer 2 are not particularly limited, so long as they are pharmaceutically acceptable and biocompatible. Such water-soluble polymers may be gradually dissolved and/or gelled in an aqueous liquid, and/or may be gelled rapidly or at a different rate and then optionally disintegrated. Examples of the water-soluble polymers include, for example, hydroxymethyl cellulose, hydroxyethyl cellulose, hypromellose having a molecular weight of 1,000 to 4,000, 000, hydroxypropyl cellulose having a molecular weight of 2,000 to 2,000,000, carboxyvinyl polymers, chitosans, mannans, galactomannans, xanthans, carageenans, amylose, alginic acid, salts and derivatives thereof, pectin, acrylates, methacrylates, acrylate/methacrylate copolymers, polyacid anhydrides, polyamino acids, poly(methylvinyl ether/maleic anhydride) polymers, polyvinyl alcohols, glucans, scleroglucans, carboxymethyl cellulose and derivatives thereof, ethyl cellulose, methyl cellulose, or conventional water-soluble cellulose derivatives. Hypromellose having a molecular weight of 3,000 to 2,000,000 is preferable. The content of the water-soluble polymer in the layer 1 or the layer 3 is generally 5 to 90 W/W %, preferably 10 to 85 W/W %, more preferably 20 to 80 W/W %, with respect to the weight of each layer. The content of the water-soluble polymer in the layer 2 is generally 5 to 90 W/W %, preferably 10 to 85 W/W %, to the weight of the layer.

In the process for preparing the layer 1 and the layer 3, a water-soluble filler which promotes the degree of wetness of the layers may be used, to rapidly increase the volume of the multilayered formulation containing the above water-soluble polymer. The water-soluble filler may be preferably selected from a group of fillers having an extremely rapid disintegrability, such as cross-linked polyvinylpyrrolidone, hydroxypropyl cellulose or hypromellose having a low or medium molecular weight, cross-linked carboxymethyl cellulose sodium, carboxymethyl starch or salts thereof, divinylbenzene/potassium methacrylate copolymers, or the like. The content of the filler is 1 to 90 W/W % or less, preferably 5 to 50 W/W % of each layer.

If desired, a surfactant (anionic, cationic, or nonionic surfactants) may be further used to improve the degree of wetness. As a result, tablets and environmental fluids may conform with each other more rapidly, and the tablets, particularly the gel-forming layer, may be gelled more rapidly. Examples of the surfactant include, for example, sodium laurylsulfate, sodium ricinolate, sodium tetradecylsulfonate, sodium dioctylsulfosuccinate, cetomagrogol, poloxamer, glycerol monostearate, polysorbate, sorbitan monolaurate, lecithins, or other pharmaceutically acceptable surfactants.

If desired, another substance which modifies hydration may be further used. Such a substance may be selected from, for example, mannitol, lactose, starches derived from various organs, sorbitol, xylitol, microcrystalline cellulose, and/or a diluent capable of generally promoting a penetration of water or an aqueous liquid into a pharmaceutical composition; or a hydrophobic diluent to retard a penetration of water or an aqueous liquid into a pharmaceutical formulation, such as ethyl cellulose, glycerol monostearate, palmitate, or hydrogenated or non-hydrogenated vegetable oils (for example, hydrogenated castor oil, wax, monoglyceride, diglyceride, or triglyceride). It is preferable to select ethyl cellulose or hydrogenated vegetable oils as the hydrophobic diluent.

The content of the hydrophobic diluent in the layer 1 or the layer 3 is generally 1 to 60 W/W %, preferably 5 to 40 W/W %, more preferably 10 to 30 W/W %, with respect to the weight of each layer.

To control the release rate of compound A from the pharmaceutical formulation, microcrystalline or a water-soluble base, such as dextrose, sucrose, fructose, maltose, xylitol, citric acid, lactose, mannitol, or the like, may be used in the layer 2, if desired.

The content of microcrystalline and/or the water-soluble base in the layer 2 is generally 5 to 90 W/W %, preferably 10 to 80 W/W %, more preferably 20 to 70 W/W %, with respect to the weight of the layer.

The multilayered formulation of the present invention may contain, for example, a lubricant, such as magnesium stearate, talc, stearic acid, glycerol monostearate, polyoxyethylene glycol having a molecular weight of 400 to 7,000,000, hydrogenated castor oil, glycerol behenate, monoglyceride, diglyceride, triglyceride, or the like, a fluidizing agent such as colloidal silica or other silica, a binder, a buffer, an absorbing agent, or other pharmaceutically acceptable additives.

The multilayered formulation of the present invention may be manufactured, for example, by mixing powder and/or granules by a known manufacturing technique per se, and forming the mixture into tablets by compression. A two-layered or three-layered pharmaceutical formulation, such as a tablet, may be manufactured by a known method per se. The multilayered formulation of the present invention may be manufactured, for example, by using a rotary press capable of manufacturing multilayered tablets. It is preferable that a tabletting pressure is generally 7 to 50 kN. When the tablets are manufactured on a small scale, a mortar and pestle may be used to prepare powder and/or granules, and then, an oil press tabletting machine may be used to manufacture two-layered or three-layered tablets. The thickness of each layer of the formulation may vary according to the content of the active substance, and is preferably 0.2 to 8 mm, more preferably 1 to 4 mm. In the formulation of the present invention, for example, a coating layer with a macromolecular material may be applied to the pharmaceutical composition. Such a coating may be applied by using an organic or aqueous solution, in accordance with a known method per se.

When the multilayered formulation of the present invention is brought into contact with gastric juices in the gastrointestinal tract and/or liquids, the volume thereof is rapidly increased. This increase in volume may be limited in a single layer or several layers of the formulation. Such a formulation may be in a form of a tablet, small tablets, or a gelatin capsule consisting of small tablets. Further, at least two small tablets may be combined in the same formulation, and may be packed in, for example, a wafer capsule or a gelatin capsule. When the formulation consists of small tablets, each small tablet may have a different composition or the same composition.

(3) Gel Formulation in which a Plurality of Gums is Combined

A gel formulation in which a plurality of gums is combined, an embodiment of the pharmaceutical composition for modified release according to the present invention, is characterized by comprising at least compound A and a gum base. The gum base as used herein means a sustained release filler comprising a homopolysaccharide which can form a crosslinkage with a heteropolysaccharide gum when exposed to the heteropolysaccharide gum and environmental fluids (such as body fluids, an aqueous solution for an in vitro dissolution test, or the like). The sustained release filler may further comprise calcium sulfate and/or a water-soluble base. The gel formulation may further contain a commonly used filler.

Techniques for obtaining the gel formulation in which a plurality of gums is combined, which may be used in the pharmaceutical composition for modified release according to the present invention, are disclosed in, for example, U.S. Pat. Nos. 4,994,276, 5,128,143, 5,135,757, and Japanese Patent No. 2832248. As disclosed therein, it is known that a heterogeneously dispersed filler comprising a combination of a heteropolysaccharide and a homopolysaccharide exhibiting a synergistic effect, such as a combination of two or more polysaccharide gums, has a viscosity higher than that of any single gum, and can cause a rapid hydration, and thus a harder gel is generated more rapidly. The contents of the above patent references are incorporated herein by reference.

The heteropolysaccharide as used herein is defined as a water-soluble polysaccharide containing two or more sugar units. The heteropolysaccharide is not particularly limited, so long as it has a branched-chain or spiral configuration, and has an excellent water absorbing property and a high viscosity improving property. As the heteropolysaccharide, for example, xanthan gum or derivatives thereof (such as deacylated xanthan gum), carboxymethyl ether, or propylene glycol ester are preferable, and xanthan gum having a high molecular weight ($>10^6$) is more preferable.

The homopolysaccharide as used herein is not particularly limited, so long as it is a polysaccharide consisting of mannose and galactose, and can form a crosslinkage with a heteropolysaccharide. Locust bean gum having a high ratio of mannose to galactose is more preferable than other galactomannans such as guar or hydroxypropyl guar.

Other naturally-occurring polysaccharide gums may be used in the present invention. Examples of such polysaccharides include, for example, alginic acid derivatives, carrageenan, tragacanth gum, gum arabic, karaya gum, polyethylene glycol esters of these gums, chitin, chitosan, mucopolysaccharide, konjak, starch, substituted starch, starch fragment, dextrin, British gum having a molecular weight of approximately 10,000 Da, dextran, or the like. The starch may be used in an unmodified form, for example, an ungelled starch such as potato, rice, banana, or the like, or a semisynthetic or gelled starch.

As a combination of the heteropolysaccharide and the homopolysaccharide, the combination of xanthan gum and locust bean gum is particularly preferable. The content ratio of the heteropolysaccharide and the homopolysaccharide is not particularly limited, so long as it is an amount effective in enhancing a desired gel strength. Such a ratio (heteropolysaccharide gum:homopolysaccharide gum) is approximately 3:1 to approximately 1:3, preferably approximately 1:1.

The water-soluble cationic crosslinking agent as used herein is not particularly limited, so long as it is a pharmaceutically acceptable monovalent or polyvalent metal cation. As the binder, for example, calcium sulfate or the like may be used.

The water-soluble base as used herein is not particularly limited, so long as it is pharmaceutically acceptable. Examples of the water-soluble base include, for example, dextrose, sucrose, fructose, maltose, xylitol, citric acid, or the like.

The gel formulation in which a plurality of gums is combined of the present invention may be manufactured, for example, in a pharmaceutically acceptable form for oral administration such as a tablet or the like. In an embodiment, (1) a heteropolysaccharide gum, and a homopolysaccharide which can form a crosslinkage with the heteropolysaccharide gum when exposed to environmental fluids are mixed together under the dry condition with a pharmaceutically acceptable water-soluble base in a desired ratio, (2) the resulting mixture is subject to a wet granulation, (3) the granules are dried, (4) the dried granules are pulverized to obtain a sustained release filler having a desired particle size, (5) the resulting sustained release filler is granulated together with compound A, (6) the resulting granules are dried, (7) a conventional filler, such as a lubricant or the like, is added thereto, and (8) the resulting mixture is formed by compression into, for example, tablets. In another embodiment, a mixture of the sustained release filler and compound A may be granulated, together with an a solution of a hydrophobic substance (such as ethyl cellulose or the like) in an amount sufficient to retard the hydration of the filler (i.e., gums) without the destruction thereof, and then a conventional filler such as a lubricant is added thereto, and the resulting mixture is formed by compression into, for example, tablets.

In the wet granulation, predetermined amounts of the heteropolysaccharide gum, the homopolysaccharide gum, the cationic crosslinking agent, and the water-soluble base are homogeneously mixed; and then, a wetting agent, such as water, propylene glycol, glycerol, alcohol, or the like, is added thereto to prepare a wet aggregate; and the resulting wet aggregate is dried, and pulverized using a conventional apparatus to prepare granules having a predetermined particle size.

As the lubricant, for example, stearic acid or the like may be used. The mixing of the hydrophobic substance with the sustained release filler may be carried out, for example, by using a liquid in which the hydrophobic substance is dissolved and/or dispersed in an organic solvent, and further granulating the above-mentioned granules together with the liquid.

Examples of the hydrophobic substance include, for example, a pharmaceutical acceptable hydrophobic cellulose, such as ethyl cellulose or the like.

A combination and a mixing ratio of each component are not particularly limited. In a preferred embodiment, approximately 5 to 60 W/W % of xanthan gum (as the heteropolysaccharide) and locust bean gum (as the homopolysaccharide) (xanthan gum:locust bean gum=approximately 1:1) with respect to the total weight of the pharmaceutical formulation may be contained, and approximately 10 W/W % or less of calcium sulfate (as the water-soluble cationic crosslinking agent) and approximately 30 to 70 W/W % of dextrose (as an inert diluent) may be further contained. To control the release rate, the hydrophobic substance may be added, and, for example, approximately 5 to 10 W/W % of ethyl cellulose may be contained.

(4) Osmotic Pump Type Formulation

Osmotic pump type formulations utilize osmotic pressure to generate a driving force for imbibing fluid into a formulation, by a semipermeable membrane that permits free diffusion of fluid but not a drug or an osmoagent. The osmotic systems are characterized in that the action thereof is pH-independent, and a drug can be sustainedly released at a constant rate for a long time, even as the formulation transits the gastrointestinal tract and encounters environments having different pH values.

Such osmotic pump type formulations are reported in Santus and Baker, "Osmotic drug delivery: a review of the patent literature", Journal of Controlled Release, 35, p. 1-21, (1995). Further, osmotic pump type formulations are described in U.S. Pat. Nos. 3,845,770, 3,916,899, 3,995,631, 4,008,719, 4,111,202, 4,160,020, 4,327,725, 4,519,801, 4,578,075, 4,681,583, 5,019,397, and 5,156,850, the contents of which are incorporated herein by reference.

In the osmotic pump type formulation of the present invention, a bilayered compressed core consisting of a drug layer containing compound A, and a push layer, is coated with a semipermeable membrane that permits water or outer fluid but not a drug, an osmoagent, an osmopolymer, or the like. The semipermeable membrane is provided with at least one drug delivery orifice for connecting the inside of the formulation with the exterior environment. Therefore, after the osmotic pump type formulation is orally administered, fluid such as water transits the semipermeable membrane, and penetrates into the inside of the formulation. As a result, an osmotic action is generated, and compound A is sustainedly released through the drug delivery orifice(s) at a constant rate for a long time.

The drug layer contains compound A, as a mixture with a pharmaceutically acceptable additive(s).

The push layer contains one or more osmotic active components, but does not contain compound A, as described in detail below. Typical osmotic active component(s) contained in the push layer may be composed of an osmoagent and one or more osmopolymers. The osmopolymer as used herein means a polymer which has relatively a large molecular weight and swells when fluid is imbibed, to release compound A through the drug delivery orifice(s).

The semipermeable membrane used is not particularly limited, so long as it is permeable to the passage of an external fluid, such as water and biological fluids, and substantially impermeable to the passage of compound A, an osmoagent, an osmopolymer, and the like. Such a semipermeable membrane is essentially nonerodible, and insoluble in a living body.

As polymers for forming the semipermeable membrane, for example, semipermeable homopolymers, semipermeable copolymers, and the like may be used. As materials for such polymers, cellulosic polymers, such as cellulose esters, cellulose ethers, cellulose ester-ethers, and the like, may be used. The cellulosic polymers have a degree of substitution (DS) of anhydroglucose units of more than 0 and 3 or less. The degree of substitution (DS) means the average number of hydroxyl groups originally present on the anhydroglucose units that are replaced by a substituting group or converted into another group. The anhydroglucose unit can be partially or completely substituted with groups, such as acyl, alkanol, alkenoyl, aroyl, alkyl, alkoxy, halogen, carboalkyl, alkylcarbamate, alkylcarbonate, alkylsulfonate, alkylsulfamate, semipermeable polymer forming groups, and the like, wherein the organic moieties contain 1 to 12 carbon atoms, preferably 1 to 8 carbon atoms.

As the typical semipermeable compositions, one member, or two or more members selected from the group consisting of cellulose acylate, cellulose diacylate, cellulose triacylate, cellulose acetate, cellulose diacetate, cellulose triacetate, mono-, di-, and tri-cellulose alkanylates, mono-, di-, and tri-alkenylates, mono-, di-, and tri-aroylates, and the like, may be used. Representative polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like.

More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 47%; cellulose triacylates having a DS of 2.6 to 3, such as cellulose trivalerate, cellulose trilamate, cellulose tripalmitate, cellulose trioctanoate, and cellulose tripropionate; cellulose diesters having a DS of 2.2 to 2.6, such as cellulose disuccinate, cellulosedipalmitate, cellulose dioctanoate, cellulose dicaprylate, and the like; mixed cellulose esters, such as cellulose acetate valerate, cellulose acetate succinate, cellulose propionate succinate, cellulose acetate octanoate, cellulose valerate palmitate, cellulose acetate heptanoate, and the like. Semipermeable polymers are disclosed in U.S. Pat. No. 4,077,407, and can be synthesized and obtained by procedures described in Encyclopedia of Polymer Science and Technology, Vol. 3, pp. 325-354 (1964), Interscience Publishers Inc., New York, NY. The content of the polymers is not particularly limited, so long as it is an amount permeable to the passage of an external fluid, such as water and biological fluids, and substantially impermeable to the passage of compound A, an osmoagent, an osmopolymer, and the like. The content of the polymers is preferably 6 to 20 W/W %, more preferably 8 to 18 W/W %, with respect to the weight of a dilayered compressed core consisting of a drug layer and a push layer.

Semipermeable polymers for forming the semipermeable membrane further include cellulose acetaldehyde dimethyl acetate; cellulose acetate ethylcarbamate; cellulose acetate methyl carbamate; cellulose dimethylaminoacetate; semipermeable polyurethanes; semipermeable sulfonate polystyrenes; cross-linked selectively semipermeable polymers formed by the coprecipitation of an anion and a cation, as disclosed in U.S. Pat. Nos. 3,173,876, 3,276,586, 3,541,005, 3,541,006, and 3,546,142; semipermeable polymers, as disclosed in U.S. Pat. No. 3,133,132; semipermeable polystyrene derivatives; semipermeable poly(sodium styrenesulfonate); semipermeable poly(vinylbenzyltrimethylammonium chloride); and semipermeable polymers exhibiting a fluid permeability of $10^{-5}$ to $10^{-2}$ (cc mL/cm hr atm), expressed as hydrostatic or osmotic pressure differences per atmosphere across a semipermeable membrane. These polymers are described in U.S. Pat. Nos. 3,845,770, 3,916,899, and 4,160,020, and in Handbook of Common Polymers, Scott and Roff (1971) CRC Press, Cleveland, OH.

The semipermeable membrane may contain a flux-regulating agent. The flux-regulating agent means a substance added to assist in regulating the fluid permeability or flux through the semipermeable membrane. The flux-regulating agents include a substance which enhances the flux (hereinafter referred to as flux-enhancing agent) and a substance which decreases the flux (hereinafter referred to as flux-decreasing agent). The flux-enhancing agents are essentially hydrophilic, while the flux-decreasing agents are essentially hydrophobic. The flux-regulating agents include, for example, polyhydric alcohols, polyalkylene glycols, polyalkylenediols, polyesters of alkylen glycols, and the like.

Typical flux-enhancing agents include polyethylene glycols 300, 400, 600, 1500, 4000, 6000 and the like; low molecular weight glycols, such as polypropylene glycol, polybutylene glycol, and polyamylene glycol: polyalkylenediols, such as poly(1,3-propanediol), poly(1,4-butanediol), poly(1,6-hexanediol), and the like; fatty acids, such as 1,3-butylen glycol, 1,4-pentamethylene glycol, 1,4-hexamethylene glycol, and the like; alkylen triols, such as glycerine, 1,2,3-butanetriol, 1,2,4-hexanetriol, 1,3,6-hexanetriol, and the like; esters, such as ethylene glycol dipropionate, ethylene glycol butyrate, butylene glycol dipropionate, glycerol acetate esters, and the like. Preferred flux-enhancing agents include difunctional block-copolymers of propylene glycol, polyoxyalkylene or derivatives thereof, known as pluronics (trademark, BASF).

Typical flux-decreasing agents include phthalates substituted with an alkyl or alkoxy or with both an alkyl and alkoxy group such as diethyl phthalate, dimethoxyethyl phthalate, dimethyl phthalate, and [di(2-ethylhexyl) phthalate], and aryl phthalates such as triphenyl phthalate and butyl benzyl phthalate; insoluble salts such as calcium sulfate, barium sulfate, calcium phosphate, and the like; insoluble oxides such as titanium oxide; polymers in the form of powder, granules, and the like, such as polystyrene, polymethylmethacrylate, polycarbonate, and polysulfone; esters such as citric acid esters esterified with long chain alkyl groups; inert and water impermeable fillers; resins compatible with cellulose based semipermeable membrane forming materials; and the like.

The content of the flux-regulating agent contained in the semipermeable membrane is approximately 0.01 to approximately 20 W/W % or more.

Other substances may be contained in the semipermeable membrane to impart plasticity, flexibility, and elongation properties, to make the membrane less brittle, and to render tear strength. Such substances include phthalate plasticizers such as dibenzyl phthalate, dihexyl phthalate, butyl octyl phthalate, straight chain phthalates having 6 to 11 carbon atoms, di-isononyl phthalate, di-isodecyl phthalate, and the like. Other plasticizers include nonphthalates such as triacetin, dioctylazelate, epoxidized tallate, tri-isoctyl trimellitate, tri-isononyl trimellitate, sucrose acetate isobutyrate, epoxidized soybean oil, and the like.

The content of the plasticizer contained in the semipermeable membrane is approximately 0.01 to 20 W/W % or more.

The push layer is in contacting layered arrangement with the drug layer. The push layer contains an osmopolymer that imbibes an aqueous or biological fluid and swells to push compound A through the exit means of the formulation. The osmopolymer as used herein means a polymer that interacts with water or aqueous biological fluids and swells or expands to a high degree. Preferred osmopolymers are swellable and hydrophilic polymers exhibiting a 2 to 50-fold volume increase. The osmopolymer can be non-crosslinked or crosslinked, but is preferably at least lightly crosslinked in a preferred embodiment, to create an extended polymer network that is too large to exit the formulation. The content of the osmopolymer can be appropriately selected in accordance with various factors such as properties, content, and the like of a drug contained in the drug layer, but is not particularly limited, so long as it is an amount capable of releasing the drug from the drug layer at a desired dissolution rate by swelling. The amount is preferably 30 mg or more, more preferably 50 mg or more. The content is 40 to 80 W/W % with respect to the weight of the push layer.

The osmopolymers include one or more members selected from the group consisting of poly(alkylen oxide) having a number average molecular weight of 1,000,000 to 15,000,000, as represented by polyethylene oxide, and poly(alkali carboxymethylcellulose) having a number average molecular weight of 500,000 to 3,500,000, wherein the alkali is sodium, potassium, or lithium. The osmopolymers further include osmopolymers comprising polymers that form hydrogels, such as Carbopole (registered trademark), acidic carboxypolymers, polymers of acrylic cross-linked with polyallyl sucrose (known as carboxypolymethylene), and carboxyvinyl polymers having a molecular weight of 250,000 to 4,000,000; Cyanamer (registered trademark) polyacrylamides; cross-linked water swellable indenemaleic anhydride polymers; Good-rite (registered trademark) polyacrylic acid having a molecular weight of 80,000 to 200,000; Aqua-Keeps (registered trademark), acrylate polymer polysaccharides composed of condensed glucose units, such as diester cross-linked polygluran; and the like. Polymers that form hydrogels are described in U.S. Pat. Nos. 3,865,108, 4,002,173, and 4,207,893, and in Handbook of Common Polymers, Scott and Roff, Chemical Rubber Co., Cleveland, OH.

The osmoagent (sometimes referred to as an osmotic solute or an osmotically effective agent) may be contained in both of the drug layer containing compound A and the push layer, and is not particularly limited, so long as it exhibits an osmotic activity gradient across the semipermeable membrane. Suitable osmagents include a member or two or more members selected from the group consisting of sodium chloride, potassium chloride, lithium chloride, magnesium sulfate, magnesium chloride, potassium sulfate, sodium sulfate, lithium sulfate, potassium acid phosphate, mannitol, glucose, lactose, sorbitol, inorganic salts, organic salts, and carbohydrates. The content of the osmoagent used is 15 to 40 W/W % with respect to the weight of the push layer.

Solvents suitable for manufacturing the formulation components include aqueous or inert organic solvents that do not adversely harm the substances used in the system. Such solvents broadly include one or more members selected from the group consisting of aqueous solvents, alcohols, ketones, esters, ethers, aliphatic hydrocarbons, halogenated solvents, cycloaliphatic solvents, aromatic solvents, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts (such as sodium chloride, calcium chloride, and the like), and mixtures thereof (such as acetone and water, acetone and methanol, acetone and ethyl alcohol, methylene dichloride and methanol, and ethylene dichloride and methanol).

The drug layer is formed from a pharmaceutical composition consisting of compound A in an amount pharmacologically effective in treatment or prevention, and a carrier for a sustained release pharmaceutical composition. The carrier for a sustained release pharmaceutical composition may include hydrophilic polymers.

The hydrophilic polymers impart an action of releasing compound A at a constant releasing rate. Suitable hydrophilic polymers include poly(alkylene oxide) having a number average molecular weight of 100,000 to 750,000, such as poly(ethylene oxide), poly(methylene oxide), poly(buthylene oxide, and poly(hexylene oxide); and poly(carboxymethyl cellulose) having a number average molecular weight of 40,000 to 400,000, typically poly(alkali carboxymethyl cellulose), poly(sodium carboxymethyl cellulose), poly(potassium carboxymethyl cellulose), and poly(lithium carboxymethyl cellulose). The drug composition may contain hydroxypropylalkyl cellulose having a number average molecular weight of 9,200 to 125,000, typically hydroxypropylethyl cellulose, hypromellose, hydroxypropylbutyl cellulose, and hydroxypropylpentyl cellulose, to improve delivery properties of the formulation; and polyvinylpyrrolidone having a number average molecular weight of 7,000 to 75,000, to improve flow properties of the formulation. Among these polymers, poly(ethylene oxide) having a number average molecular weight of 100,000 to 300,000 is most preferable. The content of the hydrophilic polymer can be appropriately selected in accordance with various factors such as physicochemical properties, content, and the like of a drug contained, but is 40 to 90 W/W % with respect to the drug layer.

The drug layer may further contain surfactants and disintegrants, if desired. Suitable surfactants are those having an HLB value of approximately 10 to 25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate, and the like. Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum, and the like.

Pan coating may be used to prepare the completed formulation, except for the exit orifice for releasing a drug from the surface of the formulation. In the pan coating system, the composition for forming the semipermeable membrane is deposited by spraying the composition onto the surface of the bilayered compressed core formed from the drug layer and the push layer, accompanied by tumbling in a rotating pan. Alternatively, the compressed core may be coated with the semipermeable membrane by well-known techniques in the art. After the coating, the semipermeable membrane may be dried in a forced-air oven or in a temperature and humidity controlled oven to remove the solvent(s) used in the coating from the formulation. Drying conditions may be appropriately selected on the basis of an available equipment, ambient conditions, solvents, a coating agent, a coating thickness, and the like.

The osmotic pump type formulation, an embodiment of the pharmaceutical composition for modified release of the present invention, can be prepared by known conventional methods, such as wet granulation techniques. In the wet granulation, a drug and a carrier for a sustained release pharmaceutical composition are blended using an organic solvent, such as denatured absolute alcohol and the like, as a granulation solution. The remaining components may be dissolved in a portion of the granulation solution such as the above solvent, and a wet mixture separately prepared is gradually added to the drug mixture, accompanied by the continuous mixing in a blender. The granulation solution is added until a wet aggregate is generated, and the wet aggregate are sifted through a screen arranged on an oven tray. The mixture is dried at a temperature of approximately 24 to 35° C. in a forced-air oven for approximately 18 to 24 hours. The dried granules are sized. A lubricant such as magnesium stearate or the like is added to the drug granules, and the whole is put into a milling jar and mixed on a jar mill for approximately 10 minutes. The composition is pressed into a layer, for example, in a Manestye (registered trademark) press or a Korsch LCT press. For a bilayered core, the drug-containing layer is pressed, and a composition for the push layer, prepared in a similar fashion by wet granulation techniques, is pressed against the drug-containing layer. One exit orifice, or two more exit orifices, are drilled in the drug layer end of the formulation. Optional water soluble overcoats, which may be colored (for example, Opadry colored coatings) or clear (for example, Opadry Clear), may be coated on the formulation to provide the completed formulation.

The osmotic pump type formulation, an embodiment of the pharmaceutical composition for modified release of the present invention, has at least one exit orifice. A drug is constantly released from the formulation through the exit orifice(s) by the compressed core. The exit orifice may be provided during the manufacture of the formulation, or during the drug delivery by the formulation in a fluid environment of use. The terms "exit orifice", "delivery exit", "drug delivery exit", and similar terms as used herein include terms selected from the group consisting of pass, opening, orifice, and bore. Further, these expressions include an orifice that is formed from a substance or polymer that erodes, dissolves or is leached from the outer wall.

This substance or polymer may include, for example, erodible poly(glycolic acid) or poly(lactic acid) in the semipermeable membrane; gelatinous filaments; water-removable poly(vinyl alcohol); a leachable compound, such as a fluid removable pore-forming substance selected from the group consisting of inorganic and organic salts, oxides, and carbohydrates. The exit(s) are formed by leaching one or two or more members selected from the group consisting of sorbitol, lactose, fructose, glucose, mannose, galactose, talose, sodium chloride, potassium chloride, sodium citrate and mannitol to provide a uniform-release dimensioned pore-exit orifice(s). The exit can have any shape, such as round, rectangle, square, elliptical, and the like, for the uniform release of a drug from the formulation. The formulation can be constructed with one or two or more exits in spaced-apart relation or on one or more surfaces of the formulation. The pore size of the exit is not particularly limited, so long as it can cooperate with the compressed core to control the release of the drug, but is preferably 0.3 to 0.6 mm. Drilling, including mechanical and laser drilling, through the semipermeable membrane can be used to form the exit orifice. Such exits and equipments for forming such exits are disclosed in U.S. Pat. No. 3,916,899, by Theeuwes and Higuchi and in U.S. Pat. No. 4,088,864, by Theeuwes, et al., each of which is incorporated herein by reference.

(5) Formulation Utilizing Swelling Polymer

The formulation utilizing a swelling polymer, as an embodiment of the pharmaceutical composition for modified release of the present invention, is a formulation for modified release containing a water-soluble high molecular weight polymer which swells upon imbibition of water.

Formulation techniques using a swelling polymer which may be used in the formulation for modified release of the present invention are described in U.S. Pat. Nos. 6,340,475, 5,972,389, 5,582, 837, and 5,007,790, the contents of which are incorporated herein by reference.

The "water-soluble high molecular weight polymer which swells upon imbibition of water" used is not particularly limited, so long as it is a pharmaceutically acceptable polymer that swells in a dimensionally unrestricted manner upon imbibition of water, and that releases a drug continuously. Suitable polymers are those having a weight average molecular weight of preferably approximately 4,500,000 or more, more preferably approximately 4,500,000 to approximately 10,000,000, most preferably approximately 5,000,000 to approximately 8,000,000.

Such polymers include cellulose polymers and derivatives thereof, polysaccharides and derivatives thereof, polyalkylene oxides, and crosslinked polyacrylic acids and derivatives thereof. The term "cellulose" as used herein means a linear polymer of anhydroglucose. Preferred cellulose polymers are alkyl-substituted cellulose polymers that dissolve in the gastrointestinal tract. Preferred alkyl-substituted cellulose derivatives are those substituted with alkyl groups having 1 to 3 carbon atoms each. Examples thereof include, for example, methylcellulose, hydroxymethylcellulose, hydroxyethylcellulose, hydroxypropylcellulose, hypromellose, and carboxymethylcellulose. A preferred viscosity ranges between approximately 100 and approximately 110,000 cps, as measured in a 2% aqueous solution at 20° C. A viscosity in other embodiments ranges between approximately 1,000 and approximately 4,000 cps, as measured in a 2% aqueous solution at 20° C. More preferred alkyl-substituted celluloses are hydroxyethylcellulose and hypromellose. Preferred hydroxyethylcellulose is NATRASOL (product name) 250H X NF.

Further, most preferred polymers are polyalkylene oxide derivatives, particularly polyethylene oxide, i.e., an unsubstituted linear polymer of ethylene oxide. Preferred polyethylene oxide has a weight average molecular weight of approximately 900,000 to approximately 8,000,000. A preferred viscosity ranges between approximately 50 to approximately 2,000,000 cps, as measured in a 2% aqueous solution at 20° C. Preferred polyethylene oxide is POLYOX (product name), such as grade WSR Coagulant and grade WSR 303.

Other examples of such polymers include both naturally-occurring and modified (semi-synthetic) polysaccharide gums, such as dextran, xanthan gum, gellan gum, welan gum, and rhamsan gum. Xanthan gum is preferred. Cross-linked polyacrylic acids of greatest utility are those whose properties are the same as those described above for alkyl-substituted celluloses and polyalkylene oxide polymers. Preferred crosslinked polyacrylic acids are those with a viscosity ranging from approximately 4,000 to approximately 40,000 cps, for a 1% aqueous solution at 25° C. Preferred examples are CARBOPOL (product name) NF grades 971P, 974P, and 934P, and WATER LOCK (product name) which are starch/acrylates/acrylamide copolymers.

The content of the "water-soluble high molecular weight polymer which swells upon imbibition of water" with respect to the weight of the formulation is not particularly limited, but is preferably approximately 1 to approximately 95 W/W %.

The formulation utilizing a swelling polymer, an embodiment of the pharmaceutical composition for modified release of the present invention, can be prepared as a pharmaceutically acceptable solid dosage form for oral administration such as tablets, particles, and particles retained in tablets or capsules. A presently preferred dosage form is a size 0 gelatin capsule containing two or three polymer particles (pellets) containing a drug. For the two-pellet capsules, the pellets are cylindrically shaped, 6.6 or 6.7 mm (or more generally, 6.5 to 7 mm) in diameter and 9.5 or 10.25 mm (or more generally, 9 to 12 mm) in length. For the three-pellet capsules, the pellets are cylindrically shaped, 6.6 mm in diameter and 7 mm in length. For a size 00 gelatin capsule with two pellets, the pellets are cylindrical, 7.5 mm in diameter and 11.25 mm in length. For a size 00 gelatin capsule with three pellets, the pellets are cylindrical, 7.5 mm in diameter and 7.5 mm in length. Another presently preferred dosage form is a tablet, with dimensions 18 to 22 mm in length, 6.5 to 7.8 mm in width, and 6.2 to 7.5 mm in height, more preferably with dimensions 20 mm in length, 6.7 mm in width, and 6.4 mm in height. These are merely examples, and the shapes and sizes can be varied considerably.

A particulate drug/polymer mixture or a drug-impregnated polymer matrix can be prepared by various known conventional methods, such as mixing, comminution, and fabrication techniques. These methods include, for example, direct compression using appropriate punches and dies, injection, and compression molding. When compression molding is carried out, lubricants may be optionally added. Examples of lubricants include stearic acid, magnesium stearate, calcium stearate, sodium stearyl fumarate, and the like, and magnesium stearate is preferred. The content of the lubricant is 0.25 to 3 W/W %, preferably less than 1 W/W %, with respect to the weight of the formulation. As other lubricants, hydrogenated vegetable oils, and hydrogenated and refined triglycerides of stearic and palmitic acids are preferable, and the content is approximately 1 to 5 W/W %, preferably approximately 2 W/W %, with respect to the weight of the formulation.

Most preferable sets of various components described above include a combination of approximately 90 to approximately 97 W/W % (with respect to the weight of the formulation) of polyethylene oxide having a weight average molecular weight of approximately 2,000,000 to approximately 7,000,000 as the "water-soluble high molecular weight polymer which swells upon imbibition of water" and less than approximately 2 W/W % (with respect to the weight of the formulation) of magnesium stearate as the lubricant.

Examples of a combination of, for example, two water-soluble polymers include a combination of approximately 48 W/W % of polyethylene oxide having a weight average molecular weight of approximately 900,000 to approximately 7,000,000 and approximately 48 W/W % of hypromellose having a viscosity of approximately 3 to approximately 10,000 cps, as measured in a 2% aqueous solution at 20° C. (weight ratio=about 1:1).

It is expected that the formulation utilizing a swelling polymer is retained in the stomach by swelling.

(6) Matrix Formulation Utilizing Water-Soluble Polymer

The matrix formulation utilizing water-soluble polymer, an embodiment of the pharmaceutical composition for modified release of the present invention, is a formulation for modified release in which the drug is homogenously dispersed in one or more water-soluble polymers, such as hypromellose (HPMC).

Techniques for obtaining such a matrix formulation which may be used in the formulation for modified release according to the present invention are disclosed, for example, in WO 93/16686, the contents of which are incorporated herein by reference.

When hypromellose, a water-soluble polymer, is brought into contact with water, hydration thereof is caused, and a hydrogel layer is formed on the surface of a matrix. This gel layer containing a drug formed on the matrix surface is gradually dissolved and eroded, to release the drug from the layer. The matrix formulation of the present invention is characterized in that a drug may be controllably released by repeating the contact with water, the formation of the gel layer containing the drug, and the dissolution and erosion of the gel layer.

The matrix formulation of the present invention is characterized in that a sustained release filler consisting of a water-soluble polymer, an inactive diluent, and a physiologically active substance are homogenously dispersed. The water-soluble polymer is not particularly limited, so long as it is gradually gelled, eroded, dissolved, and/or disintegrated when exposed to an environmental fluid. Examples of the water-soluble polymers include, for example, hypromellose having a molecular weight of 1,000 to 4,000,000, hydroxymethyl cellulose, hydroxyethyl cellulose, hydroxypropyl cellulose having a molecular weight of 2,000 to 2,000,000, hypromellose phthalate having a labeled viscosity of 30 to 200 mm$^2$/s [at 20° C.; a 10% solution prepared by dissolving hypromellose phthalate in a methanol/dichloromethane mixture (1:1)], carboxyvinyl polymers, chitosans, mannans, galactomannans, xanthans, carageenans, amylose, alginic acid, salts and derivatives thereof, pectin, acrylates, aminoalkylmethacrylate copolymers, methacrylate copolymers, polyacid anhydrides, polyamino acids, poly(methylvinyl ether/maleic anhydride) polymers, polyvinyl alcohols, polyvinylpyrrolidone, glucans, scleroglucans, carboxymethyl cellulose and derivatives thereof, methyl cellulose, or conventional water-soluble cellulose derivatives.

Hypromellose having a molecular weight of 1,000 to 2,000,000, or carboxyvinyl polymers of 3,000 to 45,000 cps (at 25° C.; a 0.5% aqueous solution) is preferable, and hypromellose having a molecular weight of 10,000 to 1,000,000, or carboxyvinyl polymers of 4,000 to 40,000 cps (at 25° C.; a 0.5% aqueous solution) is more preferable. The content of the water-soluble polymer is 10 W/W % or more per formulation unit, preferably 30 W/W % or more, more preferably 70 W/W % or more. These water-soluble polymers may be contained alone or as a combination thereof in an appropriate amount(s).

Various fillers for medicaments may be appropriately used to prepare the matrix formulation of the present invention. The fillers for medicaments are not particularly limited, so long as they are pharmaceutically acceptable and may be used as additives for medicament. As the fillers, for example, a diluent, a binder, a disintegrator, an acidulant, an effervescent agent, an artificial sweetener, a flavor, a lubricant, a coloring agent, or the like may be used. The diluent may be selected from mannitol, lactose, starches derived from various organs, sorbitol, xylitol, citric acid, microcrystalline cellulose, and/or a diluent capable of generally promoting a penetration of water or an aqueous liquid into a pharmaceutical preparation. The binders include, for example, hypromellose, hydroxypropyl cellulose, polyvinyl alcohol, methyl cellulose, gum arabic, and the like. The disintegrators include, for example, a corn starch, a starch, carmellose calcium, carmellose sodium, low-substituted hydroxypropyl cellulose, and the like. The acidulants include, for example, citric acid, tartaric acid, malic acid, and the like. The effervescent agents include, for example, sodium bicarbonate and the like. The artificial sweeteners include, for example, saccharin sodium, dipotassium glycyrrhizinate, aspartame, *stevia*, thaumatin, and the like. The flavors include, for example, lemon, lemon-lime, orange, menthol, and the like. The lubricants include, for example, magnesium stearate, calcium stearate, sucrose fatty acid esters, polyethylene glycol, talc, stearic acid, and the like. These fillers for medicaments may be contained alone or as a combination thereof in an appropriate amount(s).

The matrix formulation of the present invention may be manufactured by a known method per se. In particular, tablets may be manufactured by a tablet forming method which is commonly used and known to those skilled in the art. The tabletting pressure is generally within a range of 3 to 20 kN. In a small scale, tablets may be prepared, in accordance with methods explained in detail in the following Examples, by preparing powder and/or granules with a mortar and a pestle, and forming the powder and/or granules into tablets by using an oil press tabletting machine.

(7) Modified Release Formulation with Coating Membrane

As a method for controlling the release (i.e., modified release) of a drug from a pharmaceutical preparation, a coating membrane is applied to the surface of a pharmaceutical preparation by coating. The kind of coating membrane is not particularly limited. The coating may be applied to not only a shaped preparation such as a tablet or the like, but also various preparations such as powder, granules, pellets, or the like.

A coating liquid may contain, for example, a membrane forming agent (mainly a polymer), a plasticizer (which provides plasticity, flexibility, and extensibility to a coating membrane), a water-soluble base (such as lactose, sodium chloride, or the like), a dispersing agent (which prevents particles or tablets from adhering and aggregating after the coating), or the like. These components may be dissolved or dispersed in an appropriate solvent, such as water, alcohol, or the like, to prepare the coating liquid.

The release of a drug from the formulation can be controlled by appropriately adjusting, for example, the kinds and the mixing ratio of components contained in the coating liquid, the amount of coating, or the like. For example, a preferable ratio of the membrane forming agent to the water-soluble base is 99:1 to 50:50 (membrane forming agent:water-soluble base). The content of the coating membrane is preferably approximately 2 to 30 parts by weight, with respect to 100 parts by weight of an uncoated tablet.

Examples of a coating method include, for example, a method in which a coating liquid, such as an organic solvent solution, or a mixing solution or suspension of an organic solvent and water, is sprayed while being rotated, by using a coating pan, or a method in which a coating liquid is sprayed while being fluidized by air blown from the bottom of a fluidized bed. Further, a coating liquid prepared by dissolving or dispersing a membrane forming agent in a solvent may be sprayed, and then the solvent may be removed by drying to form a coating membrane on the surface of a pharmaceutical preparation. As a simple method, a coating membrane may be formed by immersing shaped preparations or the like in a coating liquid.

Examples of the membrane forming agent as used herein include, for example, a water-insoluble polymer or a water-soluble polymer. The membrane forming agent is not particularly limited, so long as it is pharmaceutically acceptable and biocompatible. These membrane forming agents may be added alone or as a combination thereof in an appropriate amount(s).

Examples of the water-insoluble polymer include, for example, dibenzyl phthalate, dihexyl phthalate, butyl octyl phthalate, beeswax, carnauba wax, cetyl alcohol, cetyl stearyl alcohol, glyceryl behenate, lipids, fats, resins such as shellac or the like, cellulose derivatives such as ethyl cellulose, cellulose acetate, or the like, polyacrylate derivatives such as aminoalkylmethacryl copolymer (product name: Eudragit RS) or the like, polymethacrylate derivatives such as methacrylate copolymer (product name: Eudragit L) or the like, hydroxypropylmethyl cellulose acetate succinate, polylactic acid, polyglycolic acid, or the like.

Examples of the water-soluble polymer include, for example, hypromellose, hydroxypropyl cellulose, hydroxyethyl cellulose, carmellose sodium, methyl cellulose, polyvinylpyrrolidone, polyethylene glycol, polyvinyl alcohol, or the like.

To enhance the hydrophilic property of the coating membrane, a water-soluble base may be added. Examples of the water-soluble base include, for example, maltose, sucrose, lactose, sodium chloride, citric acid, polyethylene glycol 400, dextrose, fructose, xylitol, polyoxyethylene sorbitan monooleate, or the like.

The coating liquid which may be used in the present invention preferably contains one or more of the above-mentioned water-insoluble polymers, and more preferably further contains one or more of the water-soluble polymers and/or one or more of the water-soluble bases.

Further, the coating liquid may contain a plasticizer to provide plasticity, flexibility, and extensibility to the coating membrane. Examples of the plasticizer include, for example, triacetin, dioctyl azelate, epoxidized tallate, triisooctyl trimellitate, triisononyl trimellitate, sucrose acetate isobutyrate, soybean oil, propylene glycol, glycerol, polyethylene glycol, glyceryl triacetate (triacetin), triethyl citrate, acetyl triethyl citrate, diethyl phthalate, diethyl sebacate, dibutyl sebacate, acetylated monoglyceride, castor oil, liquid paraffin, or the like.

If desired, a surfactant and/or a disintegrator may be added. As such a surfactant which may be used in the coating membrane, a surfactant having an HLB value of approximately 10 to 25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate, or the like, may be used.

Examples of the disintegrator include, for example, starches, clay, cellulose, algin, gums, crosslinked starches, crosslinked cellulose, or crosslinked polymers. Typically, for example, corn starch, potato starch, croscarmellose, crospovidone, sodium starch glycorate, Veegum HV, methyl cellulose, agar, bentonite, carboxyl methyl cellulose, alginic acid, guar gum, or the like, may be used.

As a solvent suitable for manufacturing the formulation of the present invention, an aqueous or inert organic solvent which does not adversely affect substances used in the system may be used. Examples of the solvent include, for example, aqueous solvents, alcohols, ketones, esters, ethers, aliphatic hydrocarbons, halogenated solvents, cycloaliphatic, aromatic, or heterocyclic solvents, or a mixture thereof. Typical solvents may be, for example, acetone, diacetone alcohol, methanol, ethanol, isopropanol, butanol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, an aqueous solvent containing an inorganic salt such as sodium chloride, calcium chloride, or the like, or a mixture thereof, such as a mixture of acetone and water, a mixture of acetone and methanol, a mixture of acetone and ethanol, a mixture of methylene dichloride and methanol, or a mixture of ethylene dichloride and methanol.

(8) Matrix Formulation Utilizing Insoluble Polymer

A matrix formulation utilizing an insoluble polymer, an embodiment of the present invention, is a pharmaceutical composition for modified release in which the drug is uniformly dispersed in a water-insoluble polymer. Because the matrix consisting of the water-insoluble polymer can control the penetration of water into the formulation, the matrix formulation can modify the release of the drug from the formulation by controlling the dissolution rate of the drug in the matrix and the dispersion rate of the dissolved drug in the matrix.

The water-insoluble polymer used in the present invention is not particularly limited, so long as it is pharmaceutically acceptable. Examples of the water-insoluble polymer include, for example, dibenzyl phthalate, dihexyl phthalate, butyl octyl phthalate, beeswax, carnauba wax, cetyl alcohol, cetyl stearyl alcohol, glyceryl behenate, lipids, fats, resins such as shellac or the like, cellulose derivatives such as ethyl cellulose, cellulose acetate, or the like, polyacrylate derivatives such as aminoalkylmethacryl copolymer or the like, polymethacrylate derivatives such as methacrylate copolymer, ethyl acrylate methyl methacrylate copolymer or the like, hydroxypropylmethyl cellulose acetate succinate, polylactic acid, polyglycolic acid, or the like.

The content of the insoluble polymer is 1 W/W % or more per formulation unit, preferably 2 W/W % or more, more preferably 5 W/W % or more. These insoluble polymers may be contained alone or as a combination thereof in an appropriate amount(s).

Various fillers for medicaments may be appropriately used to prepare the matrix formulation of the present invention. The fillers for medicaments are not particularly limited, so long as they are pharmaceutically acceptable and may be used as additives for medicament. As the fillers, for example, a diluent, a binder, a disintegrator, an acidulant, an effervescent agent, an artificial sweetener, a flavor, a lubricant, a coloring agent, or the like may be used. The diluent may be selected from mannitol, lactose, starches derived from various organs, sorbitol, xylitol, citric acid, microcrystalline cellulose, and/or a diluent capable of generally promoting a penetration of water or an aqueous liquid into a pharmaceutical preparation. The binders include, for example, hypromellose, hydroxypropyl cellulose, polyvinyl alcohol, methyl cellulose, gum arabic, and the like. The disintegrators include, for example, a corn starch, a starch, carmellose calcium, carmellose sodium, low-substituted hydroxypropyl cellulose, and the like. The acidulants include, for example, citric acid, tartaric acid, malic acid, and the like. The effervescent agents include, for example, sodium bicarbonate and the like. The artificial sweeteners include, for example, saccharin sodium, dipotassium glycyrrhizinate, aspartame, *stevia*, thaumatin, and the like. The flavors include, for example, lemon, lemon-lime, orange, menthol, and the like. The lubricants include, for example, magnesium stearate, calcium stearate, sucrose fatty acid esters, polyethylene glycol, talc, stearic acid, and the like. These fillers for medicaments may be contained alone or as a combination thereof in an appropriate amount(s).

The matrix formulation of the present invention may be manufactured by a known method per se. In particular, tablets may be manufactured by a tablet forming method which is commonly used and known to those skilled in the art. The tabletting pressure is generally within a range of 3 to 20 kN. In a small scale, tablets may be prepared, in accordance with methods explained in detail in the following Examples, by preparing powder and/or granules with a mortar and a pestle, and forming the powder and/or granules into tablets by using an oil press tabletting machine.

EXAMPLES

The present invention will now be further illustrated by, but is by no means limited to, the following Examples.

In the following Examples, unless otherwise noted, a compound produced according to Example 41 of WO 99/20607 was used as compound A.

Example 1: Preparation of Sustained Release Hydrogel-Forming Formulation

In this Example, as the pharmaceutical composition for modified release of the present invention, sustained release hydrogel-forming formulations 1A to 1C were prepared.

Example 1A 400 g of the compound A, 100 g of polyethylene oxide, 291.2 g of polyethylene glycol, 0.8 g of finely ground dibutyl hydroxytoluene (BHT) (manufactured by Merck, the same was used hereinafter), and 8 g of magnesium stearate were weighed out, and mixed by using a mixer. The mixture was compression-molded by using Roller Compactor Mini (manufactured by Freund Corporation; the same apparatus was used hereinafter) and sieved to obtain a pharmaceutical composition for modified release (granules) of the present invention. The obtained granules were formed into tablets by using a rotary tabletting machine (manufactured by HATA IRON WORKS CO., LTD.; the same apparatus was used hereinafter) to obtain 400 mg/tablet of a pharmaceutical composition for modified release (tablet) of the present invention. The obtained tablet was coated with a film coating agent dispersed in water (Opadry, manufactured by Colorcon, Inc., the same was used hereinafter) by using High coater (HCT-30, manufactured by Freund Corporation, the same apparatus was used hereinafter) to obtain a pharmaceutical composition for modified release (tablet) of the present invention.

Example 1B 400 g of the compound A, 250 g of polyethylene oxide, 190.7 g of polyethylene glycol, 0.8 g of finely ground BHT, and 8.5 g of magnesium stearate were weighed out, and mixed by using a mixer. The mixture was compression-molded by using Roller Compactor Mini, and then sieved to obtain a pharmaceutical composition for modified release (granules) of the present invention. The obtained granules were formed into tablets by using a rotary tabletting machine to obtain 425 mg/tablet of a pharmaceutical composition for modified release (tablet) of the present invention. The obtained tablet was coated with a film coating agent dispersed in water by using High coater to obtain a pharmaceutical composition for modified release (tablet) of the present invention.

Example 1C

Into a fluidized bed granulating apparatus GPCG-5 (manufactured by Freund Corporation; the same apparatus was used hereinafter), 800 g of de-lumped compound A, 1120 g of polyethylene oxide, 1913.6 g of polyethylene glycol, and 120 g of hydroxypropylcellulose (HPC-SL, manufactured by Nippon Soda Co., Ltd.,) were loaded, and granulated with purified water to obtain a pharmaceutical composition for modified release (granules) of the present invention. The pharmaceutical composition for modified release (granules) of the present invention was sieved, and mixed with 6.4 g of finely ground BHT and 40 g of magnesium stearate, and the obtained mixture was formed into tablets by using the rotary tabletting machine to obtain a pharmaceutical composition for modified release (tablet) of the present invention having a weight per tablet of 250 mg. The obtained tablets were spray-coated with an aqueous dispersion of the film coating agent using HiCoater to obtain a pharmaceutical composition for modified release (tablet) of the present invention having a weight per tablet of 257.5 mg.

Comparative Example 1

After 400 g of de-lumped compound A was mixed with 1200 g of D-mannitol, 320 g of purified water was added thereto, and the mixture was kneaded by using an agitation granulator (VG-25, manufactured by Powrex Corporation). The resulting product was sieved through a screen (opening: 850 μm), and dried by using a fluidized bed granulating apparatus (FLO-1, manufactured by Freund Corporation). The dried product was sieved through a screen (opening: 500 μm), and then filled into No. 1 capsules at a content of 320 mg per capsule to obtain a pharmaceutical composition of Comparative Example containing 80 mg of compound A.

Example 2: Preparation of Multi-Layered Formulation Consisting of Drug Core and Release-Controlling Layer which are Geometrically Arranged In the Examples (Examples 2A to 2D), as the pharmaceutical composition for modified release of the present invention, multi-layered formulations 2A to 2D were prepared.

Step 1: Production of Mixed Powder Constituting Layer 2 Containing Active Substance A mixed powder containing 50.0 mg of compound A and the composition unit shown in Table 1 was produced, and used in producing layer 2 as the intermediate layer of the three-layered tablet. The powder composed of the composition unit was prepared by weighing out necessary amounts of the active substance (compound A), mannitol, Hypromellose (90SH-15000, manufactured by Shin-Etsu Chemical Co. Ltd), polyvinyl pyrrolidone, microcrystalline cellulose, and magnesium stearate, and mixing them with a mortar and a pestle so that they were homogenized.

TABLE 1

| | |
|---|---|
| Compound A | 50.0 mg |
| Mannitol | 15.0 mg |
| Hypromellose (90SH-15000) | 15.0 mg |
| Polyvinyl pyrrolidone | 4.8 mg |
| Microcrystalline cellulose | 63.7 mg |
| Magnesium stearate | 1.5 mg |
| Total | 150.0 mg |

Step 2: Production of Granules Constituting Layers 1 and 3 (Layers 1 and 3 Containing No Drug) Used for Modified Release of Drug Granules made with the composition ratio shown in Table 2 were produced and used in producing layer 1 as the top layer and layer 3 as the bottom layer of the three-layered tablet. Specifically, the granules were prepared by weighing out necessary amounts of hypromellose, hydrogenated castor oil, yellow iron oxide, and magnesium stearate; mixing them by the use of a mortar and a pestle so that they were homogenized; further moistening them with a solution of ethylcellulose in alcohol (10% w/w); and drying the homogeneously wet aggregate.

TABLE 2

| | |
|---|---|
| Hypromellose (90SH-15000) | 80.25% |
| Hydrogenated castor oil | 13.50% |
| Yellow iron oxide | 0.25% |
| Ethylcellulose | 5.00% |
| Magnesium stearate | 1.00% |
| Total | 100.00% |

Step 3: Production of Three-Layered Tablet (Compression Molding)

Three-layered tablet were prepared by an oil press tabletting machine with a tabletting pressure of 1000 kg/punch. The granules of layer 3 prepared in Step 2 were put into a die, and subjected to light tapping so that the upper surface became flat. On the surface, the mixed powder of layer 2 containing the active substance prepared in Step 1 was loaded, which was subjected to light tapping so that the upper surface became flat. Furthermore, on the surface, the granules of the layer 1 prepared in the Step 2 were loaded into the die, and subjected to compression molding. Thus, three-layered tablets containing 50 mg of compound A (2A to 2D) were produced.

The weight and the punch diameter of each of layers 1, 2, and 3 in each of multi-layered formulations 2A to 2D are shown in Table 3.

TABLE 3

|  | Examples | | | |
| --- | --- | --- | --- | --- |
|  | 2 A | 2 B | 2 C | 2 D |
| Layer 1 | 100.0 | 100.0 | 100.0 | 100.0 |
| Layer 2 | 150.0 | 300.0 | 150.0 | 150.0 |
| Layer 3 | 150.0 | 150.0 | 150.0 | 150.0 |
| Total (mg) | 400.0 | 550.0 | 400.0 | 400.0 |
| Punch diameter (mm) | 8 | 8 | 7 | 6.5 |

Example 3: Preparation of Gel Formulation in which a Plurality of Gums is Combined In this Example, as the pharmaceutical composition for modified release of the present invention, a gel formulation composed of the composition unit shown in Table 4 was prepared.

Specifically, necessary amounts of locust bean gum (GENUGUM type RL-200-J, manufactured by Sansho Co., Ltd.), xanthan gum (VS-900, manufactured by Nitta Gelatin Inc.), dextrose, and calcium sulfate were weighed out, and mixed sufficiently by using a mortar and a pestle so that the mixture was homogenized. Furthermore, an appropriate amount of purified water was added thereto, and the mixture was stirred and mixed. The mixture was sieved through a screen, and the obtained product was dried. To the dried product, a necessary amount of compound A was added. To the mixture, a solution of ethylcellulose in alcohol (100 mg/mL) was gradually added. The mixture was dried, and the dried product was put into a die, and subjected to compression molding by an oil press tabletting machine with a tabletting pressure of 1000 kg/punch by using a punch having a diameter of 8 mm.

TABLE 4

| Compound A | 50.0 mg |
| --- | --- |
| Locust bean gum (GENUGUM type RL-200-J) | 50.0 mg |
| Xanthan gum (VS-900) | 50.0 mg |
| Dextrose | 70.0 mg |
| Calcium sulfate | 10.0 mg |
| Ethylcellulose | 14.0 mg |
| Total | 244.0 mg |

Example 4: Preparation of Osmotic Pump Type Formulation

In this Example, as the pharmaceutical composition for modified release of the present invention, an osmotic pump type formulation was prepared.

Step 1: Production of Mixed Powder Constituting Drug Layer Containing Active Substance Mixed powder containing 50.0 mg of compound A and the composition unit shown in Table 5 was produced, and it was used in producing a bilayered compressed core.

The powder composed of the composition unit was prepared by weighing out necessary amounts of active substance (compound A), polyethylene oxide (Polyox WSR N-80, manufactured by DOW), hypromellose (TC-5 R, manufactured by Shin-Etsu Chemical Co. Ltd.), and magnesium stearate, and mixing them sufficiently by using a mortar and a pestle so that they were homogenized.

TABLE 5

| Compound A | 50.0 mg |
| --- | --- |
| Polyethylene oxide (Polyox WSR N-80) | 100.0 mg |
| Hypromellose (TC-5 R) | 6.0 mg |
| Magnesium stearate | 1.0 mg |
| Total | 157.0 mg |

Step 2: Production of Mixed Powder Constituting Push Layer

A mixed powder composed of the composition unit shown in Table 6 was produced, and it was used in producing the bilayered compressed core.

Specifically, the mixed powder was produced by weighing out necessary amounts of polyethylene oxide (Polyox WSR Coagulant, manufactured by DOW), sodium chloride, hypromellose, red ferric oxide, and magnesium stearate, and mixing them sufficiently by using a mortar and a pestle so that they were homogenized.

TABLE 6

| Polyethylene oxide (Polyox WSR Coagulant) | 60.0 mg |
| --- | --- |
| Sodium chloride | 30.0 mg |
| Hypromellose (TC-5 R) | 4.0 mg |
| Red ferric oxide | 1.0 mg |
| Magnesium stearate | 0.5 mg |
| Total | 95.5 mg |

Step 3: Production of Bilayered Compressed Core Composed of Drug Layer and Push Layer A bilayered compressed core was prepared by an oil press tabletting machine with a tabletting pressure of 1000 kg/punch. The mixed powder for a push layer prepared in Step 2 was put into a die, the mixed powder for a drug layer prepared in Step 1 was loaded thereon, and the both layers were subjected to compression molding to produce a bilayered compressed core containing 50 mg of compound A.

Step 4: Production of Semi-Permeable Membrane and Membrane Coating

Necessary amounts of polyethylene glycol 4000 and cellulose acetate (mass ratio of 6:94) were dissolved in a mixed solvent of dichloromethane and methanol (mass ratio of 9:1) to prepare a coating solution having a solid concentration of 2% w/w. By using this solution, a film coating was formed so that the coating component was 5% w/w with respect to the bilayered compressed core.

Step 5: Punching

A needle (27G) having a diameter of 0.4 mm was used to form orifices at the drug layer side of the semi-permeable-membrane-coated tablets prepared in Step 4, to prepare an osmotic pump type formulation as the pharmaceutical composition for modified release of the present invention.

Example 5: Preparation of Formulation Using Swelling Polymer

In the Examples (Examples 5A to 5C), as the pharmaceutical composition for modified release of the present invention, formulations 5A to 5C using a swelling polymer composed of the composition unit shown in Table 7 were prepared.

Specifically, necessary amounts of compound A and polyethylene oxide (various types of Polyox, manufactured by DOW) were weighed out, and mixed sufficiently by using a mortar and a pestle so that they were homogenized. The mixture was put into a die and subjected to compression molding by an oil press tabletting machine with a tabletting pressure of 1000 kg/punch by using a punch having a diameter of 7 mm.

TABLE 7

|  | Examples | | |
|---|---|---|---|
|  | 5 A | 5 B | 5 C |
| Compound A | 50.0 | 50.0 | 50.0 |
| Polyethylene oxide (Polyox WSR N-60K) | 200.0 | — | — |
| Polyethylene oxide (Polyox WSR N-12K) | — | 200.0 | — |
| Polyethylene oxide Polyox WSR N-205) | — | — | 200.0 |
| Total (mg) | 250.0 | 250.0 | 250.0 |

Example 6: Preparation of Matrix Formulation Using Water-Soluble Polymer

In the Examples (Examples 6A to 6N), as the pharmaceutical composition for modified release of the present invention, matrix formulations 6A to 6N composed of the composition units shown in Tables 8 and 9 were prepared.

Specifically, necessary amounts of compound A and various additives [hypromellose (manufactured by Shin-Etsu Chemical Co. Ltd) or hydroxypropylcellulose (manufactured by Nippon Soda Co., Ltd.)] were weighed out, and mixed sufficiently by using a mortar and a pestle so that they were homogenized. The mixture was put into a die and subjected to compression molding by an oil press tabletting machine with a tabletting pressure of 1000 kg/punch.

TABLE 8

| Examples | 6 A | 6 B | 6 C | 6 D | 6 E | 6 F |
|---|---|---|---|---|---|---|
| Compound A | 100.0 | 100.0 | 100.0 | 100.0 | 100.0 | 100.0 |
| Hypromellose (METLOSE SR 90SH-100SR) | 200.0 | — | — | 50.0 | — | — |
| Hypromellose (METLOSE SR 90SH-4000SR) | — | 200.0 | — | — | 25.0 | — |
| Hypromellose (METLOSE SR 90SH-15000SR) | — | — | 200.0 | — | — | 25.0 |
| Total (mg) | 300.0 | 300.0 | 300.0 | 150.0 | 125.0 | 125.0 |

TABLE 9

| Examples | 6 G | 6 H | 6 I | 6 J | 6 K | 6 L | 6 M | 6 N |
|---|---|---|---|---|---|---|---|---|
| Compound A | 100.0 | 100.0 | 100.0 | 100.0 | 100.0 | 100.0 | 100.0 | 100.0 |
| Hydroxypropyl cellulose (HPC-L) | — | — | — | — | 50.0 | — | — | — |
| Hydroxypropyl cellulose (HPC-M) | 200.0 | — | 100.0 | 50.0 | — | 25.0 | — | — |
| Hydroxypropyl cellulose (HPC-H) | — | 200.0 | — | — | — | — | 25.0 | 10.0 |
| Total (mg) | 300.0 | 300.0 | 200.0 | 150.0 | 150.0 | 125.0 | 125.0 | 110.0 |

Example 7: Preparation of Modified Release Formulation with Coating Membrane In the Examples (Examples 7A to 7E), as the pharmaceutical composition for modified release of the present invention, modified release formulations 7A to 7E with a coating membrane composed of the composition unit shown in Table 10 were prepared.

Specifically, firstly, necessary amounts of the compound A and additives of a core tablet were weighed out, and mixed sufficiently by using a mortar and a pestle so that they were homogenized. The mixture was put into a die and subjected to compression molding by an oil press tabletting machine with a tabletting pressure of 1000 kg/punch to produce each core tablet. Additionally, necessary amounts of film coating components [as aminoalkyl methacrylate copolymer RS, various types of Eudragit, manufactured by Degussa corporation; and as Hypromellose, TC-5 E manufactured by Shin-Etsu Chemical Co. Ltd] were dissolved/dispersed in ethanol to prepare each coating solution having a solid concentration of 10% w/w. By using each solution, film coating was conducted so that the coating component had a prescribed amount with respect to the core tablet.

TABLE 10

|  | Examples | | | | |
|---|---|---|---|---|---|
|  | 7 A | 7 B | 7 C | 7 D | 7 E |
| Core tablet | | | | | |
| Compound A | 100.0 | 100.0 | 100.0 | 100.0 | 100.0 |
| Mannitol | 100.0 | — | — | — | — |
| Polyethylene glycol 8000 | — | 200.0 | 200.0 | 200.0 | 200.0 |
| Subtotal (mg) | 200.0 | 300.0 | 300.0 | 300.0 | 300.0 |
| Film coat | | | | | |
| Aminoalkyl methacrylate Copolymer RS (Eudragit RL PO) | — | — | 15.0 | 30.0 | 22.5 |
| Aminoalkyl methacrylate Copolymer RS (Eudragit RS PO) | 10.0 | 12.0 | — | — | — |
| Hypromellose (TC-5 E) | — | — | — | — | 7.5 |
| Subtotal (mg) | 10.0 | 12.0 | 15.0 | 30.0 | 30.0 |
| Total (mg) | 210.0 | 312.0 | 315.0 | 330.0 | 330.0 |

Example 8: Preparation of Matrix Formulation Using Insoluble Polymer

Examples 8A to 8C

As the pharmaceutical composition for modified release of the present invention, matrix formulations (tablets) 8A to 8C composed of the composition unit shown in Table 11 were prepared.

Specifically, necessary amounts of the compound A and ethylcellulose (Ethocel 10 premium, manufactured by DOW) were weighed out, and mixed sufficiently by using a mortar and a pestle so that they were homogenized. The mixture was put into a die and subjected to compression molding by an oil press tabletting machine with a tabletting pressure of 1000 kg/punch.

TABLE 11

|  | Examples | | |
| --- | --- | --- | --- |
|  | 8 A | 8 B | 8 C |
| Compound A | 100.0 | 100.0 | 100.0 |
| Ethylcellulose (Ethocel 10 premium) | 200.0 | 25.0 | 10.0 |
| Total (mg) | 300.0 | 125.0 | 110.0 |

Examples 8D and 8E

As the pharmaceutical composition for modified release of the present invention, matrix formulations (granules) 8D to 8E composed of the composition unit shown in Table 12 were prepared.

Specifically, necessary amounts of the compound A and ethylcellulose shown in Table 12 were weighed out, and mixed sufficiently by using a mortar and a pestle so that they were homogenized. Furthermore, an appropriate amount of ethanol was added thereto, and the mixture was stirred and mixed. The mixture was dried, and screened by using a sieve so as to remove coarse particles to prepare granule formulations 8D and 8E for modified release as the pharmaceutical composition for modified release of the present invention.

TABLE 12

|  | Examples | |
| --- | --- | --- |
|  | 8 D | 8 E |
| Compound A | 25.0 | 50.0 |
| Ethylcellulose | 75.0 | 100.0 |
| Total (mg) | 100.0 | 150.0 |

Examples 8F and 8G

Necessary amounts of the compound A and microcrystalline cellulose shown in Table 13 were weighed out, and mixed sufficiently by using a mortar and a pestle so that they were homogenized. Furthermore, a prescribed amount of solution of ethylcellulose in ethanol was added thereto, and the mixed solution was stirred and mixed. The mixture was dried and screened by using a sieve so as to remove coarse particles to prepare granule formulations 8F and 8G for modified release as the pharmaceutical composition for modified release of the present invention.

TABLE 13

|  | Examples | |
| --- | --- | --- |
|  | 8 F | 8 G |
| Compound A | 50.0 | 50.0 |
| Microcrystalline cellulose | — | 50.0 |
| Ethylcellulose | 8.0 | 10.0 |
| Total (mg) | 58.0 | 110.0 |

Experimental Example 1: Dissolution Test of Sustained Release Hydrogel-Forming Formulation A drug release property from each of the formulations prepared in Examples 1A to 1C was evaluated by the dissolution test, method 2 (paddle method) described in the Japanese Pharmacopoeia. The test was carried out using 900 mL of a USP phosphate buffer (pH 6.8) as a test solution at a paddle rotating speed of 200 rpm. The drug concentration in the test solution was measured every hour, and the drug release property was evaluated. The results are shown in Table 14 and FIG. 1.

TABLE 14

|  | Examples | | |
| --- | --- | --- | --- |
|  | 1 A | 1 B | 1 C |
| Dissolution rate 1.5 hours | 54 | 15 | 27 |
| Dissolution rate 2.5 hours | 80 | 31 | 52 |
| Dissolution rate 7 hours | 99 | 66 | 95 |

Figure 2:
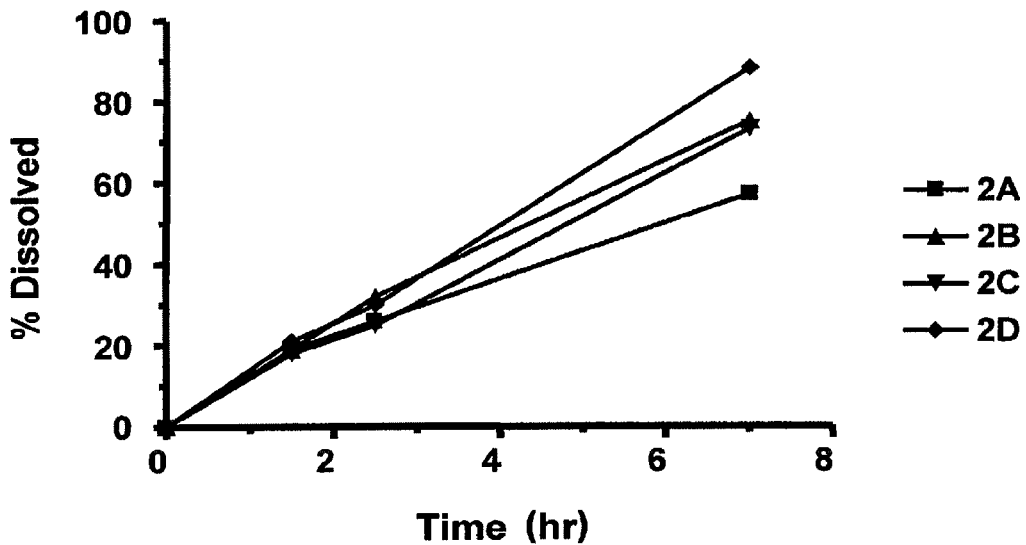
FIG. 2 is a graph showing the drug release property from each of the formulations prepared in Examples 2A to 2D in Experimental Example 2.

Experimental Example 2: Dissolution Test of Multi-Layered Formulation Consisting of Drug Core and Release-Controlling Layer which are Geometrically Arranged A drug release property from each of the formulations prepared in Examples 2A to 2D was evaluated by the method described in Experimental Example 1. The results are shown in Table 15 and FIG. 2.

TABLE 15

|  | Examples | | | |
| --- | --- | --- | --- | --- |
|  | 2 A | 2 B | 2 C | 2 D |
| Dissolution rate 1.5 hours | 19 | 19 | 18 | 21 |
| Dissolution rate 2.5 hours | 26 | 32 | 25 | 30 |
| Dissolution rate 7 hours | 57 | 75 | 73 | 88 |

Figure 3:
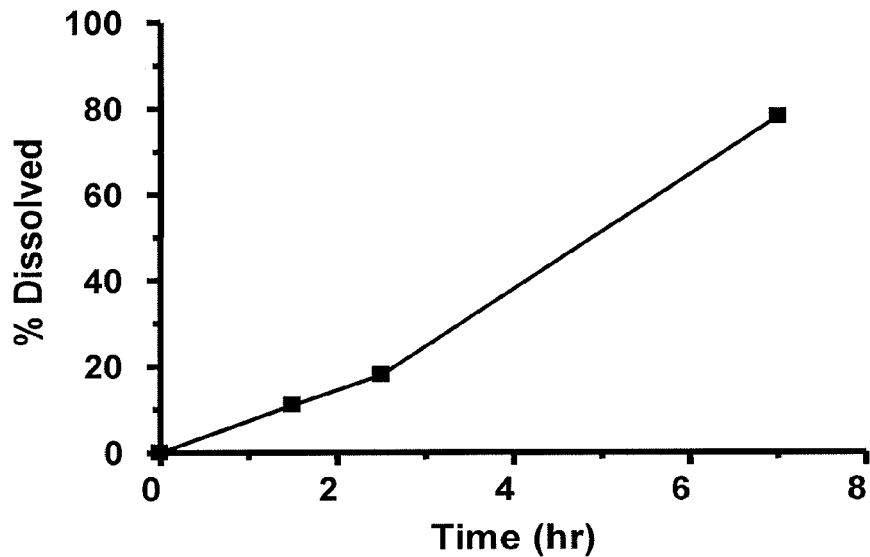
FIG. 3 is a graph showing the drug release property from the formulation prepared in Example 3 in Experimental Example 3.

Experimental Example 3: Dissolution Test of Gel Formulation in which a Plurality of Gums is Combined A drug release property from the formulation prepared in Example 3 was evaluated by the method described in Experimental Example 1. The results are shown in FIG. 3. As a result, the dissolution rates after 1.5 hours, 2.5 hours, and 7 hours were 11%, 18%, and 78%, respectively.

Experimental Example 4: Dissolution Test of Osmotic Pump Type Formulation

Figure 4:
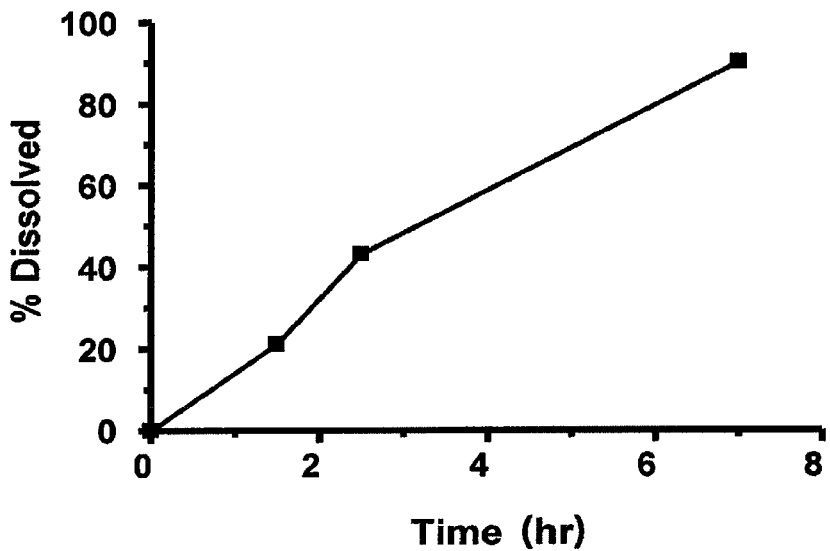
FIG. 4 is a graph showing the drug release property from the formulation prepared in Example 4 in Experimental Example 4.

A drug release property from the formulation prepared in Example 4 was evaluated by the method described in Experimental Example 1. The results are shown in FIG. 4. As a result, the dissolution rates after 1.5 hours, 2.5 hours, and 7 hours were 21%, 43%, and 90%, respectively.

Experimental Example 5: Dissolution Test of Formulation Using Swelling Polymer

Figure 5:
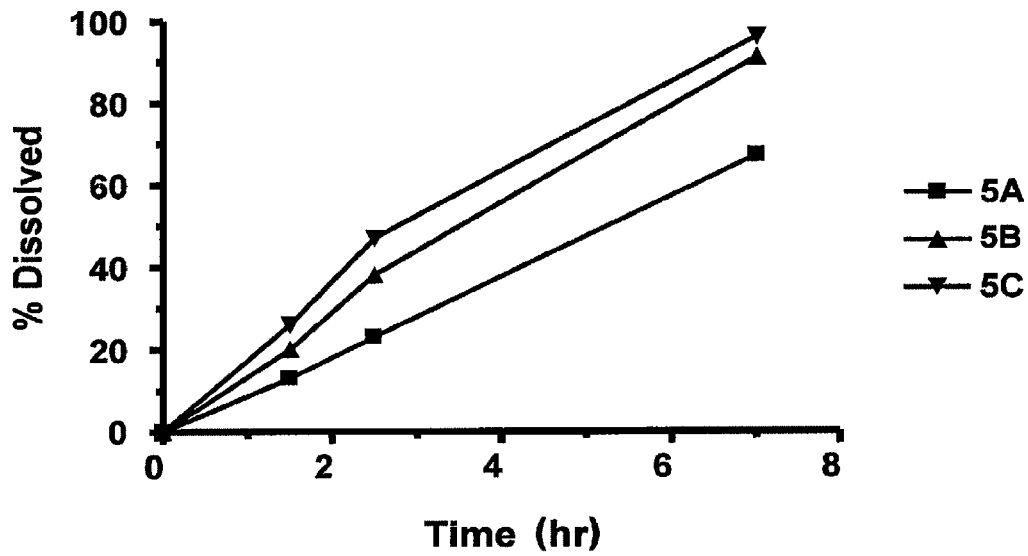
FIG. 5 is a graph showing the drug release property from each of the formulations prepared in Examples 5A to 5C in Experimental Example 5.

A drug release property from each of the formulations prepared in Examples 5A to 5C was evaluated by the method described in Experimental Example 1. The results are shown in Table 16 and FIG. 5.

TABLE 16

|  | Examples | | |
|---|---|---|---|
|  | 5 A | 5 B | 5 C |
| Dissolution rate 1.5 hours | 13 | 20 | 26 |
| Dissolution rate 2.5 hours | 23 | 38 | 47 |
| Dissolution rate 7 hours | 67 | 91 | 96 |

Figure 6:
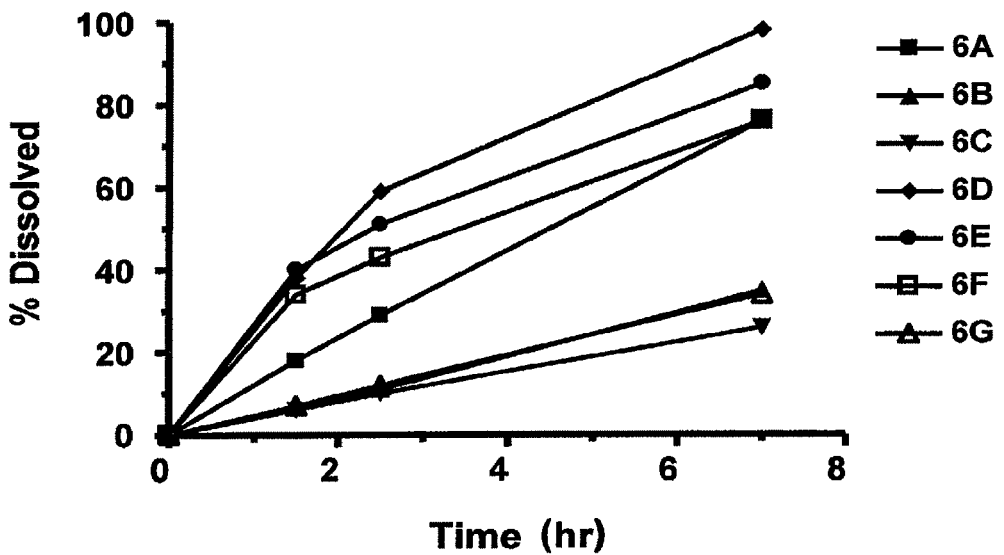
FIG. 6 is a graph showing the drug release property from each of the formulations prepared in Examples 6A to 6G in Experimental Example 6.
Figure 7:
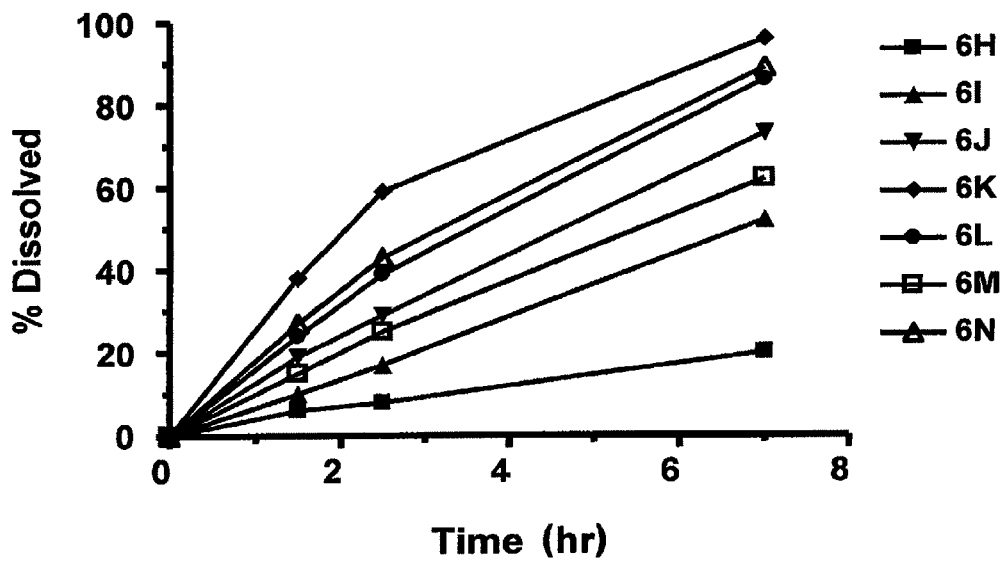
FIG. 7 is a graph showing the drug release property from each of the formulations prepared in Examples 6H to 6N in Experimental Example 6.

Experimental Example 6: Dissolution Test of Matrix Formulation Using Water-Soluble Polymer A drug release property from each of the formulations prepared in Examples 6A to 6N was evaluated by the method described in Experimental Example 1. The results are shown in Tables 17 and 18 and FIGS. 6 and 7.

TABLE 17

| Examples | 6 A | 6 B | 6 C | 6 D | 6 E | 6 F | 6 G |
|---|---|---|---|---|---|---|---|
| Dissolution rate 1.5 hours | 18 | 7 | 6 | 38 | 40 | 34 | 7 |
| Dissolution rate 2.5 hours | 29 | 11 | 10 | 59 | 51 | 43 | 12 |
| Dissolution rate 7 hours | 76 | 35 | 26 | 98 | 85 | 76 | 34 |

TABLE 18

| Examples | 6 H | 6 I | 6 J | 6 K | 6 L | 6 M | 6 N |
|---|---|---|---|---|---|---|---|
| Dissolution rate 1.5 hours | 6 | 10 | 19 | 38 | 24 | 15 | 27 |
| Dissolution rate 2.5 hours | 8 | 17 | 29 | 59 | 39 | 25 | 43 |
| Dissolution rate 7 hours | 20 | 52 | 73 | 96 | 86 | 62 | 89 |

Figure 8:
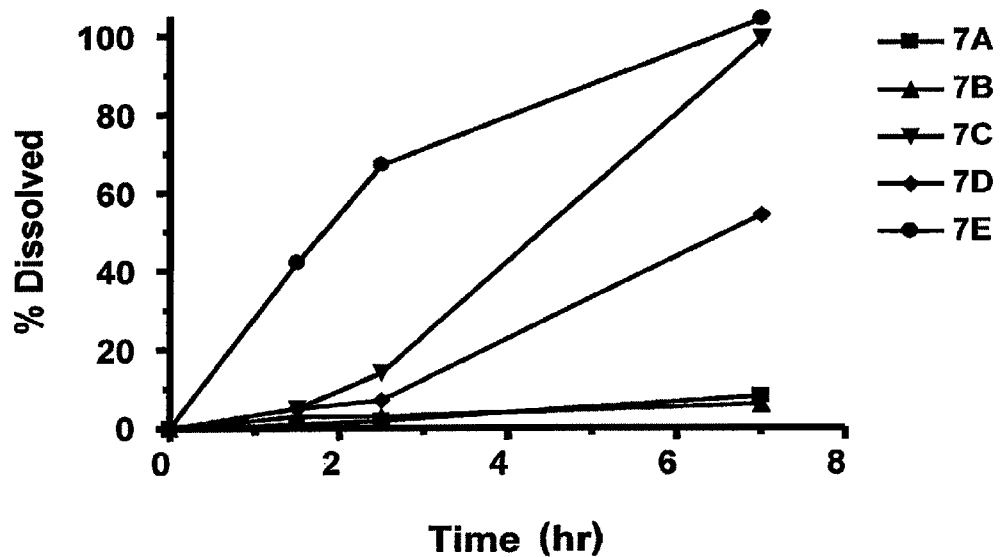
FIG. 8 is a graph showing the drug release property from each of the formulations prepared in Examples 7A to 7E in Experimental Example 7.

Experimental Example 7: Dissolution Test of Modified Release Formulation with Coating Membrane A drug release property from each of the formulations prepared in Examples 7A to 7E was evaluated by the method described in Experimental Example 1. The results are shown in Table 19 and FIG. 8.

TABLE 19

|  | Examples | | | | |
|---|---|---|---|---|---|
|  | 7 A | 7 B | 7 C | 7 D | 7 E |
| Dissolution rate 1.5 hours | 1 | 3 | 5 | 5 | 42 |

TABLE 19-continued

|  | Examples | | | | |
|---|---|---|---|---|---|
|  | 7 A | 7 B | 7 C | 7 D | 7 E |
| Dissolution rate 2.5 hours | 2 | 3 | 14 | 7 | 67 |
| Dissolution rate 7 hours | 8 | 6 | 99 | 54 | 104 |

Figure 9:
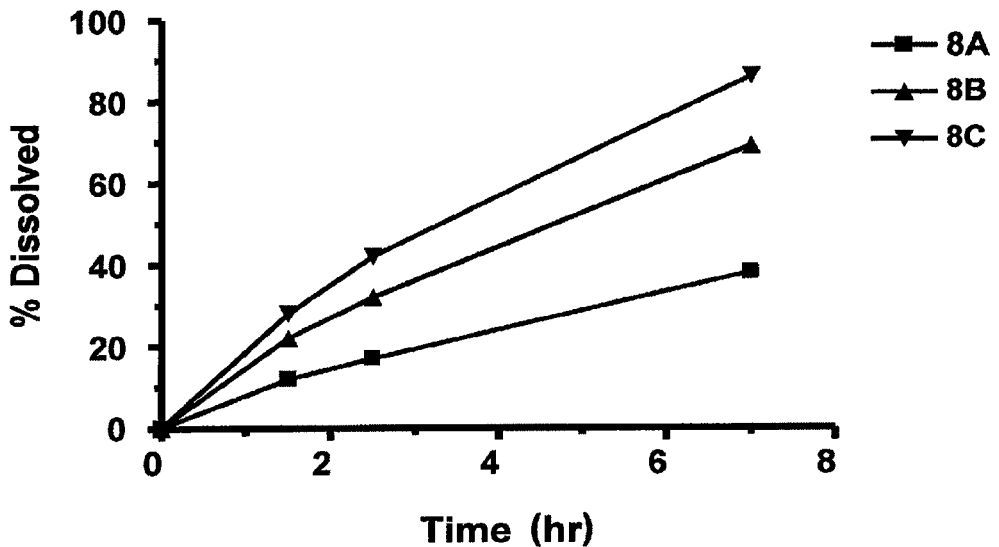
FIG. 9 is a graph showing the drug release property from each of the formulations prepared in Examples 8A to 8C in Experimental Example 8.

Experimental Example 8: Dissolution Test of Matrix Formulation Using Insoluble Polymer A drug release property from each of the formulations prepared in Examples 8A to 8C was evaluated by the method described in Experimental Example 1. The results are shown in Table 20 and FIG. 9.

TABLE 20

|  | Examples | | |
|---|---|---|---|
|  | 8 A | 8 B | 8 C |
| Dissolution rate 1.5 hours | 12 | 22 | 28 |
| Dissolution rate 2.5 hours | 17 | 32 | 42 |
| Dissolution rate 7 hours | 38 | 69 | 86 |

Figure 10:
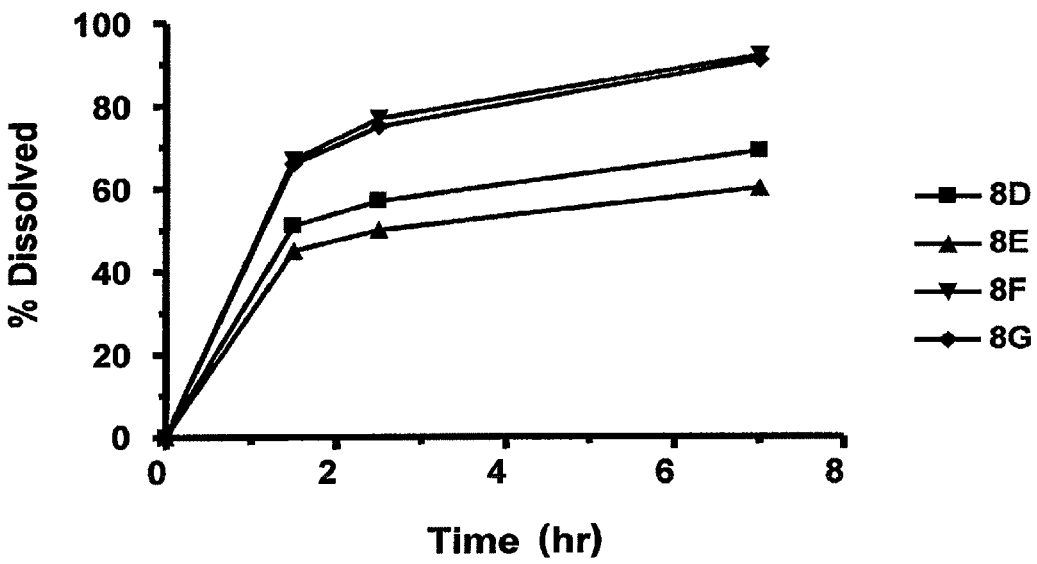
FIG. 10 is a graph showing the drug release property from each of the formulations prepared in Examples 8D to 8G in Experimental Example 8.

A drug release property from each of the formulations prepared in Examples 8D to 8G was evaluated by the method described in Experimental Example 1. The results are shown in Table 21 and FIG. 10.

TABLE 21

|  | Examples | | | |
|---|---|---|---|---|
|  | 8 D | 8 E | 8 F | 8 G |
| Dissolution rate 1.5 hours | 51 | 45 | 67 | 66 |
| Dissolution rate 2.5 hours | 57 | 50 | 77 | 75 |
| Dissolution rate 7 hours | 69 | 60 | 92 | 91 |

Experimental Example 9: Pharmacokinetics (PK) Test of Immediate Release Formulation (Capsule Formulation) in Human An immediate release formulation (capsule formulation) containing compound A was administered to healthy subjects in a fasted state, before 30 min from the intake of a meal, or after 30 min from the meal, and the drug concentration in the plasma was measured. The immediate release formulations (capsule formulations) containing 0.1 mg, 1 mg, 5 mg, 20 mg, and 80 mg of the compound A were used in combinations as needed so that the dose of compound A became 0.1 mg, 1 mg, 3 mg, 10 mg, 30 mg, 100 mg, 160 mg, 240 mg, and 340 mg.

Figure 11:
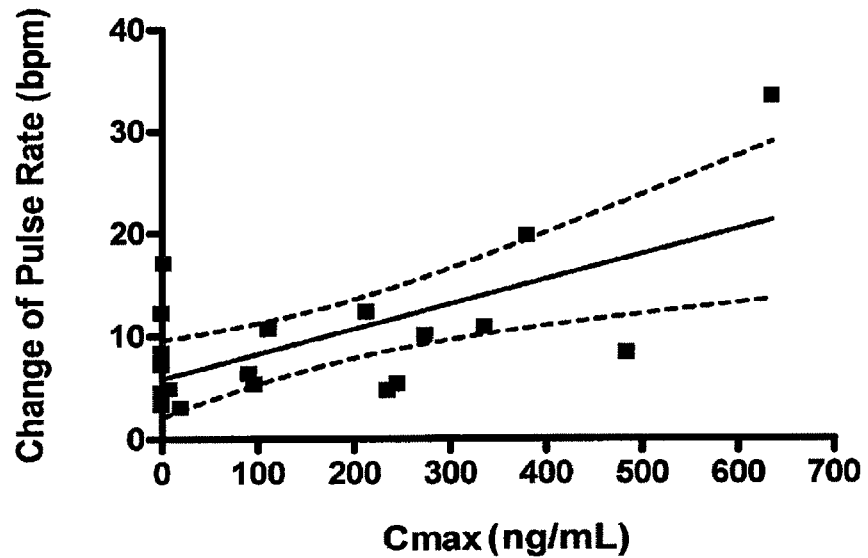
FIG. 11 is a graph showing the relation between Cmax and the increase in heart rate from the base line in Experimental Example 9 (a dotted line shows 95% confidence interval).

Results are shown in FIG. 11. When the maximum plasma concentration (Cmax) of compound A and the increase in heart rate from the base line were analyzed, a positive correlation was observed.

Experimental Example 10: Pharmacokinetics (PK) Test of Sustained Release Hydrogel-Forming Formulation in Human The pharmaceutical composition for modified release of the present invention prepared in Example 1A or 1B (containing compound A in an amount corresponding to 200 mg) was administered to healthy subjects in a fasted state (Fasted) or after 30 min from the intake of a meal (Fed), and the drug concentration in the plasma was measured. On the other hand, two capsules of the pharmaceutical composition (conventional formulation) (containing compound A in an amount corresponding to 160 mg) of Comparative Example 1 was administered to healthy subjects in a fasted state or after 30 min from the intake of a meal, and the drug concentration in the plasma was measured.

Figure 12:
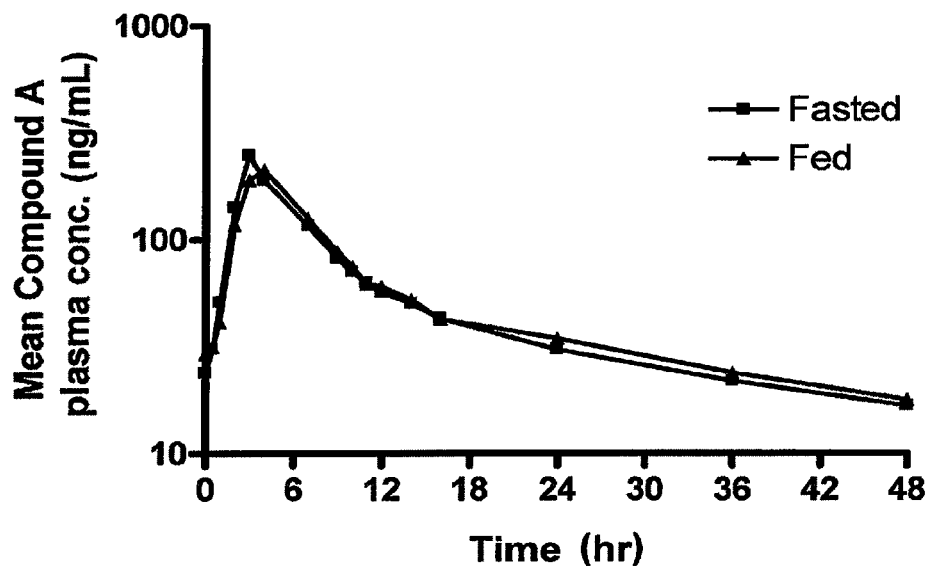
FIG. 12 is a graph showing blood concentration profiles after the administration of the formulation of Example 1A in a fasted state or after 30 minutes from the intake of food in Experimental Example 10.
Figure 13:
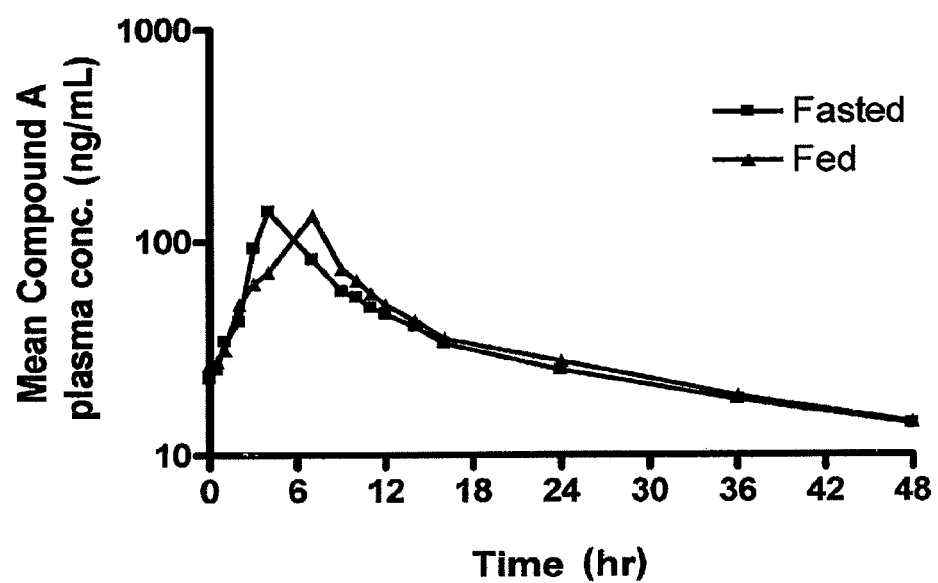
FIG. 13 is a graph showing the blood concentration profiles after the administration of the formulation of Example 1B in a fasted state or after 30 minutes from the intake of food in Experimental Example 10.

The results in the pharmaceutical composition for modified release of the present invention prepared in Example 1A are shown in FIG. 12, and the results in the pharmaceutical composition for modified release of the present invention prepared in Example 1B are shown in FIG. 13, respectively.

With respect to the conventional formulation, the rate of decrease of Cmax in the fed state was 67%, in comparison with that in the fasted state, and the rate of decrease of AUC was 47% (Cmax in the fasted state was approximately three times higher than that in the fed state). With respect to the pharmaceutical compositions for modified release (1A and 1B) of the present invention, the rates of decrease of Cmax in the fed state were 4% and 10%, in comparison with those in the fasted state, and the rates of decrease of AUC were 10% and −4%. These results indicated that the reductions of Cmax and AUC caused by food intake could be significantly alleviated by the pharmaceutical composition for modified release of the present invention.

Furthermore, the maximum plasma concentration after the administration of the pharmaceutical composition for modified release prepared in Example 1A of the present invention was 274 ng/mL and 264 ng/mL in the fasted state and in the fed state, respectively. Similarly, in Example 1B, they were 155 ng/mL and 140 ng/ml, respectively. Furthermore, the increase in heart rate is 13 bpm or less in both.

INDUSTRIAL APPLICABILITY

According to the present invention, a pharmaceutical composition for modified release capable of reducing the food effects observed in conventional tablets can be provided. Further, according to the present invention, a pharmaceutical composition for modified release is capable of anticipating and preventing the occurrence of adverse effects, such as an increase in heart rate, even at a single dose per day.

As above, the present invention was explained with reference to particular embodiments, but modifications and improvements obvious to those skilled in the art are included in the scope of the present invention.

We claim:

1. A method for treating overactive bladder such that the treating is with a reduced food effect, the method comprising administering orally to a subject in need thereof a tablet comprising 25 mg of (R)-2-(2-aminothiazol-4-yl)-4'-[2-[(2-hydroxy-2-phenylethyl)amino]ethyl]acetic acid anilide in a sustained release hydrogel-forming formulation, wherein the sustained release hydrogel-forming formulation further comprises a carrier and provides a continuous drug release for at least 4 hours after oral administration, wherein the reduced food effect is compared to that after oral administration of an immediate release formulation comprising (R)-2-(2-aminothiazol-4-yl)-4'-[2-[(2-hydroxy-2-phenylethyl)amino]ethyl]acetic acid anilide, and is a difference in a rate of decrease of $C_{max}$ of 10% or more, and wherein the immediate release formulation is a capsule.

2. The method according to claim 1, wherein the capsule further comprises D-mannitol.

3. The method according to claim 1, wherein the capsule is produced by a process comprising:
mixing (R)-2-(2-aminothiazol-4-yl)-4'-[2-[(2-hydroxy-2-phenylethyl)amino]ethyl]acetic acid anilide with D-mannitol and purified water to form a mixture;
kneading the mixture to form a kneaded product;
sieving the kneaded product and drying by using a fluidized bed granulating apparatus to form a dried product; and
sieving the dried product and filling the capsule.

4. The method according to claim 1, wherein the sustained release hydrogel-forming formulation comprises polyethylene oxide and polyethylene glycol.

5. The method according to claim 4, wherein the polyethylene oxide has an average molecular weight of 200,000 to 5,000,000, and the polyethylene glycol is selected from the group consisting of PEG 400, PEG 1500, PEG 4000, PEG 6000, and PEG 20000.

6. The method according to claim 4, wherein the polyethylene oxide has an average molecular weight of 2,000,000 to 4,000,000, and the polyethylene glycol is selected from the group consisting of PEG 400, PEG 1500, PEG 4000, PEG 6000, and PEG 20000.

7. The method according to claim 6, wherein the polyethylene oxide has the average molecular weight of 2,000,000.

8. The method according to claim 5, wherein the polyethylene glycol is PEG 6000.

9. The method according to claim 7, wherein the polyethylene glycol is PEG 6000.

10. The method according to claim 3, wherein the sustained release hydrogel-forming formulation comprises polyethylene oxide and polyethylene glycol.

11. The method according to claim 10, wherein the polyethylene oxide has an average molecular weight of 200,000 to 5,000,000, and the polyethylene glycol is selected from the group consisting of PEG 400, PEG 1500, PEG 4000, PEG 6000, and PEG 20000.

12. The method according to claim 10, wherein the polyethylene oxide has an average molecular weight of 2,000,000 to 4,000,000, and the polyethylene glycol is selected from the group consisting of PEG 400, PEG 1500, PEG 4000, PEG 6000, and PEG 20000.

13. The method according to claim 11, wherein the polyethylene oxide has the average molecular weight of 2,000,000.

14. The method according to claim 11, wherein the polyethylene glycol is PEG 6000.

15. The method according to claim 13, wherein the polyethylene glycol is PEG 6000.

16. A method for treating overactive bladder such that the treating is with a reduced food effect, the method comprising administering orally to a subject in need thereof a tablet comprising 50 mg of (R)-2-(2-aminothiazol-4-yl)-4'-[2-[(2-hydroxy-2-phenylethyl)amino]ethyl]acetic acid anilide in a sustained release hydrogel-forming formulation, wherein the sustained release hydrogel-forming formulation further comprises a carrier and provides a continuous drug release for at least 4 hours after oral administration, wherein the reduced food effect is compared to that after oral administration of an immediate release formulation comprising (R)-2-(2-aminothiazol-4-yl)-4'-[2-[(2-hydroxy-2-phenylethyl)amino]ethyl]acetic acid anilide, and is a difference in a rate of decrease of $C_{max}$ of 10% or more, and wherein the immediate release formulation is a capsule.

17. The method according to claim 16, wherein the capsule further comprises D-mannitol.

18. The method according to claim 16, wherein the capsule is produced by a process comprising:

mixing (R)-2-(2-aminothiazol-4-yl)-4'-[2-[(2-hydroxy-2-phenylethyl)amino]ethyl]acetic acid anilide with D-mannitol and purified water to form a mixture;

kneading the mixture to form a kneaded product;

sieving the kneaded product and drying by using a fluidized bed granulating apparatus to form a dried product; and sieving the dried product and filling the capsule.

19. The method according to claim 16, wherein the sustained release hydrogel-forming formulation comprises polyethylene oxide and polyethylene glycol.

20. The method according to claim 19, wherein the polyethylene oxide has an average molecular weight of 200,000 to 5,000,000, and the polyethylene glycol is selected from the group consisting of PEG 400, PEG 1500, PEG 4000, PEG 6000, and PEG 20000.

21. The method according to claim 19, wherein the polyethylene oxide has an average molecular weight of 2,000,000 to 4,000,000, and the polyethylene glycol is selected from the group consisting of PEG 400, PEG 1500, PEG 4000, PEG 6000, and PEG 20000.

22. The method according to claim 20, wherein the polyethylene oxide has the average molecular weight of 2,000,000.

23. The method according to claim 20, wherein the polyethylene glycol is PEG 6000.

24. The method according to claim 22, wherein the polyethylene glycol is PEG 6000.

25. The method according to claim 18, wherein the sustained release hydrogel-forming formulation comprises polyethylene oxide and polyethylene glycol.

26. The method according to claim 25, wherein the polyethylene oxide has an average molecular weight of 200,000 to 5,000,000, and the polyethylene glycol is selected from the group consisting of PEG 400, PEG 1500, PEG 4000, PEG 6000, and PEG 20000.

27. The method according to claim 25, wherein the polyethylene oxide has an average molecular weight of 2,000,000 to 4,000,000, and the polyethylene glycol is selected from the group consisting of PEG 400, PEG 1500, PEG 4000, PEG 6000, and PEG 20000.

28. The method according to claim 26, wherein the polyethylene oxide has the average molecular weight of 2,000,000.

29. The method according to claim 26, wherein the polyethylene glycol is PEG 6000.

30. The method according to claim 28, wherein the polyethylene glycol is PEG 6000.

* * * * *

UNITED STATES PATENT AND TRADEMARK OFFICE
CERTIFICATE OF CORRECTION

PATENT NO. : 12,097,189 B1
APPLICATION NO. : 18/613281
DATED : September 24, 2024
INVENTOR(S) : Yuuki Takaishi et al.

It is certified that error appears in the above-identified patent and that said Letters Patent is hereby corrected as shown below:

On the Title Page

Item (57):
"400 ng/ml" should read --400 ng/mL--.

In the Specification

Column 3:
Line 23, "400 ng/ml" should read --400 ng/mL--; and
Lines 26-27, "300 ng/ml" should read --300 ng/mL--.

Column 5:
Line 31, "400 ng/ml" should read --400 ng/mL--.

Column 8:
Line 5, "400 ng/ml" should read --400 ng/mL--; and
Line 51, "400 ng/ml" should read --400 ng/mL--.

Column 10:
Line 30, "7, 500 mPa·s" should read --7,500 mPa·s--.

Column 12:
Line 25, "1, 200-1, 800 mPa·s" should read --1,200-1,800 mPa·s--.

Column 45:
Line 40, "140 ng/ml" should read --10 ng/mL--.

Signed and Sealed this
Third Day of December, 2024

Katherine Kelly Vidal
*Director of the United States Patent and Trademark Office*